(12) United States Patent
Blackwell et al.

(10) Patent No.: US 10,807,943 B2
(45) Date of Patent: Oct. 20, 2020

(54) NON-LACTONE CARBOCYCLIC MODULATORS OF BACTERIAL QUORUM SENSING

(71) Applicant: Wisconsin Alumni Research Foundation, Madison, WI (US)

(72) Inventors: Helen E. Blackwell, Middleton, WI (US); Christine E. McInnis, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/670,298

(22) Filed: Aug. 7, 2017

(65) Prior Publication Data

US 2017/0334835 A1 Nov. 23, 2017

Related U.S. Application Data

(63) Continuation of application No. 14/104,235, filed on Dec. 12, 2013, now Pat. No. 9,758,472, which is a
(Continued)

(51) Int. Cl.
| | |
|---|---|
| *C07C 235/80* | (2006.01) |
| *A61K 31/164* | (2006.01) |
| *C07C 233/11* | (2006.01) |
| *A61K 31/165* | (2006.01) |
| *A61K 31/167* | (2006.01) |
| *A61K 31/22* | (2006.01) |
| *A61K 31/245* | (2006.01) |
| *A61K 31/341* | (2006.01) |
| *A61K 31/381* | (2006.01) |
| *A61K 31/405* | (2006.01) |
| *A61K 31/415* | (2006.01) |
| *C07C 233/51* | (2006.01) |
| *C07C 235/34* | (2006.01) |
| *C07C 323/62* | (2006.01) |
| *C07D 231/40* | (2006.01) |
| *C07D 307/52* | (2006.01) |

(Continued)

(52) U.S. Cl.
CPC ............ *C07C 233/11* (2013.01); *A01N 37/22* (2013.01); *A01N 37/42* (2013.01); *A01N 43/08* (2013.01); *A01N 43/10* (2013.01); *A01N 43/38* (2013.01); *A01N 43/56* (2013.01); *A61K 31/164* (2013.01); *A61K 31/165* (2013.01); *A61K 31/167* (2013.01); *A61K 31/22* (2013.01); *A61K 31/221* (2013.01); *A61K 31/245* (2013.01); *A61K 31/341* (2013.01); *A61K 31/381* (2013.01); *A61K 31/404* (2013.01); *A61K 31/405* (2013.01); *A61K 31/415* (2013.01); *A61K 45/06* (2013.01); *C07C 233/10* (2013.01); *C07C 233/51* (2013.01); *C07C 235/34* (2013.01); *C07C 235/80* (2013.01); *C07C 323/62* (2013.01); *C07D 209/18* (2013.01); *C07D 231/40* (2013.01); *C07D 307/52* (2013.01); *C07D 333/36* (2013.01); *C07D 409/12* (2013.01); *C07C 2601/08* (2017.05)

(58) Field of Classification Search
CPC ............................ C07C 235/80; A61K 31/164
See application file for complete search history.

(56) References Cited

U.S. PATENT DOCUMENTS

| | | |
|---|---|---|
| 4,072,703 A | 2/1978 | Blum |
| 5,278,326 A | 1/1994 | Angelli-Szafran et al. |

(Continued)

FOREIGN PATENT DOCUMENTS

| | | |
|---|---|---|
| EP | 2 078 713 | 7/2009 |
| EP | 2 100 602 | 9/2009 |

(Continued)

OTHER PUBLICATIONS

McInnis et al.; "Toward New, Non-acyl Homoserine Lactone Modulators of Bacterial Quorum Sensing"; 236th American Chemical Society Meeting, Philadelphia, PA< Aug. 17-21, 2008; Poster Presentation, ORGN 142 poster presented Division of Organic Chemistry Aug. 17, 2008 (Year: 2008).*

(Continued)

*Primary Examiner* — Timothy P Thomas
(74) *Attorney, Agent, or Firm* — Leydig, Voit & Mayer, Ltd.

(57) ABSTRACT

Non-lactone carbocyclic modulators of bacterial quorum sensing. Pharmaceutical composition containing such modulators. Methods employing such modulators for modulation of quorum sensing. Compounds are exemplified by those of formula:

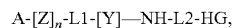

where A is an optionally substituted aryl or heteroaryl group having one or two 5- or 6-member rings with up to 1-3 heteroatoms in a ring, or a substituted or unsubstituted C1-C12 acyclic aliphatic group and HG is an optionally substituted cyclopentyl group. Compounds include those where n is 1 or 0, Z is —CO—, —O—CO—, —CO—O—, —NH—CO—, —CO—NH—, —NH—CO—NH—, —O—, —S—, or —NH$_2$, Y is —NH—CO—, —CO—CH$_2$—C(Y1)-, or —SO$_2$—, where Y1 is —OH, —SH, —NH$_2$ or —F; and L1 and L2 independently are —[CH$_2$]p1- and —[CH$_2$]p2-, where p1 and p2, independently, are 0 or integers ranging from 1-3.

12 Claims, 20 Drawing Sheets

Related U.S. Application Data continuation of application No. 12/822,929, filed on Jun. 24, 2010, now Pat. No. 8,624,063.

(60) Provisional application No. 61/222,075, filed on Jun. 30, 2009.

(51) Int. Cl.
| | |
|---|---|
| C07D 333/36 | (2006.01) |
| C07D 409/12 | (2006.01) |
| C07C 233/10 | (2006.01) |
| A01N 37/22 | (2006.01) |
| A01N 37/42 | (2006.01) |
| A01N 43/08 | (2006.01) |
| A01N 43/10 | (2006.01) |
| A01N 43/38 | (2006.01) |
| A01N 43/56 | (2006.01) |
| A61K 31/221 | (2006.01) |
| A61K 31/404 | (2006.01) |
| A61K 45/06 | (2006.01) |
| C07D 209/18 | (2006.01) |

(56) References Cited

U.S. PATENT DOCUMENTS

| | | |
|---|---|---|
| 5,410,049 A | 4/1995 | Chambers |
| 5,593,827 A | 1/1997 | Bycroft et al. |
| 5,776,974 A | 7/1998 | Bycroft et al. |
| 6,555,356 B2 | 4/2003 | Kjelleberg et al. |
| 6,559,176 B1 | 5/2003 | Bassler et al. |
| 6,756,404 B2 | 6/2004 | Livinghouse |
| 6,780,890 B2 | 8/2004 | Bassler et al. |
| 6,855,513 B1 | 2/2005 | Whitely et al. |
| 6,958,145 B2 | 10/2005 | Kumar et al. |
| 7,026,353 B2 | 4/2006 | Kjelleberg et al. |
| 7,074,776 B2 | 7/2006 | Cooper et al. |
| 7,078,435 B2 | 7/2006 | Livinghouse |
| 7,094,384 B1 | 8/2006 | Davies et al. |
| 7,332,509 B2 | 2/2008 | Schaper et al. |
| 7,335,779 B2 | 2/2008 | Ammendola |
| 7,338,969 B2 | 3/2008 | Ammendola |
| 7,498,292 B2 | 3/2009 | Suga et al. |
| 7,642,285 B2 | 1/2010 | Blackwell et al. |
| 7,659,409 B2 | 2/2010 | Takehara et al. |
| 7,737,164 B2 | 6/2010 | Blackwell et al. |
| 7,910,622 B2 | 3/2011 | Blackwell et al. |
| 8,227,616 B2 | 7/2012 | Blackwell et al. |
| 8,247,443 B2 | 8/2012 | Bassler et al. |
| 8,269,024 B2 | 9/2012 | Blackwell et al. |
| 8,350,061 B2 | 1/2013 | Iyer et al. |
| 8,367,680 B2 | 2/2013 | Blackwell et al. |
| 8,618,327 B2 | 12/2013 | Blackwell et al. |
| 8,624,063 B2 | 1/2014 | Blackwell et al. |
| 8,815,943 B2 | 8/2014 | Blackwell et al. |
| 9,758,472 B2 | 9/2017 | Blackwell et al. |
| 9,796,694 B2 | 10/2017 | Blackwell et al. |
| 2002/0037578 A1 | 2/2002 | Kjellberg et al. |
| 2002/0177715 A1 | 11/2002 | Pesci et al. |
| 2003/0105143 A1 | 6/2003 | Ammendola et al. |
| 2003/0125381 A1 | 7/2003 | England et al. |
| 2003/0198692 A1 | 10/2003 | Holmstrom et al. |
| 2003/0224032 A1 | 12/2003 | Read et al. |
| 2004/0072898 A1 | 2/2004 | Kjelleberg et al. |
| 2004/0110966 A1 | 4/2004 | Kumar et al. |
| 2004/0115732 A1 | 6/2004 | Suga et al. |
| 2004/0147595 A1 | 7/2004 | Kjelleberg et al. |
| 2004/0180829 A1 | 9/2004 | Bassler et al. |
| 2004/0180936 A1 | 9/2004 | Auvin et al. |
| 2004/0235914 A1 | 10/2004 | Ammendola et al. |
| 2005/0054722 A1 | 1/2005 | England et al. |
| 2005/0215772 A1 | 9/2005 | Kumar |
| 2006/0052425 A1 | 3/2006 | Handelsman et al. |
| 2006/0178430 A1 | 8/2006 | Blackwell et al. |
| 2006/0264641 A1 | 11/2006 | Berendes et al. |
| 2007/0054883 A1 | 3/2007 | Cooper et al. |
| 2007/0093534 A1 | 4/2007 | Ammendola et al. |
| 2007/0128658 A1 | 4/2007 | Blackwell et al. |
| 2007/0155698 A1 | 7/2007 | Steinberg et al. |
| 2007/0184014 A1 | 8/2007 | Ammendola et al. |
| 2007/0196340 A1 | 8/2007 | Ammendola et al. |
| 2007/0197492 A1 | 8/2007 | Ammendola et al. |
| 2007/0203128 A1 | 8/2007 | Ammendola et al. |
| 2007/0208012 A1 | 9/2007 | Ammendola et al. |
| 2007/0264715 A1 | 11/2007 | Robinson et al. |
| 2008/0009528 A1 | 1/2008 | Blackwell et al. |
| 2008/0027115 A1 | 1/2008 | Suga et al. |
| 2008/0176938 A1 | 7/2008 | Ammendola et al. |
| 2008/0182878 A1 | 7/2008 | Ammendola et al. |
| 2008/0188491 A1 | 8/2008 | Ammendola et al. |
| 2008/0188535 A1 | 8/2008 | Ammendola et al. |
| 2008/0188536 A1 | 8/2008 | Ammendola et al. |
| 2008/0194588 A1 | 8/2008 | Ammendola et al. |
| 2008/0194607 A1 | 8/2008 | Ammendola et al. |
| 2008/0214635 A1 | 9/2008 | Ammendola et al. |
| 2008/0312319 A1 | 12/2008 | Blackwell et al. |
| 2009/0123512 A1 | 5/2009 | Muh et al. |
| 2009/0163545 A1 | 6/2009 | Goldfarb |
| 2009/0192192 A1 | 7/2009 | Ammendola et al. |
| 2009/0270423 A1 | 10/2009 | Blackwell et al. |
| 2010/0056602 A1 | 3/2010 | Salman et al. |
| 2010/0160423 A1 | 6/2010 | Bassler et al. |
| 2010/0261763 A1 | 10/2010 | Blackwell et al. |
| 2010/0305182 A1 | 12/2010 | Blackwell et al. |
| 2011/0046195 A1 | 2/2011 | Blackwell et al. |
| 2011/0212860 A1 | 9/2011 | Blackwell et al. |
| 2014/0142156 A1 | 5/2014 | Blackwell et al. |
| 2017/0334835 A1 | 11/2017 | Blackwell et al. |

FOREIGN PATENT DOCUMENTS

| | | |
|---|---|---|
| JP | H02-235850 | 9/1990 |
| JP | H03-031245 | 2/1991 |
| JP | H03-232849 | 10/1991 |
| WO | WO 1992/018614 | 10/1992 |
| WO | WO 1996/029392 | 9/1996 |
| WO | WO 1999/027786 | 6/1999 |
| WO | WO 1999/053915 | 10/1999 |
| WO | WO 2001/043739 | 6/2001 |
| WO | WO 2001/068091 | 9/2001 |
| WO | WO 2001/076594 | 10/2001 |
| WO | WO 2001/085664 | 11/2001 |
| WO | WO 2002/000639 | 1/2002 |
| WO | WO 2002/018342 | 3/2002 |
| WO | WO 2002/047681 | 6/2002 |
| WO | WO 2002/052949 | 7/2002 |
| WO | WO 2002/102370 | 12/2002 |
| WO | WO 2003/039529 | 5/2003 |
| WO | WO 2003/039549 | 5/2003 |
| WO | WO 2003/106445 | 12/2003 |
| WO | WO-2004007498 A2 * | 1/2004 ........... C07D 487/04 |
| WO | WO 2004/016213 | 2/2004 |
| WO | WO 2004/106299 | 12/2004 |
| WO | WO 2006/079015 | 7/2006 |
| WO | WO 2006/084056 | 8/2006 |
| WO | WO 2008/016738 | 2/2008 |
| WO | WO 2008/116029 | 9/2008 |
| WO | WO 2009/050575 | 4/2009 |
| WO | WO 2009/077844 | 6/2009 |
| WO | WO 2010/010380 | 1/2010 |

OTHER PUBLICATIONS

Blackburn et al.; "Identification and characterization of 4-aryl-3,4-dihydropyrinnidin-2(1H)-ones as inhibitors of the fatty acid transporter FATP4"; 2006; 16: 3504-3509 (Year: 2006).*

Mattman et al.; "Potent and Selective Synthetic Modulators of a Quorum Sensing Repressor in Pseudomonas aeruginosa Identified from Second-Generation Libraries of N-Acylated I-Homoserine Lactones"; 2011; ChemBioChem; 12: 942-949 (Year: 2011).*

(56) References Cited

OTHER PUBLICATIONS

Wysoczynski-Horita et al.; "Mechanism of agonism and antagonism of the Pseudomonas aeruginosa quorum sensing regulator QscR with non-native ligands"; 2018; Molecular Microbiology; 108(3): 240-257 (Year: 2018).*
McInnis et al.; Design, Synthesis and biological evaluation of abiotic, non-lactone modulators of Lux-R type quorum sensing; 2011; Bioorganic & Medicinal Chemistry; 19: 4812-4819 (Year: 2011).*
Kaufmann et al.; "Bacterial quorum sensing: a new target for anti-infective immunotherapy"; 2008; Expert Opinion on Biological Therapy; 8(6): 719-724; DOI: 10.1517/14712598.8.6.719 (Year: 2008).*
Persson et al.; "Rational design and synthesis of new quorum-sensing inhibitors derived from acylated homoserine lactones and natural products from garlic"; 2005; Org. Biomol. Chem.; 3:253-262; DOI:10.1039/b415761c (Year: 2005).*
U.S. Appl. No. 11/275,896, filed Feb. 2, 2006, 20060178430, Aug. 10, 2006, U.S. Pat. No. 7,642,285, Jan. 5, 2010.
U.S. Appl. No. 12/641,056, filed Dec. 17, 2009, 2010035182, Dec. 2, 2010, U.S. Pat. No. 8,269,024, Sep. 18, 2012.
U.S. Appl. No. 12/822,929, filed Jun. 24, 2010, 20110046195, Feb. 24, 2011, U.S. Pat. No. 8,624,063, Jan. 7, 2014.
U.S. Appl. No. 14/104,235, filed Dec. 12, 2013, 20140142156, May 22, 2014, U.S. Pat. No. 9,758,472, Sep. 12, 2017.
U.S. Appl. No. 12/051,826, filed Mar. 19, 2008, 20080312319, Dec. 18, 2008, U.S. Pat. No. 7,910,622, Mar. 22, 2011.
U.S. Appl. No. 13/032,063, filed Feb. 22, 2011, 20110212860, Sep. 1, 2011, U.S. Pat. No. 8,815,943, Aug. 26, 2014.
U.S. Appl. No. 14/328,515, filed Jul. 10, 2014, 20150080349, Mar. 19, 2015, U.S. Pat. No. 9,796,694, Oct. 24, 2017.
U.S. Appl. No. 15/701,565, filed Sep. 12, 2017, 20170369462, Dec. 28, 2017.
U.S. Appl. No. 15/431,295, filed Feb. 13, 2017, 20170231962, Aug. 17, 2017.
SCIFINDER® Record of CAPLUS English Abstract of JP 3232849 with chemical structures; Accession No. 1992:105870 (1992).
CAPLUS English Abstract of JP H03-031245, Izawa et al. (1991).
CAPLUS English Abstract of JP H02-235850, Izawa et al. (1990).
Bassler et al. (1993) "Intercellular Signaling in Vibrio harveyi: Sequence and Function of Genes Regulating Expression of Luminescence," Mol. Microbial. 9(4):773-786.
Bassler et al. (1994) "Multiple Signaling Systems Controlling Expression of Luminescence in Vibrio harveyi: Sequence and Function of Genes Encoding a Second Sensory Pathway," Mol. Microbial. 13(2):273-286.
Bassler et al. (1995) "Intercellular Communication in Marine Vibrio Species: Density-Dependent Regulation of the Expression of Bioluminescence," Two Component Signal Transduction. Am. Soc. Microbial. 431-445.
Bassler et al. (1997) "Cross-Species Induction of Luminescence in the Quorum-Sensing Bacterium *Vibrio harveyi*," J. Bacterial. 179(12):4043-4045.
Bassler et al. (Apr. 2006) "Bacterially Speaking," Cell. 125(2):237-246.
Blackwell (2003) "Out of the Oil Bath and into the Oven—Microwave-Assisted Combinatorial Chemistry Heats up," Org. Biomol. Chem. 1:1251-1255.
Blackwell (May 2006) "Hitting the SPOT: Small-Molecule Macroarrays Advance Combinatorial Synthesis," Curr. Opin. Chem. Biol. 10:203-212.
Bottomley et al. (May 2007) "Molecular Insights into Quorum Sensing in the Human Pathogen Pseudomonas aeruginosa from the Structure of the Virulence Regulator LasR Bound to Its Autoinducer," J. Biol. Chem. 282(18):13592-13600.
Byers et al (2002) "Nonenzymatic Turnover of an Erwinia carotovora Quorum Sensing Signaling Molecule," J. Bacterial. 184(4):1163-1171.
Castang et al. (2004) "N-Sulfonyl Homoserine Lactone as Antagonists of Bacterial Quorum Sensing," Bioorg. Med. Chem. Lett. 14(20):5145-5149.
Davies et al. (1998) "The Involvement of Cell-to-Cell Signals in the Development of a Bacterial Biofilm," Science. 280:295-298.
De Kievit et al. (2001) "Quorum-Sensing Genes in Pseudomonas aeruginosa Biofilms: Their Role and Expression Patterns," Appl. Environ. Microbial. 67(4):1865-1873.
De Kievit et al. (2000) "Bacterial Quorum Sensing in Pathogenic Relationships," Infect. Immun. 68(9):4839-4849.
Deluca et al. (2003) "Preparation of pyrazole and isoxaxazole libraries on cellulose beads: a new cheap and versatile biopolymer," C.R. Chimie. 6:607-611.
Eberhard et al. (2000) "Chemical Synthesis of Bacterial Autoinducers and Analogs," Methods Enzymol. 305:301-315.
Eberhard et al. (1986) "Analogs of the Autoinducer of Bioluminescence in Vibrio fisher," Arch Microbial. 146(1):35-40.
Elsinghorst et al. (Nov. 2006) "Novel Heterobivalent Tacrine Derivatives as Cholinesterase Inhibitors with Notable Selectivity Toward Butyrylcholinesterase," J. Med. Chem. 49(25):7540-7544.
Estephane et al. (Jun. 2008) "N-Acyl-3-amino-5H-furanone Derivatives as New Inhibitors of LuxR-Dependent Quorum Sensing: Synthesis, Biological Evaluation and Binding Mode Study," Bioorg. Med. Chem. Lett. 18:4321-4324.
Fletcher et al. (Jul. 2007) "A Dual Biosensor for 2-alkyl-4-quinolone Quorum Sensing Signal Molecules," Environ. Microbial. 9(11):2683-2693.
Frezza et al. (Mar. 2006) "Synthesis and Biological Evaluation of Homoserine Lactone Derived Ureas as Antagonists of Bacterial Quorum Sensing," Bioorg. Med. Chem. 14:4781-4791.
Fuqua et al. (2001) "Regulation of Gene Expression by Cell-To-Cell Communication: Acyi-Homoserine Lactone Quorum Sensing," Ann. Rv. Genet. 35:439-468.
Fuqua et al. (2002) "Listening in on Bacteria: Acyi-Homoserine Lactone Signalling," Nat. Rev. Mol. Cell Biol. 3:685-695.
Gasperi et al. (2003) "Synthesis or a-Amino y-Butyrolactone Derivatives by Ariridination of a-ylidene y-butyrolactones," Tetrahedron Letters. 44(27):4953-4956.
Geske et al. (2005) "Small Molecule Inhibitors of Bacterial Quorum Sensing and Biofilm Formation," J. Am. Chem. Soc. 127:12762-12763.
Geske et al. (May 2007) "N-Phenylacetanoyi-L-Homoserine Lactones Can Strongly Antagonize or Superagonize Quorum Sensing in Vibrio fischeri," ACS Chem. Biol. 2(5):315-320.
Geske et al. (Oct. 2007) "Modulation of Bacterial Quorum Sensing with Synthetic Ligands: Systematic Evaluation of N-Acylated Homoserine Lactones in Multiple Species and New Insights into Their Mechanisms of Action," J. Am. Chem. Soc. 129(44):13613-13625.
Geske et al. (Jan. 2008) "Comparative Analyses of N-Acylated Homoserine Lactones Reveal Unique Structural Features that Dictate Their Ability to Activate or Inhibit Quorum Sensing," ChemBioChem. 9:389-400.
Geske et al. (Jun. 2008) "Expanding Dialogues: From Natural Autoinducers to Non-Natural Analogues that Modulate Quorum Sensing in Gram-Negative Bacteria," Chem. Soc. Rev. 37:1432-1447.
Geske et al. (Jul. 2008) "Evaluation of a Focused Library of N-aryl L-Homoserine Lactones Reveals a New Set of Potent Quorum Sensing Modulators," Bioorg. Med. Chem. Lett. 18:5978-5981.
Gerdt et al. (2014) "Mutational Analysis of the Quorum-Sensing Receptor LasR Reveals Interaction that Govern Actiavtion and Inhibition by Nonlactone Ligands," Chemistry & Biol, 21:1361-1369.
Glansdorp et al. (2004) "Synthesis and Stability of Small Molecule Probes for Pseudomonas aeruginosa quorum Sensing Modulation," Org. Biomol. Chem. 2:3329-3336.
Gonzalez et al. (Dec. 2006) "Messing with Bacterial Quorum Sensing," Microbial. Mol. Biol. Rev. 70(4):859-875.
Greenberg et al. (1999) "Quorum Sensing in Gram-Negative Bacteria: An Important Signaling Mechanism in Symbiosis and Disease," Microbial Ecology and Infectious Disease, American Society for Microbiology. 112-122.

(56) References Cited

OTHER PUBLICATIONS

Hall-Stoodley et al. (2004) "Bacterial Biofilms: From the Natural Environment to Infectious Diseases," Nat. Rev. Microbiol. 2:95-108.
Hentzer et al. (2003) "Attenuation of Pseudomonas aeruginosa Virulence by Quorum Sensing Inhibitors," EMBO J. 22(15):3803-3815.
Hjelmgaard et al. (2003) "Synthesis of Furanone-Based Natural Product Analogues with Quorum Sensing Antagonist Activity," Bioorg. Med. Chem. 11:3261-3271.
Hodgkinson et al. (2012) "Design, Synthesis and Biological Evaluation of Non-Natural Modulators of Quorum Sensing Pseudomonas aeruginosa," Org. Biomol. Chem. 10:6032-6044.
Horikawa et al. (Feb. 2006) "Synthesis of Pseudomonas quorum-sensing autoinducer analogs and structural entities required for induction of apoptosis in macrophages," Bioorganic & Medicinal Chemistry Letters. 16:2130-2133.
Ikeda et al. (2001) "The Synthesis of Optically Pure Enantiomers of N-Acyl-Homoserine Lactone Autoinducers and Their Analogues," Chem. Lett. 30(4):314-315.
Ishida et al. (May 2007) "Inhibition of Quorum Sensing in Pseudomonas aeruginosa by N-acyl Cyclopentylamides," Appl. Environ. Microbial. 73(10):3183-3188.
Janssens et al. (Jan. 2007) "Synthesis of N-Acyl Homoserine Lactone Analogues Reveals Strong Activators of SdiA, the *Salmonella enterica* Serovar Typhimurium LuxR Homologue," Appl. Environ. Microbial. 73(2):535-544.
Jog et al. (Feb. 2006) "Stereoisomers of P. aeruginosa Autoinducer Analog to probe the Regulator Binding Site," Chem. Biol. 13:123-128.
Kapadnis et al. (Dec. 2008) "Towards Quorum-Quenching Catalytic Antibodies," Chem. Commun. 2009(5):538-540.
Kim et al. (Aug. 2008) "Furanone Derivatives as Quorum Sensing Antagonists of Pseudomonas aeruginosa," Appl. Microbial. Biotechnol. 80:37-47.
Kim et al. (Mar. 2009) "Structural understanding of quorum-sensing inhibitors by molecular modeling study in Pseudomonas aeruginosa," Appl. Microbial. Biotechnol. 83:1095-1103.
Kline et al. (1999) "Novel Synthetic Analogs of the Pseudomonas Autoinducer," Bioorg. Med. Chem. Lett. 9(24):3447-3452.
Ko et al. (1998) "New Cleavage Approached to Combinatorial Synthesis of Homoserine Lactones," Tetrahedron Lett. 39(3-4):297-300.
Koch et al. (2005) "The LuxR Receptor: The Sites of Interaction with Quorum-Sensing Signals and Inhibitors," Microbiology 151:3589-3602.
Krasnov et al. (1999) "Synthesis of 4-Maercaptoglytamic Acid Derivatives," Russian J. Org. Chem. 35(4):572-577.
Lee et al. (Jan. 2006) "Activity of Purified QscR, a Pseudomonas aeruginosa Orphan Quorum-Sensing Transcription Factor," Mol. Microbiol. 59(2):602-609.
Lee et al. (Oct. 2007) "Hydroxylated Hydrocinnamides as Hypocholesterolemic Agents," Bull. Korean Chem. Soc. 28(10):1787-1791.
Lee et al. (Mar. 2008) "2-Methoxycyclopentyl Analogues of a Pseudomonas aeruginosa Quorum Sensing Modulator," Molecular BioSystems. 4:505-507.
Lupp et al. (2003) "The Vibrio fischeri Quorum-Sensing Systems ain and lux Sequentially Induce Luminescence Gene Expressions and are Important for Persistence in the Squid Host," Mol. Microbiol. 50(1):319-331.
Lyon et al. (2003) "Chemical Signaling Among Bacteria and Its Inhibition," Chem. Biol. 10(11):1007-1021.
Marketon et al. (2003) "Quorum Sensing Controls Exopolysaccharide Production in *Sinorhizobium meliloti*," J. Bacteriology. 185(1):325-331.
Martinelli et al. (2004) "Effects of Natural and Chemically Synthesized Furanones on Quorum Sensing in Chromobacterium violaceum," BMC Microbiology. 4(25):1-10.

Matsuo et al. (1980) "Structure-activity relationships in tetramic acids and their copper(II) complexes," Chemical & Pharmaceutical Bulletin. 28(8):2494-2502. [Abstract].
Mattmann et al. (2011) "Potent and Selective Synthetic Modulators of a Quorum Sensing Repressor in Pseudomonas aeruginosa Identified from Second-Generation Libraries of N-Acylated L-Homoserine Lactones," ChemBioChem. 12:942-949.
Mattmann et al. (May 2008) "Synthetic Ligands that Activate and Inhibit a Quorum-Sensing Regulator in Pseudomonas aeruginosa," Biorg. Med. Chem. Lett. 18(10):3072-3075.
Mcclean et al. (1997) "Quorum Sensing and Chromobacterium Violaceum: Exploitation of Violacein Production and Inhibition for the Detection of N-acylhomoserine Lactones," Microbiology. 143:3703-3711.
Mcinnis et al. (2011) "Design, Synthesis, and Biological Evaluation of Abiotic, Non-Lactone Modulators of LuxR-Type Quorum Sensing," Bioorg Med Chem. 19(16):4812-4819.
Mcinnis et al. (2011) "Thiolactone Modulators of Quorum Sensing Revealed Through Library Design and Screening," Bioorg. Med. Chem. 19:4820-4828.
Mcinnis et al. (Jun. 2008) "Toward new, nonacyl homoserine lactone modulators of bacterial quorum sensing," $236^{th}$ American Chemical Society Meeting, Philadelphia, PA; Abstract of Poster Presentation ORGN 142 publicly available Jun. 30, 2008.
Mcinnis et al. (Aug. 2008) "Toward new, nonacyl homoserine lactone modulators of bacterial quorum sensing," $236^{th}$ American Chemical Society Meeting, Philadelphia, PA, Aug. 17-21, 2008; Poster Presentation, ORGN 142 poster presented Division of Organic Chemistry Aug. 17, 2008.
Metayer (1947) "Differences in behavior of aromatic and saturated cyclic hydrocarbons in the entrainment of polyhydroxy alcohols," Compt. Rend. 224:16435. SciFinder Record Accession No. 1948:625.
Muh et al. (Nov. 2006) "Novel Pseudomonas aeruginosa Quorum-Sensing Inhibitors Identifies in a Ultra-High-Throughput Screen," Antimicrob. Agents Chemother. 50(11):3674-3679.
Muh et al. (Nov. 2006) "A Structurally Unrelated Mimic of a Pseudomonas aeruginosa Acyl-Homoserine Lactone Quorum-Sensing Signal," Proc. Nat. Acad. Sci. 103(45):16948-16952.
Murga et al. (2001) "Biofilm Formation by Gram-Negative Bacteria on Central Venous Catheter Connectors: Effect of Conditioning Films in a Laboratory Model," J. Clin. Micro. 39(6):2294-2297.
Passador et al. (1996) "Functional Analysis of the Pseudomonas aeruginosa Autoinducer PAI," J. Bacterial. 178(20):5995-6000.
Patani et al. (1996) "Bioisosterism: A Rational Approach in Drug Design," Chemical Reviews. 96(8):3147-3176.
Paton et al. (2016) Isomer Count; The Goodman Group; University of Cambridge. Accessible on the Internet at URL: <http://www-jmg.ch.cam.ac.uk/data/isomercount>.
Pearson et al. (1994) "Structure of the Autoinducer Required for Expression of Pseudomonas aeruginosa Virulence Genes," Proc. Natl. Acad. Sci. 91:197-201.
Persson et al. (2005) "Rational Design and Synthesis of New Quorum-Sensing Inhibitors Derived from Acylated Homoserine Lactones and Natural Products from Garlic," Org. Biomol. Chem. 3:253-262.
Persson et al. (2005) "Quorum sensing inhibition: targeting chemical communication in gram-negative bacteria," Curr. Med. Chem. 12(26):3103-3115.
Ramussen et al. (Apr. 2006) "Quorum Sensing Inhibitors: A Bargain of Effects," Microbiology. 152:895-904.
Reverchon et al. (2002) "New Synthetic Analogues of N-acyl Homoserine Lactones as Agonists or Antagonists of Transcriptional Regulators Involved in Bacterial Quorum Sensing," Bioorg. Med. Chem. Lett. 12(8):1153-1157.
Rogers et al. (Jun. 2008) "Construction and Screening of a 2-Aminoimidazole Library Identifies a Small Molecule Capable of Inhibiting and Dispersing Bacterial Biofilms across Order, Class and Phylum," Angewandte Chemie Int. Ed. 47:5229-5231.
Schaefer et al. (1996) "Quorum Sensing in Vibrio fisheri: Probing Autoinducer-LuxR Interactions with Autoinducer Analogs," J. Bacterial. 178(10):2897-2901.

(56) References Cited

OTHER PUBLICATIONS

Schuster et al. (2004) "Promoter Specificity in Pseudomonas aeruginosa Quorum Sensing Revealed by DNA Binding of Purified LasR," Proc. Nat. Acad. Sci. USA 101(45):15833-15839.
Smith et al. (2003) "P. aeruginosa Quorum-Sensing Systems and Virulence," Cur. Opin. Microbial. 6(1):56-60.
Smith et al. (2003) "Induction and Inhibition of Pseudomonas aerinosa Quorum Sensing by Synthetic Autoinducer Analogs," Chem. Biol. 10(1):81-89.
Smith et al. (2003) "Library Screening for Synthetic Agonist and Antagonist of a Pseudomonas aeruqinosa Autoinducer," Chem. Biol. 10(6):563-571.
Smith et al. (2003) "P. aeruginosa Quorum-Sensing Systems and Virulence," Cur. Opin. Microbial. 6(1):56-60.
Swem et al. (Jul. 2009) "A Quorum-Sensing Antagonist Targets Both Membrane-Bound and Cytoplasmic Receptors and Controls Bacterial Pathogenicity," Molecular Cell. 35(2):143-153.
Taha et al. (Nov. 2006) "Discovery of Potent Inhibitor of Pseudomonal Quorum Sensing via Pharmacophore Modeling and in Silico Screening," Bioorg. Med. Chem. Lett. 16(22):5902-5906.
Teplitski et al. (2000) "Plants Secrete Substances that Mimic Bacterial N-Acyl Homoserine Lactone Signal Activities and Affect Population Density-Dependent Behaviors in Associated Bacteria," Mol. Plant-Microbe Interact. 13(6):637-648.
Urbanowski et al. (2004) "Reversible Acyl-Homoserine Lactone Binding to Purified Vibrio fischeri LuxR Protein," J. Bacteriol. 186(3):631-637.
Van Delden et al. (1998) "Cell-to-Cell Signaling and Pseudomonas aeruginosa Infections," Emerg. Infect. Dis. 4(4):551-560.
Vannini et al. (2002) "The Crystal Structure of the Quorum Sensing Protein TraR Bound to Its Autoinducer and Target DNA," EMBO J. 21(17):4393-4401.
Von Bodman (1998) "A Negative Regulator Mediates Quorum-Sensing Control of Exopolysaccharide Production in Pantoea stewartii subsp. Stewartii," Proc. Nat. Acad. Sci. 95:7687-7692.
Wang et al. (Dec. 2008) "Inhibition of Lux Quorum-Sensing System by Synthetic N-acyi-L-Homoserine Lactone Analogous," Acta Biochimica et Biophysica Sinica. 40(12):1023-1028.
Waters et al. (2005) "Quorum Sensing: Cell-to-Cell Communication in Bacteria," Ann. Rev. Cell. Dev. Biol. 21:319-346.
Welch et al. (2005) "Cell-Cell Communication in Gram-Negative Bacteria," Molecular Biosystems. 1:196-202.
Whitehead et al. (2001) "Quorum-Sensing in Gram-Negative Bacteria," Microbial. Rev. 25(4):365-404.
Winans, S.C. (1998) "Command, Control and Communication in Bacterial Pathogenesis," Trends Microbiol. 6(10):382-383.
Yates et al. (2002) "N-Acylhomoserine Lactones Undergo Lactonolysis in a pH-, Temperature-, and Acyl Chain Length Dependent Manner During Growth of Yersinia pseudotuberculosis and Pseudomonas aeruqinosa," Infect. Immun. 70(10):5635-5646.
Zhang et al. (2002) "Structure of a Bacterial Quorum-Sensing Transcription Factor Complexed with Pheromone and DNA," Nature. 417:971-974.
Zheng et al. (2014) "Molecular Insights into How Ligands Activate or Inactivate LasR," Chemistry & Biol, 21:1261-1263.
Zhu et al. (1998) "Analogs of the Autoinducer 3-oxooctanoyi-Homoserine Lactone Strongly Inhibit Activity of the TraR Protein of Agrobacterium tumerfaciens," J. Bacterial. 180(20):5398-5405.
Zhu et al. (2001) "The Quorum-Sensing Transcriptional Regulator TraR Requires its Cognate Signaling Ligand for Protein Folding, Protease Resistance, and Dimerization," Proc. Nat. Acad. ScL USA 98(4):1507-1512.
International Search Report corresponding to International Patent Application No. PCT/US2006/003715, dated Apr. 17, 2007.
Written Opinion corresponding to International Patent Application No. PCT/US2006/003715, dated Apr. 17, 2007.
Amara, N. et al. (Jul. 2009) "Covalent Inhibition of Bacterial Quorum Sensing," J. Amer. Chem. Soc. 131(30)10610-10619.
Bassler, B. L. & Silverman M.R. (1995) "Intercellular Communication in Marine Vibrio Species: Density-Dependent Regulation of the Expression of Bioluminescence," in Two Component Signal transduction, Hoch et al. eds., Am. Soc. Microbiology Washington D.C. pp. 431-435.
Camilli, A.C. & Bassler, B.L. (Feb. 2006) "Bacterial Small-Molecule Signaling Pathways," Science, 311(5764):1113-1116.
Chhabra, S.R. et al. (Nov. 2002) "Synthetic Analogues of the Bacterial Signal (Quorum Sensing) Molecule N-(3-Oxododecanoyl)-L-homoserine Lactone as Immune Modulators." J. Med. Chem. (2003) 46, 97-104.
Galloway, W.R.J. D. et al. (2011) "Quorum Sensing in Gram-Negative Bacteria: Small-Molecule Modulation of AHL and AI-2 Quorum Sensing Pathways," Chem. Reviews, 111:28-67.
Misato, T. et al. (1974) JP 49020492 STN Abstract in English CA accession No. 1975:402237, see chemical structure (Abstract only).
Pearson, J.P., et al. (Feb. 1999) "Active Efflux and Diffusion Are Involved in Transport of Pseudomonas aeruginosa Cell-to-Cell Signals," J. Bacteriology, 181(4):1203-1210.
Williams, P., et al. (Mar. 2007) "Look who's talking: communication and quorum sensing in the bacterial world," Philosophical Transactions Royal Society B, 362:119-1134.

* cited by examiner

NON-LACTONE CARBOCYCLIC MODULATORS OF BACTERIAL QUORUM SENSING

CROSS-REFERENCE TO RELATED APPLICATIONS

This application is a continuation application of U.S. application Ser. No. 14/104,235, filed Dec. 12, 2013, which is a continuation application of U.S. application Ser. No. 12/822,929, filed Jun. 24, 2010, now U.S. Pat. No. 8,624,063, which claims the benefit of U.S. provisional application 61/222,075, filed Jun. 30, 2009, each of which is incorporated by reference herein in its entirety.

STATEMENT REGARDING GOVERNMENT FUNDING FOR RESEARCH AND DEVELOPMENT

This invention was made with government support under A1063326 awarded by the National Institutes of Health. The government has certain rights in the invention.

BACKGROUND OF THE INVENTION

Quorum sensing (QS) is a process by which bacteria assess their population density through a language of low molecular weight signalling molecules (autoinducers). Gram-negative bacteria commonly use N-acylated homoserine lactones (AHLs) as their primary autoinducers and their respective receptors (R proteins) for QS. Assessing population density allows for the modulation of gene expression levels required for group behaviour. Genes regulated by QS in *Pseudomonas aeruginosa* include virulence factor production and biofilm production. [Geske, G. D.; O'Neill, J. C.; Miller, D. M.; Mattmann, M. E.; Blackwell, H. E., Modulation of Bacterial Quorum Sensing: Systematic Evaluation of N-Acylated Homoserine Lactones in Multiple Species and New Insights into Their Mechanism of Action. *J. Am. Chem. Soc.* 2007, 129, 13613-13625.]

At high cell densities, bacteria use this chemical signaling process to switch from a nomadic existence to that of multicellular community. This lifestyle switch is significant, as numerous pathogenic bacteria use quorum sensing to turn on virulence pathways and form drug-impervious communities called biofilms that are the basis of myriad chronic infections. Over 80% of bacterial infections in humans involve the formation of biofilms, as exemplified in lung infections by *Pseudomonas aeruginosa*, which is the primary cause of morbidity in cystic fibrosis patients. The treatment of infections by pathogens that form biofilms costs over $1 billion/year in the US alone. Biofilms are dense extracellular polymeric matrices in which the bacteria embed themselves. Biofilms allow bacteria to create a microenviroment that attaches the bacteria to the host surface and which contains excreted enzymes and other factors allowing the bacteria to evade host immune responses including antibodies and cellular immune responses. Such biofilms can also exclude antibiotics. Further, biofilms can be extremely resistant to removal and disinfection. For individuals suffering from cystic fibrosis, the formation of biofilms by *P. aeruginosa* is eventually fatal. Other bacteria also respond to quorum sensing signals by producing biofilms. Biofilms are inherent in dental plaques, and are found on surgical instruments, food processing and agriculture equipment and water treatment and power generating machinery and equipment.

Gram-negative bacteria represent numerous relevant pathogens using quorum-sensing pathways. Besides *P. aeruginosa*, other quorum sensing bacteria include: *Aeromonas hydrophila, A. salmonicida, Agrobacterium tumefaciens, Burkholderia cepacia, Chromobacterium violaceum, Enterobacter agglomeran, Erwinia carotovora, E. chrysanthemi, Escherichia coli, Nitrosomas europaea, Obesumbacterium proteus, Pantoea stewartii, Pseudomonas aureofaciens, P. syringae, Ralstonia solanacearum, Rhisobium etli, R. leguminosarum, Rhodobacter sphaeroides, Serratia liguefaciens, S. marcescens, Vibrio anguillarum, V. fischeri, V. cholerae, Xenorhabdus nematophilus, Yersinia enterocolitica, Y. pestis, Y. pseudotuberculosis, Y. medievalis,* and *Y. ruckeri*. Studies on the above listed bacteria indicate that, while the AI is generally an AHL compound, the genes affected as well as the phenotypes resulting from induction of the promoter differ according to the particular life cycle of each bacterium. Further, quorum sensing stimulation typically results in altered expression of multiple genes.

*P. aeruginosa* is an opportunistic pathogen that causes severe, often fatal, infections in burn victims and cystic fibrosis patients and is therefore of direct and profound biomedical importance. *P. aeruginosa* uses 3-oxo-dodecanoyl homoserine lactone (OdDHL) as its autoinducer (Compound A):

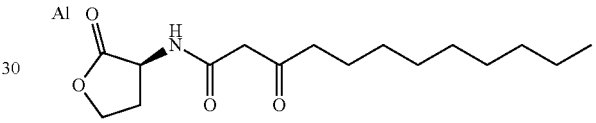

While successful modifications to the acyl tail region of autoinducers have been made, modifications to the AHL head group have met limited success. Modifications to the head group are important because the lactone ring is prone to hydrolysis at pH 7 and higher. [Glansdorp, F. G.; Thomas, G. L.; Lee, J. K.; Dutton, J. M.; Salmond, G. P. C.; Welch, M.; Spring, D. R., Synthesis and stability of small molecule probes for *Pseudomonas aeruginosa* quorum sensing modulation. *Org. Biomol. Chem.* 2004, 2, 3329-3336.] This work relates to non-homoserine lactone-based autoinducer analogs for QS modulation and provides a better understanding of the structural and electronic requirements of the autoinducer's head group. Certain of the compounds of this invention are designed as autoinducer analogs for QS modulation in *P. aeruginosa*.

Previous work in the field of *P. aeruginosa* QS modulators showed that many active non-lactone structures are highly conjugated and retain some form of the acyl chain, suggesting that a region of hydrophobicity in the acyl tail region is critical. [Muh, U.; Schuster, M.; Heim, R.; Singh, A.; Olson, E.; Greenberg, E. P., Novel *Pseudomonas aeruginosa* Quorum-Sensing Inhibitors Identified in an Ultra-High-Throughput Screen. *Antimicrob. Agents Chemother.* 2006, 50, 3674-3679; Muh, U.; Hare, B. L.; Duerkop, B. A.; Schuster, M.; Hanzelka, B. L.; Heim, R.; Olson, E. R.; Greenberg, E. P., A Structurally Unrelated Mimic of a *Pseudomonas aeruginosa* acyl-homoserine lactone quorum sensing signal. Proc. Natl. Acad. Sci. U.S.A 2006, 103, 16948-16952; Lee, L. Y. W.; Hupfield, T.; Nicholson, R. L.; Hodgkinson, J. T.; Su, X.; Thomas, G. L.; Salmond, P. C.; Welch, M.; Spring, D. R., 2-Methoxycyclopentyl analogues of a *Pseudomonas aeruginosa* quorum sensing modulator. Molecular BioSystems 2008, 4, 505-507; Eberhard, A.; Widrig, C. A.; MaBath, P.; Schineller, J. B., Analogs of the autoinducer of bioluminescence in *Vibrio fischeri*. Arch. Microbiol. 1986, 146, 35-40; Rasmussen, T. B.; Givskov, M., Quorum sensing inhibitors: a bargain of effects. Microbiology 2006, 152, 895-904; Hjelmgaard, T.; Persson, T.; Rasmussen, T. B.; Givskov, M.; Nielsen, J., Synthesis of Furanone-based natural product analogues with quorum sensing antagonist activity. Bioorg. Med. Chem. 2003, 11, 3261-3271; Smith, K. M.; Bu, Y.; Suga, H., Induction and Inhibition of *Pseudomonas aeruginosa* quorum sensing by synthetic autoinducer analogs. Chem. Biol. 2003, 10, 81-89; Schaefer, A. L.; Hanzelka, B. L.; Eberhard, A.; Greenberg, E. P., Quorum sensing in *Vibrio fischeri*: Probing autoinducer-LuxR interactions with autoinducer analogs. J. Bacteriol. 1996, 178, 2897-2901; Passador, L.; Tucker, K. D.; Guertin, K. R.; Journet, M. P.; Kende, A. S.; Iglewski, B. H., Functional analysis of the *Pseudomonas aeruginosa* Autoinducer PAI. J. Bacteriol. 1996, 178, 5995-6000; Smith, K. M.; Bu, Y.; Suga, H., Library Screening for Synthetic Agonists and Antagonists of a *Pseudomonas aeruginosa* autoinducer. Chem. Biol. 2003, 10, 563-571; Ishida, T.; Ikeda, T.; Takiguchi, N.; Kuroda, A.; Ohtake, H.; Kato, J., Inhibition of quorum sensing in *Pseudomonas aeruginosa* by N-acyl cyclopentylamides. Appl. Environ. Microbiol. 2007, 73, 3183-3188; Fletcher, M. P.; Diggle, S. P.; Crusz, S. A.; Chhabra, S. R.; Camara, M.; Williams, P., A dual biosensor for 2-alkyl-4-quinolone quorum sensing signal molecules. Environ. Microbiol. 2007, 9, 2683-2693; Kim, C.; Kim, J.; Park, H. Y.; Park, H. J.; Lee, J. H.; Kim, C. K.; Yoon, J., Furanone derivatives as quorum sensing antagonists of *Pseudomonas aeruginosa*. Appl. Microbiol. Biotechnol. 2008, 80, 37-47; Estephane, J.; Dauvergne, J.; Soulere, L.; Reverchon, S.; Queneau, Y.; Doutheau, A., N-Acyl-3-amino-5H-furanone derivatives as new inhibitors of LuxR-dependent quorum sensing: Synthesis, biological evaluation and binding mode study. Bioorg. Med. Chem. Lett. 2008, 18, 4321-4324.]

Furthermore, a close examination of the crystal structure of the N-terminal domain of LasR reveals a hydrogen bond between the 3-oxo carbonyl in the acyl tail of OdDHL and a water molecule present in the LasR binding site [Bottomley, M. J.; Muraglia, E.; Bazzo, R.; Carfi, A., Molecular insights into quorum sensing in the human pathogen *Pseudomonas aeruginosa* from the structure of the virulence regulator LasR bound to its autoinducer. *J. Biol. Chem.* 2007, 282, 13592-13600.]

Published US application US2006/0178430, published Aug. 10, 2006 and International published application WO 2008/116029, published Sep. 25, 2008 relate to quorum sensing compounds and their uses. These documents are incorporated by reference in their entirety herein for their description of the state of the art and for additional methods of synthesis, methods of testing, and methods of application of quorum sensing compounds.

Janssens, J. C. A. et al. (2007) Applied Environ. Microbiol. 73(2) 535-544 reports that certain N-acyl homoserine lactones including certain thiolactones are strong activators of SdiA, the *Salmonella enterica* Serovar *Typhimurium* LuxR homologues.

Published PCT application WO2002/052949 relates to the use of autoinducer compounds as additives to animal feeds for improving animal performance.

SUMMARY OF THE INVENTION

The invention provides a compound of formula I:

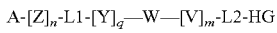

or a pharmaceutically acceptable salt or ester thereof where:
W is —NH— or

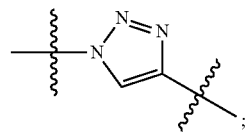 [SMILES: *c1cn(*)nn1]

Y is —CO—, —CO—CH$_2$—CO—, —NH—CO—, —CO—CH$_2$—C(Y1)-, —SO$_2$—, where Y1 is —OH, —SH, —NH$_2$ or —F;
q is 1 or 0 to indicate the presence or absence, respectively of Y;
L1 and L2, independently, are —[CH$_2$]$_{p1}$— and —[CH$_2$]$_{p2}$—, where p1 and p2, independently, are 0 or integers ranging from 1-10 and one or more of the carbons of L1 or L2 can be substituted with one or two non-hydrogen substituents;
V is

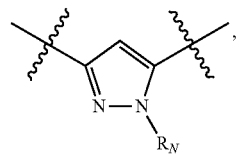

where R$_N$ is an alkyl group having 1-3 carbon atoms;
m is 1 or 0 to indicate, respectively, the presence or absence of the V group;
Z is —CO—, —O—CO—, —CO—O—, —NH—CO—, —CO—NH—, —NH—CO—NH—, —O—, —S—, or —NH$_2$—, n is 1 or 0 to indicate, respectively, the presence of absence of the Z group;
A is an aryl or heteroaryl group having one or two 5- or 6-member rings with 1-3 heteroatoms in a ring, a C$_5$-C$_8$ cycloalkyl group, a C$_5$-C$_8$ cycloalkenyl group, a heterocyclic group having one or two 5 to 8-member rings with 1-3 heteroatoms in a ring, a branched or unbranched C$_1$-C$_{12}$ acyclic aliphatic group, all of which groups can have one or more non-hydrogen substituents selected from the group consisting of halogen, nitro, hydroxyl, nitrile, azide, —R, —OR, —COOR, —OCOR, —COR, —OCOOR, —CON(R)$_2$, —OCON(R)$_2$, —N(R)$_2$, —SR, —SO$_2$R, —SOR, and —SO$_2$N(R)$_2$, wherein each R is independently selected from the group consisting of hydrogen, an amine group, a substituted or unsubstituted unbranched C$_1$-C$_{12}$ acyclic aliphatic group, a substituted or unsubstituted branched C$_1$-C$_{12}$ acyclic aliphatic group, a substituted or unsubstituted C$_3$-C$_8$ cycloalkyl group, a substituted or unsubstituted C$_3$-C$_8$ cycloalkenyl group, a fluorinated C$_1$-C$_{12}$ alkyl group, a substituted or unsubstituted aryl group, a substituted or unsubstituted heterocyclic group, and a protecting group; additionally, two R groups in the same substituent, optionally form a 4-8 member ring; and HG is a head group selected from an aryl or heteroaryl group having one or two 5- or 6-member rings with 1-3 heteroatoms in a ring; a C$_5$-C$_8$ cycloalkyl group; a $C_5$-$C_8$ cycloalkenyl group; a heterocyclic group having one or two 5 to 8-member rings with 1-3 heteroatoms in a ring; an alkyl group having 1-3 carbon atoms substituted with two aryl or heteroaryl groups; a cyclic lactone, lactam, thiolactone or ketone group having a 4-8 member ring, or an ester group $R_E$—O—CO—, where $R_E$ is an optionally substituted alkyl group having 1-6 carbon atoms; all of which groups can have one or more non-hydrogen substituents selected from the group consisting of halogen, nitro, hydroxyl, nitrile, azide, —R, —OR, —COOR, —OCOR, —COR, —OCOOR, —CON(R)$_2$, —OCON(R)$_2$, —N(R)$_2$, —SR, —SO$_2$R, —SOR, and —SO$_2$N(R)$_2$, wherein each R is independently selected from the group consisting of hydrogen, an amine group, a substituted or unsubstituted unbranched $C_1$-$C_{12}$ acyclic aliphatic group, a substituted or unsubstituted branched $C_1$-$C_{12}$ acyclic aliphatic group, a substituted or unsubstituted $C_3$-$C_8$ cycloalkyl group, a substituted or unsubstituted $C_3$-$C_8$ cycloalkenyl group, a fluorinated $C_1$-$C_{12}$ alkyl group, a substituted or unsubstituted aryl group, a substituted or unsubstituted heterocyclic group, and a protecting group; additionally, two R groups on the same substituent optionally form a 4-8 member ring.

In specific embodiments, n is 0. In specific embodiments, m is 0. In specific embodiments, n is 0 and m is 0. In specific embodiments, n is 0 and q is 1. In specific embodiments, n is 0, m is 0 and q is 1. In specific embodiments, n is 0, m is 1 and q is 1. In specific embodiments, n is 1, m is 1 and q is 1.

In a specific embodiment, W is —NH—.

In an embodiment, HG is a group having formula:

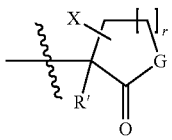

where r is an integer ranging from 1-4, G is —O—, —S—, —NH— or —CH$_2$—; R' is hydrogen or a 1-6 carbon aliphatic group, particularly an alkyl group, and X represents optional substitution with one or more non-hydrogen substituents on one or more ring carbons. In specific embodiments, r is 1 or 2, the ring is unsubstituted and R' is H.

In a specific embodiment, G is —S—. In a specific embodiment, G is —S— and r is 1. In a specific embodiment, G is —S—, r is 1 and R' is an alkyl group. In a specific embodiment, G is —S—, r is 1 and R' is an alkyl group. X represents 1, or 2 substituents on the ring.

In an embodiment, HG is a group other than a ketone, lactone, or lactam group, when W is —NH—.

In an embodiment, HG is selected from an optionally substituted phenyl, naphthyl, cyclohexyl, cyclohexenyl, cyclopentyl, pyridyl, piperidyl, furyl, thienyl, pyrroyl, or

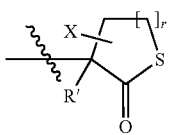

where r is an integer ranging from 1-4, R' is hydrogen or a 1-6 carbon aliphatic group, particularly an alkyl group, and X represents optional substitution with one or more non-hydrogen substituents on one or more ring carbons. In specific embodiments, r is 1, the ring is unsubstituted and R' is H. In specific embodiments, r is 1, and R' is an alkyl group, particularly a methyl group. In specific embodiments, r is 1, R' is an alkyl group, particularly a methyl group and X represents 1, or 2 substituents on the ring.

In specific embodiments, when HG is an unsubstituted thiolactone ring (where G is S and all X and R' are hydrogen) and W is —NH—, A is a group other than an unsubstituted alkyl group or a halogenated alkyl group. In specific embodiments, when HG is an unsubstituted thiolactone ring (where G is S and all X and R' are hydrogen); W is —NH—, q is 1 and Y is —COCH$_2$—CO—, A is a group other than an unsubstituted alkyl group or a halogenated alkyl group. In specific embodiments, when HG is an unsubstituted thiolactone ring (where G is S and all X and R' are hydrogen); W is —NH—; m, n, p1 and p2 are all 0; q is 1 and Y is —CO—CH$_2$—CO—, A is a group other than an unsubstituted alkyl group or a halogenated alkyl group.

In specific embodiments, HG is a group as illustrated in FIG. 1-1, or 1-2, where X, X1 and X2, represent optional substitution with one or more non-hydrogen substituents on one or more ring carbons. In these Figures X, X1 and X2 represents optional substitution with one or more non-hydrogen substituents on one or more ring carbons, RA is H or an alkyl group, particularly one having 1-3 carbon atoms. In more specific embodiments, HG is selected from groups HG1, HG4, HG7, HG8, HG10, HG11, or HG12. In other specific embodiments, HG is selected from groups HG2, HG3, HG14, HG15, HG17, HG18 or HG21. In specific embodiments, HG is a group of any of FIG. 2-1, 2-2, or 2-3. In these Figures X, X1-X5 represents optional substitution with one or more non-hydrogen substituents on one or more ring carbons and R' is an alkyl group having 1-6 or 1-3 carbon atoms.

In specific embodiments HG is an ester group $R_E$—O—CO, where $R_E$ is an unsubstituted alkyl group having 1-6 carbon atoms; an alkyl group substituted with one or more halogens, particularly fluorines; a phenyl group or optionally substituted phenyl group, particular a phenyl group substituted with one or more halogens, particularly fluorine, one or more nitro groups, one or more alkoxy groups (including 1C-3C alkoxy groups), or one or more trifluoromethyl groups. In specific embodiments, $R_E$ is methyl, ethyl, propyl or butyl groups. In more specific embodiments, $R_E$ is a methyl or ethyl group. In specific embodiments when HG is an ester group L2 is —CH(CH$_3$)—.

In specific embodiments, HG is a group as illustrated in FIG. 1-1, 1-2, 2-1, 2-2, or 2-3, and A is a branched or unbranched aliphatic group having 1-12 carbon atoms and more specifically is an alkyl or alkenyl group having 1-12 carbon atoms. In specific embodiments HG is a group as illustrated in FIG. 2-1, 2-2, or 2-3.

In specific embodiments, A is a group as in FIG. 3, where X represents optional substitution with one or more non-hydrogen substituents on one or more ring carbons or on a specific ring carbon, R' is an alkyl group, particularly one having 1-6 or 1-3 carbon atoms. In specific embodiments, HG is a group as in FIG. 1-1, 1-2, 1-3, 2-1, 2-2, or 2-3 and A is a group in FIG. 3. In specific embodiments, HG is a group as in FIG. 1-1, 1-2, 1-3, 2-1, 2-2, or 2-3 and A is a group in FIG. 3 and W is

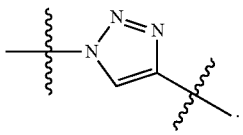 [SMILES: *c1cn(*)nn1]

In specific embodiments, A is one of A1-A13 (FIG. 3-1). In specific embodiments, A is one of A1-A13 (FIG. 3-1) and n is 0. In specific embodiments, A is one of A1-A13 (FIG. 3-1), n is 0, q is 1 and Y is —CO— or —CO—CH$_2$—CO—. In specific embodiments, A is one of A1-A13 (FIG. 3-1), n is 0, q is 1, Y is —CO— or —CO—CH$_2$—CO—, and W is —NH—. In specific embodiments, A is one of A1-A13 (FIG. 3-1), n is 0, q is 1, Y is —CO— or —CO—CH$_2$—CO—, and W is

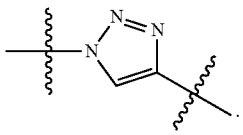

In specific embodiments, A is one of A1-A13 (FIG. 3), n is 0, q is 1, Y is —CO— or —CO—CH$_2$—CO—, W is —NH— and m is 0. In specific embodiments, A is one of A1-A13 (FIG. 3), n is 0, q is 1, Y is —CO— or —CO—CH$_2$—CO—, W is —NH— and m is 1.

In specific embodiments, A is a branched or straight chain alkyl or alkenyl group. In specific embodiments, A is a branched or straight chain alkyl or alkenyl and n is 0. In specific embodiments, A is a branched or straight chain alkyl or alkenyl, n is 0, q is 1 and Y is —CO— or —CO—CH$_2$—CO—. In specific embodiments, A is a branched or straight chain alkyl or alkenyl, n is 0, q is 1, Y is —CO— or —CO—CH$_2$—CO— and W is —NH—. In specific embodiments, A is a branched or straight chain alkyl or alkenyl, n is 0, q is 1, Y is —CO— or —CO—CH$_2$—CO—, and W is

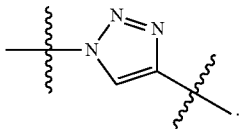 [SMILES: *c1cn(*)nn1]

In specific embodiments, A is a branched or straight chain alkyl or alkenyl, n is 0, q is 1, Y is —CO— or —CO—CH$_2$—CO—, W is —NH— and m is 0. In specific embodiments, A is a branched or straight chain alkyl or alkenyl n is 0, q is 1, Y is —CO— or —CO—CH$_2$—CO—, W is —NH— and m is 1.

In specific embodiments, HG is a group as in FIG. 1-1, 1-2, 2-1, 2-2, or 2-3 and W is NH and m is 1. In specific embodiments, HG is a group as in FIG. 1-1, 1-2, 2-1, 2-2, or 2-3, L1 is —CH$_2$— or —CH$_2$—CH$_2$—, L2 is —(CH$_2$)$_{0-1}$— and q is 1. In specific embodiments, HG is a group as in FIG. 1-1, 1-2, 2-1, 2-2, or 2-3, L1 is —CH$_2$— or —CH$_2$—CH$_2$—, L2 is —(CH$_2$)$_{0-1}$— and q is 1 and Y is —CO— or —CO—CH$_2$—CO—. In specific embodiments, HG is a group as in FIG. 1-1, 1-2, 2-1, 2-2, or 2-3, and L1 is —CH$_2$— or —CH$_2$—CH$_2$—, L2 is —(CH$_2$)$_{0-1}$— and q is 1 and Y is —CO—.

In specific embodiments, HG is a group as in FIG. 1-1, 1-2, 2-1, 2-2, or 2-3 and A is a branched or straight chain alkyl or alkenyl and W is —NH— and m is 1. In specific embodiments, HG is a group as in FIG. 1-1, 1-2, 2-1, 2-2, or 2-3 and A is a branched or straight chain alkyl or alkenyl, L1 is —CH$_2$— or —CH$_2$—CH$_2$—, L2 is —(CH$_2$)$_{0-1}$— and q is 1. In specific embodiments, HG is a group as in FIG. 1-1, 1-2, 2-1, 2-2, or 2-3 and A is a branched or straight chain alkyl or alkenyl, L1 is —CH$_2$— or —CH$_2$—CH$_2$—, L2 is —(CH$_2$)$_{0-1}$— and q is 1 and Y is —CO— or —CO—CH$_2$—CO—. In specific embodiments, HG is a group as in FIG. 1-1, 1-2, 2-1, 2-2, or 2-3 and A is a branched or straight chain alkyl or alkenyl, and L1 is —CH$_2$— or —CH$_2$—CH$_2$-L2 is —(CH$_2$)$_{0-1}$— and q is 1 and Y is —CO—.

In specific embodiments, HG is a group as in FIG. 1-1, 1-2, 2-1, 2-2, or 2-3 and A is a group in FIG. 3-1 and W is NH and m is 1. In specific embodiments, HG is a group as in FIG. 1-1, 1-2, 2-1, 2-2, or 2-3 and A is a group in FIG. 3, L1 is —CH$_2$— or —CH$_2$—CH$_2$—, L2 is —(CH$_2$)$_{0-1}$— and q is 1. In specific embodiments, HG is a group as in FIG. 1-1, 1-2, 2-1, 2-2, or 2-3 and A is a group in FIG. 3, L1 is —CH$_2$— or —CH$_2$—CH$_2$—, L2 is —(CH$_2$)$_{0-1}$— and q is 1 and Y is —CO— or —CO—CH$_2$—CO—. In specific embodiments, HG is a group as in FIG. 1-1, 1-2, 2-1, 2-2, or 2-3 and A is a group in FIG. 3, with the exception that A is not the same group as HG and L1 is —CH$_2$— or —CH$_2$—CH$_2$—, L2 is —(CH$_2$)$_{0-1}$— and q is 1 and Y is —CO—.

In specific embodiments, HG is a group as in FIG. 1-1, 1-2, 1-3, 2-1, 2-2, or 2-3 and A is a group in FIG. 3-1 with the exception that A is not the same group as HG.

In specific embodiments, HG is P1-P50. In specific embodiments, HG is P1-P50 and L2 is —(CH$_2$)$_{0-2}$— and may be substituted on one carbon with an alkyl group having 1-3 carbon atoms. In specific embodiments, HG is P1-P50; L2 is —(CH$_2$)$_{0-2}$— and is optionally substituted on one carbon with an alkyl group having 1-3 carbon atoms, and m is 0. In specific embodiments, HG is P1-P50; L2 is —(CH$_2$)$_{0-2}$— and may be substituted on one carbon with an alkyl group having 1-3 carbon atoms, and m is 1. In specific embodiments, HG is P1-P50; L2 is —(CH$_2$)$_{0-2}$— and may be substituted on one carbon with an alkyl group having 1-3 carbon atoms, and m is 1 and W is NH. In specific embodiments, HG is P1-P50; L2 is —(CH$_2$)$_{0-2}$— and may be substituted on one carbon with an alkyl group having 1-3 carbon atoms, and m is 1, W is NH and q is 1. In specific embodiments, HG is P1-P50; L2 is —(CH$_2$)$_{0-2}$— and may be substituted on one carbon with an alkyl group having 1-3 carbon atoms, and m is 1, W is —NH—, q is 1 and Y is —CO— or —CO—CH$_2$—CO—. In specific embodiments HG is P1-P50 and L1 is —(CH$_2$)$_{0-2}$—. In specific embodiments HG is P1-P50 and n is 0.

HG groups may be unsubstituted. HG groups may be substituted. Optional substitution on HG groups includes substitution with one or more non-hydrogen substituents selected from the group consisting of halogen, nitro, hydroxyl, nitrile, azide, —R, —OR, —COOR, —OCOR, —COR, —OCOOR, —CON(R)$_2$, —OCON(R)$_2$, —N(R)$_2$, —SR, —SO$_2$R, —SOR, —SO$_2$N(R)$_2$, wherein each R is independently selected from the group consisting of hydrogen, an amine group, a substituted or unsubstituted unbranched C1-C12 acyclic aliphatic group, a substituted or unsubstituted branched C1-C12 acyclic aliphatic group, a substituted or unsubstituted C3-C8 cycloalkyl group, a substituted or unsubstituted C3-C8 cycloalkenyl group, a fluorinated C1-C12 alkyl group, a substituted or unsubstituted aryl group, a substituted or unsubstituted heterocyclic group, and a protecting group, where two R groups on the same substituent optionally form a 4-8 member ring (carbon ring or a carbon ring with 1-3 heteroatom ring members); additionally, two X, X1 or X2 groups, particularly two such groups on adjacent ring positions can form a 4-8 member ring. Specific substituents include among others optionally substituted alkyl groups having 1-3 carbon atoms.

In specific embodiments, X, X1 or X2 represent one or more halogens, nitro, azide, nitrile, alkyl groups particularly those having 1-3 carbon atoms, —OR, —COOR, —SO$_2$—R, —SR, or —N(R)$_2$, particularly where R is hydrogen or an alkyl group having 1-3 carbon atoms.

In specific embodiments, one or more carbons of L1 can be substituted with an alkyl group having 1-3 carbon atoms, a hydroxyl or amine group or a halogen, particularly a fluorine. In a more specific embodiment one carbon of L1 can be substituted with one non-hydrogen substituent. In a specific embodiment L1 is —CH(R')— where R' is an alkyl group. In a specific embodiment L1 is —(CF$_2$)$_{p1}$—.

In specific embodiments, one or more carbons of L2 can be substituted with an alkyl group having 1-3 carbon atoms, a hydroxyl or amine group or a halogen, particularly a fluorine. In a more specific embodiment one carbon of L2 can be substituted with one non-hydrogen substituent. In a specific embodiment L2 is —CH(R')— where R' is an alkyl group. In a specific embodiment L2 is —(CF$_2$)$_{p1}$—.

The invention also provides a compound of formula II:

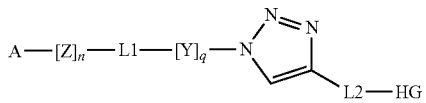

or a pharmaceutically acceptable salt or ester thereof where variables are defined as for formula I. In an embodiment, q is 0. In an embodiment q is 1. In an embodiment, q is 1 and Y is and Y is —CO—, —CO—CH$_2$—CO— or —CO—CH$_2$—C(Y1)-.

In embodiments of formula II, A is a branched or unbranched C1-C12 acyclic aliphatic group. More specifically A is a branched or unbranched alkyl or alkenyl group having 1-15 carbon atoms. In more specific embodiments of formula II where A is a branched or unbranched C1-C12 acyclic aliphatic group, n is 0, q is 0 and L1 is —(CH$_2$)$_{p1}$—, where p1 is 0-6. In additional specific embodiments of formula II where A is a branched or unbranched C1-C12 acyclic aliphatic group, n is 0, q is 1, Y is —CO— or —CO—CH$_2$—C(Y1)-, L1 is —(CH$_2$)$_{p1}$—, where p1 is 0-6. In more specific embodiments, A is a branched or unbranched alkyl group having 1-12 carbon atoms.

In embodiments of formula II, A is an optionally substituted aryl group. In more specific embodiments, q is 0, L1 is —(CH$_2$)$_p$— where p is 0-6 and A is an optionally substituted aryl group, particularly an optionally substituted phenyl, biphenyl or naphthyl group. In additional specific embodiments, q is 0, L1 is —(CH$_2$)$_p$—, where p is 1-3, and A is an optionally substituted aryl group, particularly an optionally substituted phenyl, biphenyl or naphthyl group. In additional embodiments, the phenyl, biphenyl or naphthyl group is unsubstituted or substituted with one or more halide, nitro, hydroxyl, nitrile, azide, —OR, —N(R)$_2$, —SR, or —SO$_2$R groups, where R is an alkyl group having 1-3 carbon atoms.

In embodiments of formula II, HG is an optionally substituted phenyl, naphthyl, cyclopentyl, cyclohexyl, cyclohexenyl, furyl, or group having formula:

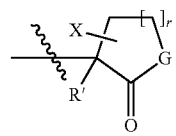

where variables are as defined above and in specific embodiments, r is 1 or 2. In additional embodiments, the ring is unsubstituted and R' is hydrogen. In additional embodiments, R' is an alkyl group having 1-3 carbon atoms. In additional embodiments, the ring carries 1-3 substituents, particularly optionally substituted alkyl groups having 1-3 carbon atoms. Preferred optional substitution for phenyl, naphthyl, cyclopentyl, cyclohexyl, or cyclohexenyl HG groups is one or more halogen, nitro, or alkoxy (having 1-3 carbon atoms). In specific embodiments, HG is:

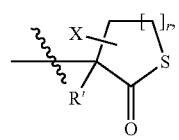

where r, X and R' are as defined above. In specific embodiments, r is 1. IN specific embodiments, R' is H. In specific embodiments, R' is optionally substituted C1-C3 alkyl. In specific embodiments, X is 1-3 substituents on the ring. In specific embodiments, r is 1 and X is 1 or 2 substituents on the ring. In specific embodiments, X is 1 or 2 optionally substituted alkyl groups having 1-3 carbon atoms.

Compounds of this invention can be optically active, racemic, enantiomerically pure or mixtures of enantiomers. HG may have optically active carbons and may exist as enantiomeric pairs. For example, HG of formula:

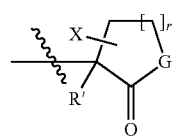

can be in the enantiomeric forms:

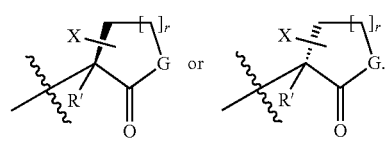

Note that carbons in the HG ring other than that shown may be optically active dependent upon X substitution.

The invention also provides a compound of formula III:

or a pharmaceutically acceptable salt or ester thereof, where variables are defined as for formula I. In specific embodiments of formula III, m is 0. In other specific embodiments, n is 0. In other specific embodiments, m and n are both 0. In specific embodiments, m is 0 and q is 1. In more specific embodiments, m is 0, q is 1 and Y is —CO—, —CO—CH$_2$—CO— or —CO—CH$_2$—C(Y1)-. In more specific embodiments, m is 0, q is 1 and Y is —CO—, —CO—CH₂—CO— or —CO—CH₂—C(Y1)-, and A is an optionally substituted aryl group, particularly an optionally substituted phenyl group. In more specific embodiments, m is 0, q is 1 and Y is —CO—, —CO—CH₂—CO— or —CO—CH₂—C(Y1)-, and A is an optionally substituted branched or unbranched C₁-C₁₂ acyclic aliphatic group. In specific embodiments HG is a group of any of FIG. 1-1, 1-2, 1-3, 2-1, 2-2 or 2-3. In specific embodiments, HG is:

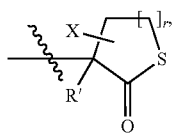

where r, X and R' are as defined above. In specific embodiments, r is 1. In specific embodiments, R' is H. In specific embodiments, R' is optionally substituted C1-C3 alkyl. In specific embodiments, X is 1-3 substituents on the ring. In specific embodiments, r is 1 and X is 1 or 2 substituents on the ring. In specific embodiments, X is 1 or 2 optionally substituted alkyl groups having 1-3 carbon atoms.

The invention also provides a compound of formula IV:

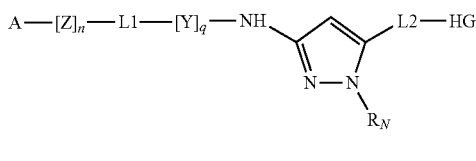

or a pharmaceutically acceptable salt or ester thereof, where variables are defined as for formula I. In specific embodiments, $R_N$ is hydrogen. In specific embodiments, q is 1 and Y is —CO—, —CO—CH₂—CO— or —CO—CH₂—C(Y1)-. In specific embodiments, HG is an optionally substituted aryl group, particularly an optionally substituted phenyl group. In specific embodiments, A is A is an optionally substituted aryl group, particularly an optionally substituted phenyl group. In specific embodiments, A is an optionally substituted branched or unbranched C₁-C₁₂ acyclic aliphatic group, particularly an optionally substituted branched or unbranched alkyl or alkenyl group having 1 to 12 carbon atoms. In specific embodiments HG is a group of any of FIG. 1-1, 1-2, 2-1, 2-2 or 2-3. In specific embodiments, HG is:

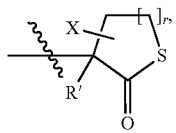

where r, X and R' are as defined above. In specific embodiments, r is 1. IN specific embodiments, R' is H. In specific embodiments, R' is optionally substituted C1-C3 alkyl. In specific embodiments, X is 1-3 substituents on the ring. In specific embodiments, r is 1 and X is 1 or 2 substituents on the ring. In specific embodiments, X is 1 or 2 optionally substituted alkyl groups having 1-3 carbon atoms.

The invention also provides a compound of formula V:

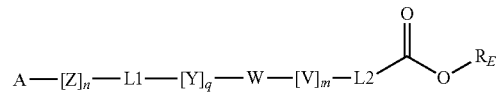

or a pharmaceutically acceptable salt or ester thereof, where variables are defined as for formula I. In specific embodiments, $R_E$ is an unsubstituted alkyl group having 1-6 carbon atoms. In specific embodiments, $R_E$ is methyl or ethyl. In specific embodiments, A is a branched or straight-chain aliphatic group having 1-12 carbon atoms. In specific embodiments, A is a branched or straight-chain alkyl group having 1-12 carbon atoms. In specific embodiments, A is an optionally substituted phenyl group. In specific embodiments, A is a phenyl group substituted with one or more halogens, nitro groups, alkoxy groups having 1-3 carbon atoms, or one or more trifluoroethyl groups. In specific embodiments W is —NH—. In specific embodiments L1 and L2 are independently either —CH₂— or —CH₂—CH₂—. In a specific embodiment L2 is —CH(CH₃)—. In specific embodiments, Y is —CO—, —CO—CH₂—CO—, —NH—CO—, —CO—CH₂—C(Y1)-. In specific embodiments, Y is —CO—, or —CO—CH₂—CO. In specific embodiments, q is 1. In specific embodiments, n is 0. In specific embodiments, m is 0. In specific embodiments, n and m are 0 and q is 1. In specific embodiments Y is —CO— or —CO—CH₂—CO—.

The invention also provides a compound of formula VI:

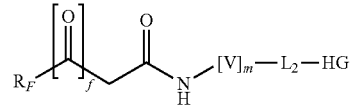

where $R_F$ is an optionally substituted a branched or unbranched C₁-C₁₂ acyclic aliphatic group, L2, V and m are as defined above, f is 0 or 1 to show the absence of presence of the CO group, and HG is a head group as defined in formula I. In specific embodiments, m is 0. In specific embodiments m is 1. In specific embodiments L2 is —CH₂— or —CH₂—CH₂—. In specific embodiments, HG can be any group as in FIG. 1-1, 1-2 or 1-3. In other embodiments, HG is an optionally substituted phenyl group. In specific embodiments, L2 is —CH₂— and HG is an optionally substituted phenyl group. In specific embodiments, m is 1, L2 is —CH₂— and HG is an optionally substituted phenyl group. In specific embodiments, m is 0, L2 is —CH₂— and HG is an optionally substituted phenyl group. In specific embodiments $R_F$ is a branched or straight-chain alkyl group. In specific embodiments $R_F$ is a branched or straight-chain alkenyl group having one or two double bonds. In specific embodiments, f is 1 and m is 0. In specific embodiments, f is 0 and m is 0. In specific embodiments, f and m are both 1. In specific embodiments, f is 0 and m is 1. In specific embodiments, HG is a phenyl group substituted with 1 to 5 halogens, particularly bromine, chlorine or fluorine. In specific embodiments, HG is a phenyl group substituted with 1 to 5 fluorines. In specific embodiments, HG is a phenyl group substituted with 1 or 2 alkoxy groups having 1-3 carbon atoms. In specific embodiments, HG is a phenyl group substituted with 1-3 nitro groups. In specific embodiments, HG is a furyl group, particularly a 1-furyl group. In specific embodiments, m is 1, f is 1, L2 is —CH₂— or —CH₂—CH₂— and HG is selected from HG groups of FIG. 1-1, 1-2, 1-3, 2-1, 2-2, 2-3 or 2-4. In specific embodiments, m is 1, f is 0, L2 is —CH$_2$— or —CH$_2$—CH$_2$— and HG is selected from HG groups of 1-1, 1-2, 1-3, 2-1, 2-2, 2-3 or 2-4. In specific embodiments, m is 0, L2 is —CH$_2$— or —CH$_2$—CH$_2$— and HG is selected from HG groups of FIG. 1-1, 1-2, 1-3, 2-1, 2-2 or 2-3. In specific embodiments, m is 0, f is 1, L2 is —CH$_2$— or —CH$_2$—CH$_2$— and HG is selected from HG groups of FIG. 11-1, 1-2, 1-3, 2-1, 2-2, 2-3 or 2-4. In specific embodiments, m is 0, f is 0, L2 is —CH$_2$— or —CH$_2$—CH$_2$— and HG is selected from HG groups of FIG. 1-1, 1-2, 1-3, 2-1, 2-2, 2-3 or 2-4. In specific embodiments, HG is:

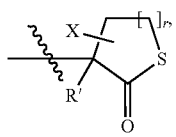

where r, X and R' are as defined above. In specific embodiments, r is 1. In specific embodiments, R' is H. In specific embodiments, R' is optionally substituted C1-C3 alkyl. In specific embodiments, X is 1-3 substituents on the ring. In specific embodiments, r is 1 and X is 1 or 2 substituents on the ring. In specific embodiments, X is 1 or 2 optionally substituted alkyl groups having 1-3 carbon atoms.

The present invention provides compounds and methods for modulation of quorum sensing of bacteria. In an embodiment, the compounds of the present invention are able to act as replacements for naturally occurring bacterial quorum sensing ligands in a ligand-protein binding system; that is, they imitate the effect of natural ligands and produce an agonistic effect. In another embodiment, the compounds of the present invention are able to act in a manner which disturbs or inhibits the naturally occurring ligand-protein binding system in quorum sensing bacteria; that is, they produce an antagonistic effect. The present invention also provides methods of increasing or reducing the virulence of quorum sensing bacteria. In one aspect, the method comprises contacting a bacterium with an effective amount of a compound of the present invention. In another aspect, the method comprises contacting a bacterium with a therapeutically effective amount of a pharmaceutically acceptable salt or ester of the compounds of the present invention. In yet another aspect, the method comprises contacting a bacterium with a precursor which can form an effective amount of a compound of the present invention.

The present invention provides compositions for modulation of quorum sensing of bacteria which comprises one or more compounds of this invention, particularly one or more compounds of formulas I to VI herein. The compositions herein can further comprise an appropriate carrier, particularly a pharmaceutically acceptable carrier for therapeutic applications. In applications herein, one or more compounds of the invention can be compounds with one or more antibacterial compounds.

In an embodiment, the methods of the present invention can be used for disrupting a biofilm formed by a quorum sensing bacterium. A method of the present invention for disrupting a biofilm comprises contacting the biofilm with an effective amount of a compound of the present invention. In an embodiment, the methods of the present invention can be used to diminish or inhibit biofilm production. Alternatively, the methods of the present invention can be used for causing a quorum sensing bacterium to initiate or enhance biofilm production. Initiation or enhancement of biofilm formation of beneficial bacteria (those, for example, that provide a health benefit or are used in production of a valuable product) can facilitate or enhance such a health benefit or can be used to enhance or improve production of desirable valuable products. In a specific embodiment, compounds which activate quorum sensing of beneficial gut bacterial can provide a probiotic effect.

In an embodiment, the methods of the present invention can be used for inhibiting or diminishing the symbiotic behavior of a quorum sensing bacteria. In another embodiment, the methods of the present invention can be used for stimulating, initiating, or enhancing the symbiotic behavior of a quorum sensing bacteria.

In another embodiment of the methods, the compounds of the present invention can be administered to a subject to initiate modulation of quorum sensing of bacteria. In an embodiment, the administration of an effective amount of a compound of the present invention to a subject can initiate or enhance the symbiotic behavior of quorum sensing bacteria in the subject. In an embodiment, the administration of an effective amount of a compound of the present invention to a subject can disrupt a biofilm of quorum sensing bacteria in the subject. In an embodiment, the administration of an effective amount of a compound of the present invention to a subject can initiate or enhance the symbiotic behavior of a target species or a selected strain of a target species of quorum sensing bacteria in the subject. In an embodiment, the administration of an effective amount of a compound of the present invention to a subject can regulate the virulence of quorum sensing bacteria in the subject. In an embodiment, the administration of an effective amount of a compound of the present invention to a subject can regulate the virulence of a target species or a selected strain of a target species of quorum sensing bacteria in the subject.

The methods of the present invention also provide for regulation of the level of virulence of quorum sensing bacteria. In an embodiment, one or more compounds of the present invention is brought into contact with a quorum sensing bacteria to selectively regulate the virulence of the bacteria. In an embodiment, a mixture of the compounds of the present invention is brought into contact with a quorum sensing bacteria to selectively regulate the virulence of the bacteria. The amount of each compound in the mixture is that amount effective to achieve a desired effect on regulation of virulence. The methods of the present invention also provide for regulation of the production of a biofilm by quorum sensing bacteria. In an embodiment, one or more compounds of the present invention is brought into contact with a quorum sensing bacteria or bacterial biofilm to selectively regulate the biofilm production by the bacteria. In an embodiment, a mixture of the compounds of the present invention is brought into contact with a quorum sensing bacteria or bacterial biofilm to selectively regulate the biofilm production by the bacteria. The amount of each compound in the mixture is that amount effective for desired regulation of biofilm formation.

The methods of the present invention also provide for regulation of the virulence, biofilm production, or symbiotic behavior of a quorum sensing bacteria by contacting the bacteria with a photoactive compound and illuminating the bacteria and photoactive compound. In an embodiment, illuminating a photoactive compound of the present invention can change the agonistic or antagonistic behavior of the compound.

In an embodiment, the present invention provides a surface coating or polymer having incorporated therein a compound of the present invention. The amount of compound or polymer in the surface coating is that sufficient to provide antimicrobial or antifouling effect. In an embodiment, the compounds of the present invention are useful as an antimicrobial and/or antifouling agent. Compounds of the present invention are further useful in a medical, scientific, and/or biological application. In one aspect, the present invention provides a composition comprising one or more compounds of the present invention and a carrier or diluent. In a preferred embodiment, the carrier or diluent comprises a liquid. Such a liquid may comprises an aqueous solvent or a non-aqueous solvent. An exemplary solvent comprises one or more organic solvents. The carrier or diluent may also comprise an ionic liquid. In an embodiment of this aspect, the composition comprises an organic or inorganic polymeric substance. The polymeric substance may comprise one or more compounds of the present invention, admixed with a polymer, bound to a polymer, or adsorbed on to a polymer. In an exemplary embodiment of this aspect, the composition is in the form of a solution or suspension of said at least one compounds of the present invention, preferably in an aerosol or powder formulation.

In an embodiment of this aspect, the composition is formulated as a disinfectant or cleaning formulation. In another embodiment, the composition is in the form of a powder, a solution, a suspension, a dispersion, an emulsion, or a gel. In an exemplary embodiment, the composition is in the form of a pharmaceutical composition comprising a pharmaceutically acceptable carrier, diluent, and/or excipient and one or more compounds of the present invention. The composition may be in a form suitable for parenteral or non-parenteral administration. A preferred composition may be formulated for topical, intradermal, intramuscular, intraperitoneal, intravenous, subcutaneous, intranasal, epidural, ophthalmic, or oral administration. In an embodiment of this aspect the composition is formulated for administration by infusion or bolus injection, absorption through epithelial or mucocutanous linings and may be administered together with other biologically active agents. In an embodiment, the composition may further be formulated for use in an inhaler or nebulizer.

In another aspect, the present invention provides a method of treating an infection in a human or animal subject, the method comprising administration to the subject of an effective amount of one or more compounds of the present invention. In an embodiment, the treatment is therapeutic or prophylactic. In an embodiment, the method further comprises administering one or more pharmaceutically acceptable antibacterial compounds to the subject, prior to, at the same time as or after administration of the one or more compounds of this invention.

In a related embodiment, the present invention provides a method of treating an infection or condition in a subject that is characterized by biofilm formation, the method comprising administering one or more compounds of the present invention. In an embodiment, the method further comprises administering one or more pharmaceutically acceptable antibacterial compounds to the subject, prior to, at the same time as or after administration of the one or more compounds of this invention. In an embodiment, the condition is cystic fibrosis. In an embodiment, the condition is dental caries, periodonitis, otitis media, muscular skeletal infections, necrotizing fasciitis, biliary tract infection, osteomyelitis, bacterial prostatitis, native valve endocarditis, cystic fibrosis pneumonia, or meloidosis. In an embodiment, the condition is a nosocomial infection; preferably the infection is ICU pneumonia or an infection associated with sutures, exit sites, arteriovenous sites, scleral buckles, contact lenses, urinary catheter cystitis, peritoneal dialysis (CAPD) peritonitis, IUDs, endotracheal tubes, Hickman catheters, central venous catheters, mechanical heart valves, vascular grafts, biliary stent blockage, orthopedic devices, or penile prostheses. In an embodiment, the infection is a skin infection, a burn infection, or a wound infection. According to this aspect, the subject may preferably be an immunocompromised individual.

The present invention further provides a method for treating or preventing biofilm formation on a surface, the method comprising contacting said surface with one or more compounds in an amount effective for affecting biofilm formation of the present invention. In an embodiment, the method further comprises contacting the surface with one or more antibacterial compounds appropriate for the application, prior to, at the same time as or after contact with the one or more compounds of this invention. In an embodiment, the surface is a non-biological surface. In an embodiment, the surface is a natural surface. In an embodiment, the surface is a surface of a plant, seed, wood, fiber or hair. In an embodiment, the surface is a biological surface; preferably the surface is a surface of a tissue, membrane, or skin. In an embodiment, the surface is a hard surface; preferably the surface comprises a metal, an organic polymer, an inorganic polymer, a natural elastomer, a synthetic elastomer, glass, wood, paper, concrete, rock, marble, gypsum, or ceramic. In an embodiment, the said surface is coated or wherein the surface is a coating; in a preferred embodiment, the coating comprises enamel, varnish, or paint.

In an embodiment of this aspect, the surface is a soft surface, and may be the surface of a fiber comprising a yarn, a textile, a vegetable fiber, or rock wool. In another embodiment, the surface is a porous surface. In an embodiment, the surface is a surface of process equipment or components of cooling equipment. In a preferred embodiment, the process equipment is or is a component of a cooling tower, a water treatment plant, a dairy processing plant, a food processing plant, a chemical process plant, or a pharmaceutical process plant. In a preferred embodiment the surface is that of a filter or a membrane filter.

In an embodiment of this aspect, the surface is a surface of a toilet bowl, a bathtub, a drain, a high-chair, a counter top, a vegetable, a meat processing room, a butcher shop, food preparation areas, an air duct, an air-conditioner, a carpet, paper or woven product treatment, a diaper, personal hygiene products and a washing machine. In another embodiment, the surface is an industrial surface or a medical surface; preferably the surface is a surface in a hospital, a veterinary hospital, a mortuary, or a funeral parlor.

In another aspect, the compounds of the present invention are useful as a component of a dentifrice, a mouthwash, or a composition for the treatment of dental caries; for treatment of acne; or for cleaning and/or disinfecting contact lenses. The compounds of the present invention are further useful for incorporation into the surface of a medical device or an implant device. Preferably the implant device is an artificial heart valve, hip joint, an indwelling catheter, pacemaker, or surgical pin. The compounds of the present invention are further useful as an antifouling coating. The present invention further provides an optical lens, wherein at least a part of a surface of the lens is associated with one or more compounds of the present invention. Preferably, the optical lens is a contact lens.

In another aspect, the present invention provides a biofilm removing or inhibiting composition comprising one or more compounds of the present invention in an amount effective for removing or inhibiting biofilm formation and a vehicle or carrier, wherein the amount of the mixture is effective to remove or disrupt a bacterial biofilm or inhibit normal biofilm formation. An embodiment of this aspect may further comprise a surfactant selected from the group consisting of an anionic surfactant, a nonionic surfactant, an amphoteric surfactant, a biological surfactant, and any combination of these; or a compound selected from the group consisting of an antibacterial which includes among others a biocide, a fungicide, an antibiotic, and any combination of these.

In another aspect, the present invention provides a method of removing a biofilm from a surface, the method comprising the step of administering a cleaning-effective amount of one or more compounds of the present invention to a biofilm-containing surface. A preferred method of this aspect comprises the step of administering an effective amount of one or more compounds of the present invention to the surface, wherein the amount is effective to prevent biofilm formation. Such a surface may be a hard or rigid surface or a surface selected from the group consisting of glazed ceramic, porcelain, glass, metal, wood, chrome, plastic, vinyl, composite materials (such as Formica® (Formica Corporation, Cincinnatti, Ohio), and the surface of a drainpipe. In an embodiment, the surface is a soft or flexible surface, or the surface is selected from the group consisting of a shower curtain or liner, upholstery, laundry, clothing, and carpeting. In an embodiment, the surface is a biological surface and the effective amount is a therapeutically effective amount for application to the biological surface for inhibiting biofilm formation. The compounds of the present invention are useful in particular, for removing or disrupting a biofilm produced by a bacterium of the class *Pseudomonas*, a bacterium is of the species *Pseudomonas aeruginosa*, or an organism selected from the group consisting of bacteria, algae, fungi and protozoa. In a specific aspect, this method further comprises a step of applying or administering to a biofilm-containing surface an antibacterial compound before, at the same time as or after applying or administering the one or more compounds of this invention.

In another aspect, the invention provides a medicament for treating an infection or for disruption of a biofilm which comprises one or more of the compounds of this invention e.g., those of formulas I-VI, and a method for making a medicament which comprises one or more of the compounds of this invention. In particular, the method comprises the step of combining one or more compounds of this invention with a pharmaceutically acceptable carrier to form a pharmaceutical composition for treatment of infection and/or biofilm formation. In another particular embodiment, the method further comprises combining an antibacterial compound appropriate for the application to a medicament along with one or more compounds of this invention.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION OF THE INVENTION

Figure 1:
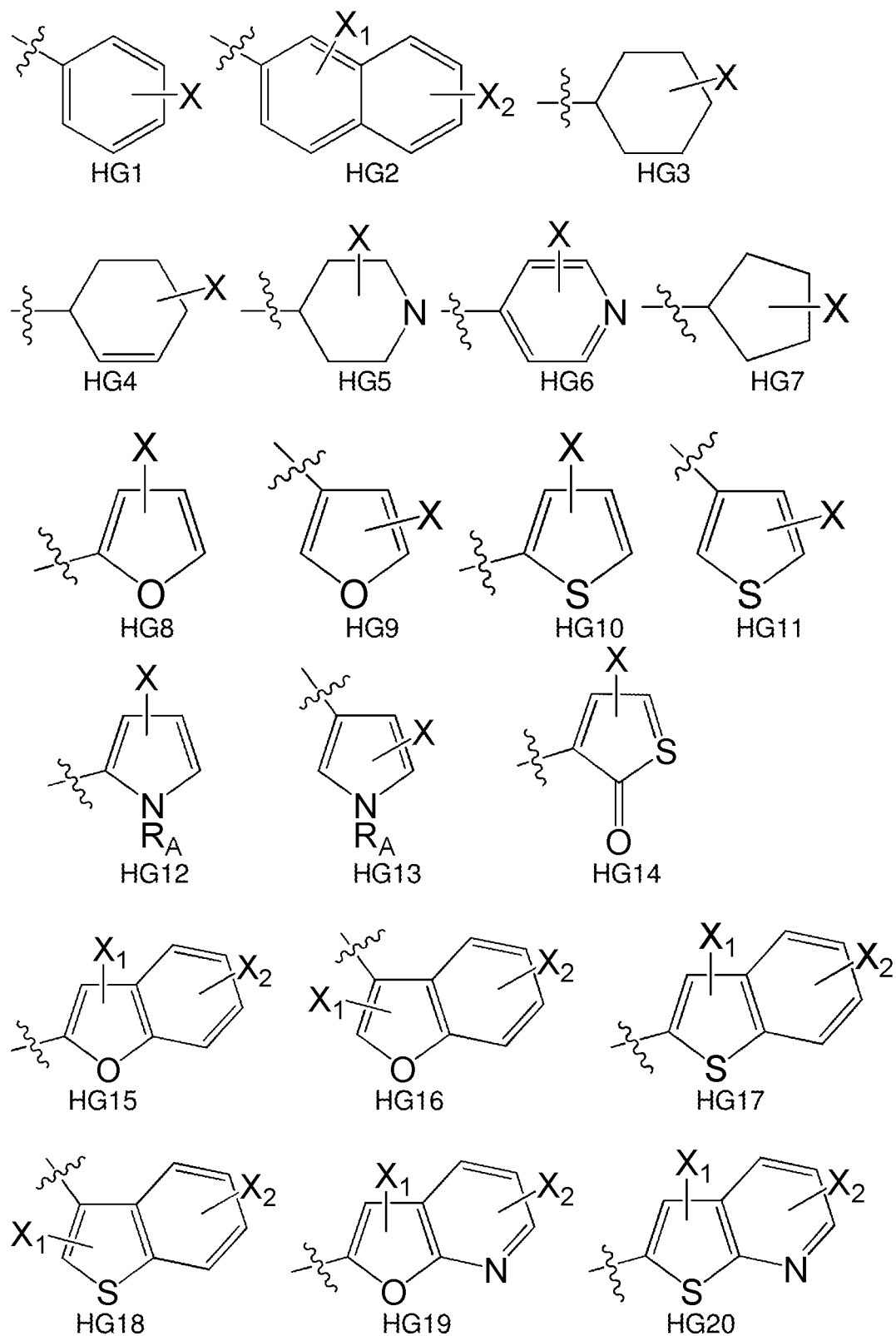
FIG. 1 (2 pages) illustrates exemplary HG groups.
Figure 1:
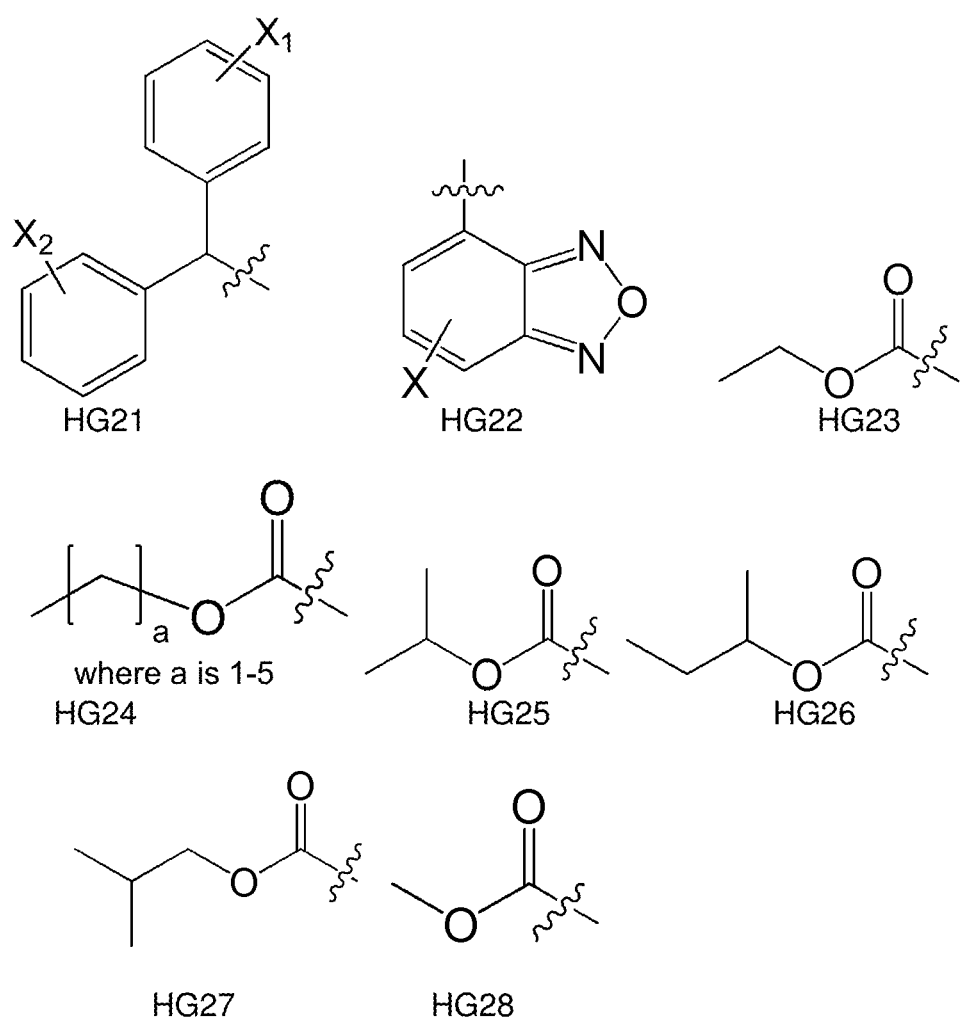
Figure 2:
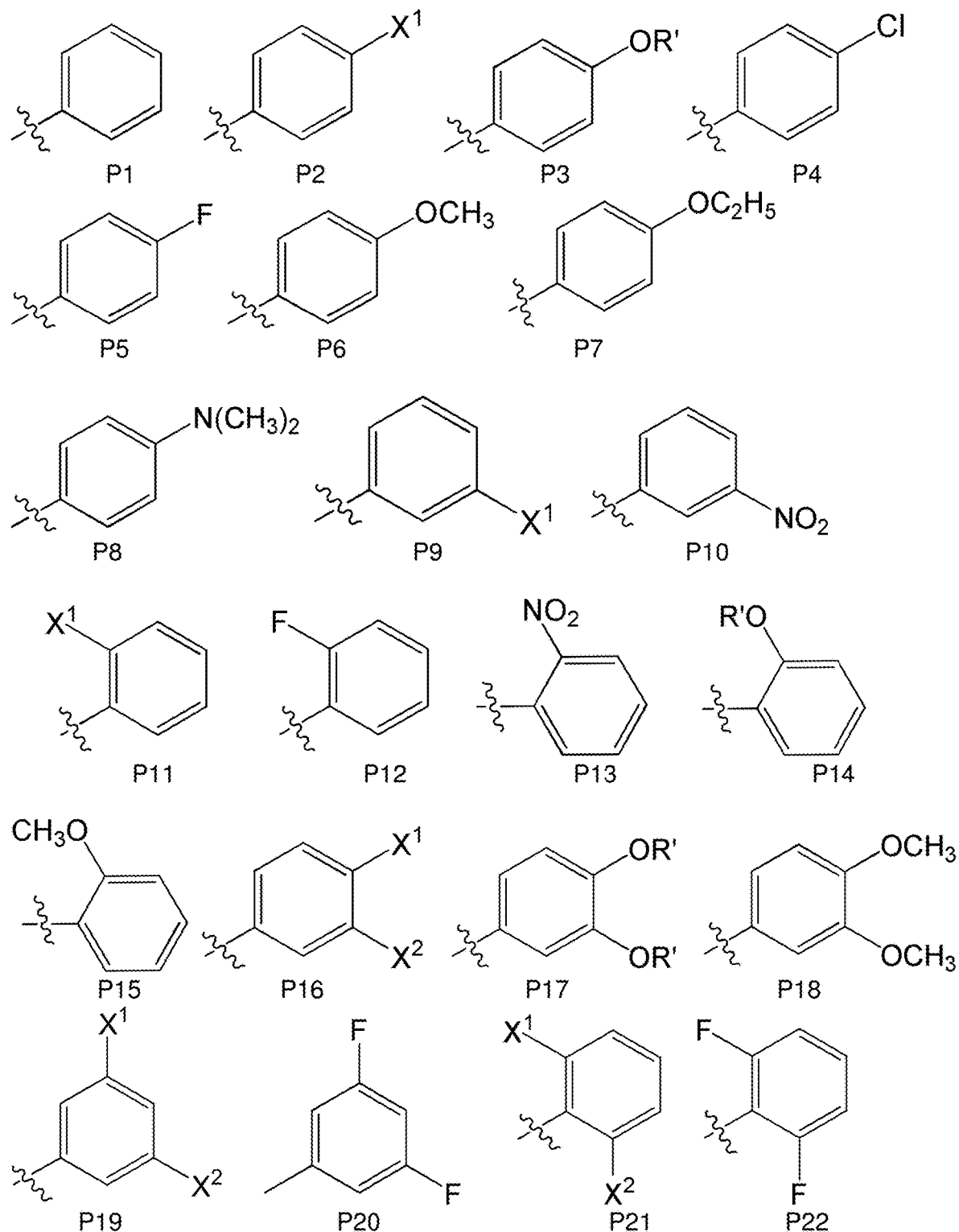
FIG. 2 (3 pages) illustrates exemplary HG groups.
Figure 2:
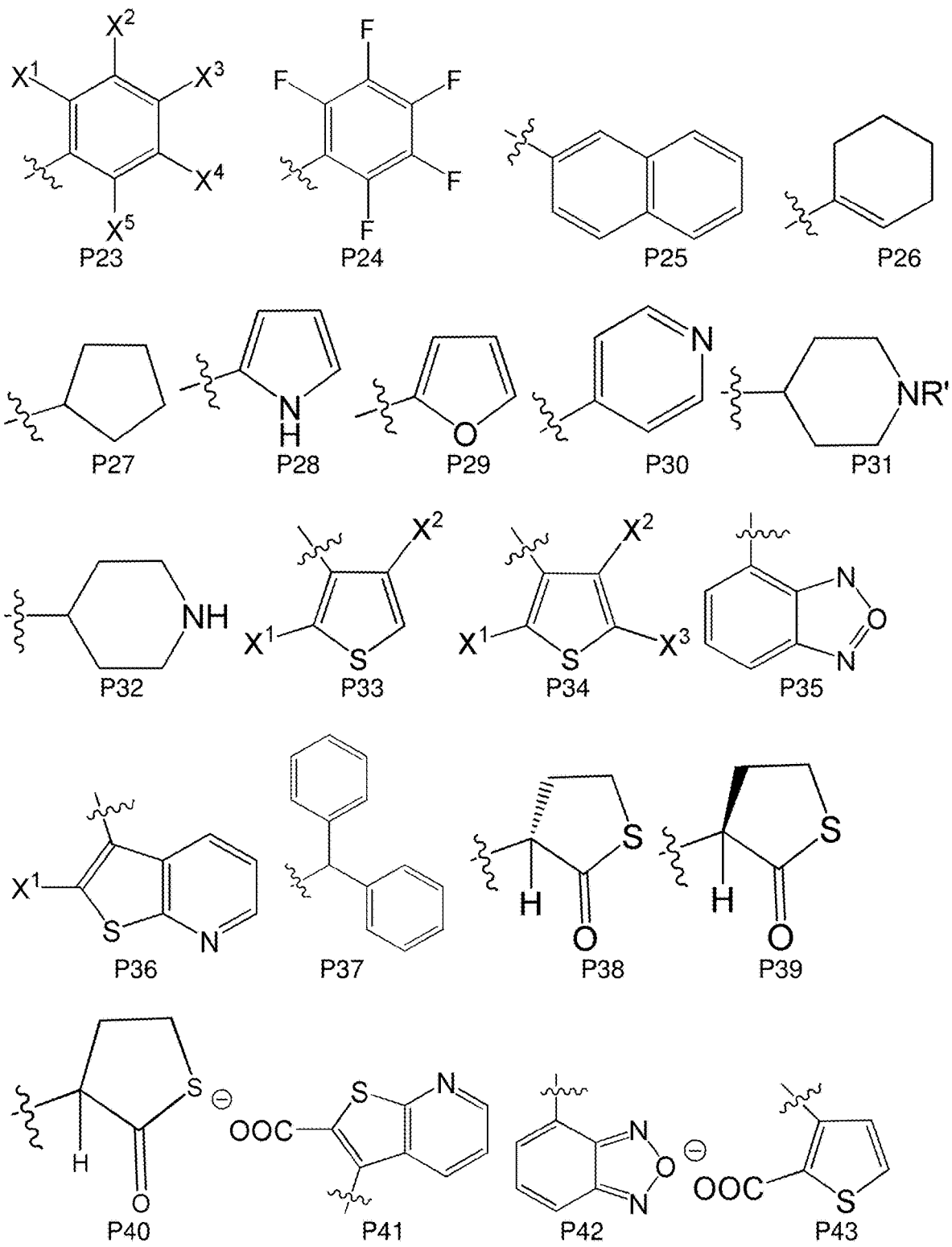
Figure 2:
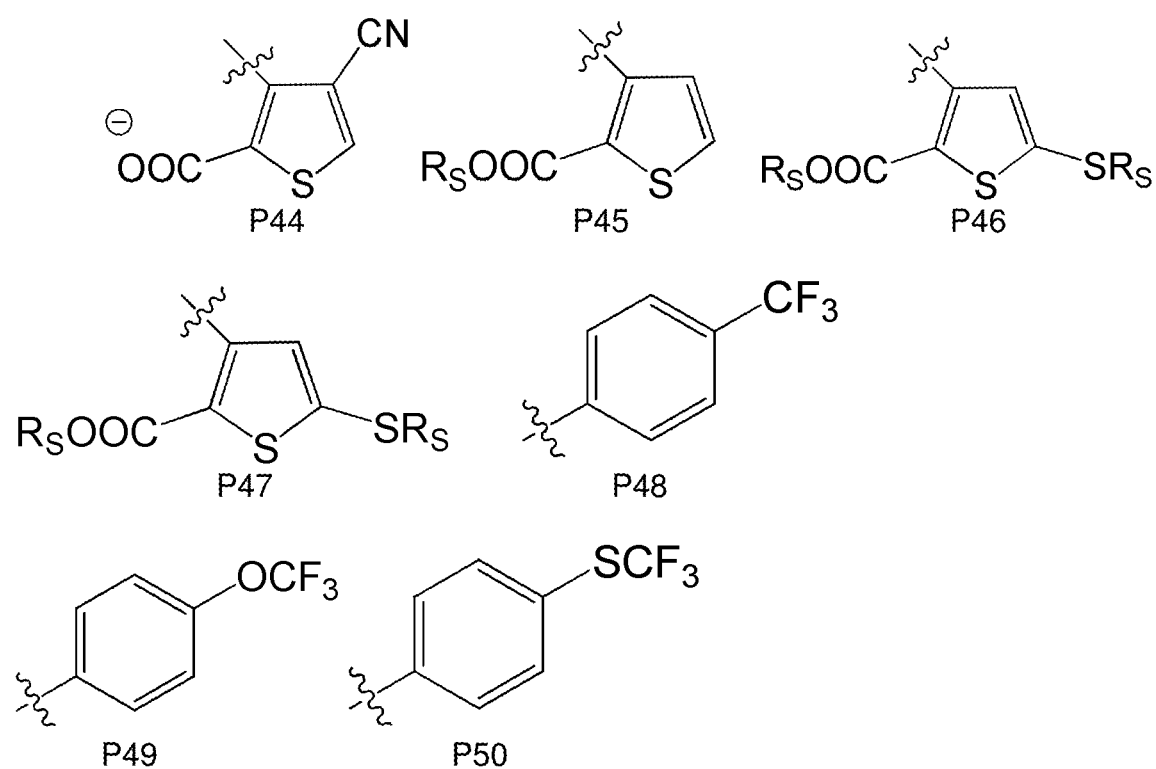
Figure 3:
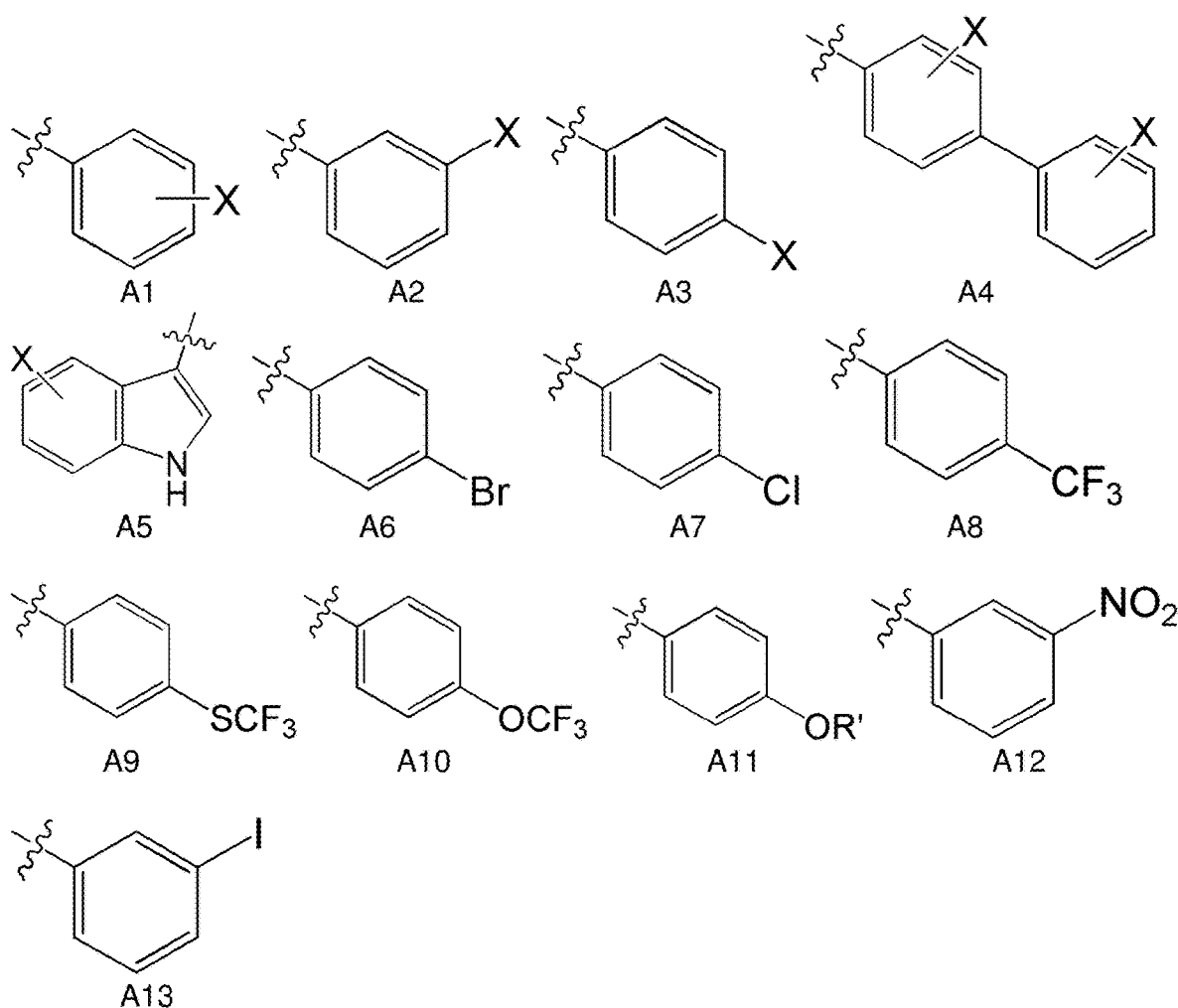
FIG. 3 illustrates exemplary A groups.

Unless defined otherwise, all technical and scientific terms used herein have the broadest meanings as commonly understood by one of ordinary skill in the art to which this invention pertains. In addition, hereinafter, the following definitions apply:

Quorum sensing assays conducted as described herein can be used to assess whether or no a given compound of the invention is a quorum sensing agonist or antagonist of a given bacterium, particularly a given Gram-Negative bacterium. It will be appreciated by one of ordinary skill in the art that assays other than those described herein can be employed to assess activation of or inhibition of biofilm formation as well as the effect of compounds of this invention on bacterial growth.

As defined herein, "contacting" means that a compound of the present invention is provided such that it is capable of making physical contact with another element, such as a microorganism, a microbial culture, a biofilm, or a substrate. In another embodiment, the term "contacting" means that a compound of the present invention is introduced into a subject receiving treatment, and the compound is allowed to come in contact in vivo.

Compounds of this invention that disrupt bacterial quorum sensing and biofilm formation can be used in combination with antimicrobial and antibacterial compounds (other than compounds which inhibit quorum sensing). The terms antimicrobial and antibacterial are employed broadly herein to refer to any compound that exhibits a growing inhibition activity on a microorganism or bacterium, respectively. A subset of such antimicrobial and antibacterial compounds are pharmaceutically acceptable for use in the treatment of humans and animals. A subset of antimicrobial and antibacterial compounds are biocides. A subset of antimicrobial and antibacterial compounds are antibiotics. In specific embodiments, compounds of the invention which are inhibitors or quorum sensing and biofilm formation are used to augment or facilitate the action of convention antibiotic treatment. The invention provides methods in which contact with or treatment with one or more quorum sensing compounds of the invention which inhibit quorum sensing is combined with contract with or treatment with one or more antimicrobial or antibacterial compounds. The invention provides methods in which contact with or treatment with one or more quorum sensing compounds of the invention which inhibit quorum sensing is combined with contract with or treatment with one or more antibiotics. Antibiotics include among others beta-lactam antibiotics, cephaosporins, clavulanic acid and derivatives thereof, aminoglycosides, tetracyclines, macrolide antibiotics.

Quorum sensing inhibitors of the invention can also generally be combined with antimicrobial agents, including antifungal agents, and antiviral agents.

In some cases, combination of one or more quorum sensing inhibitor of this invention with one or more antibacterial compound, antimicrobial compound or antiviral agent can enhance the activity of one or more antibacterial compound, antimicrobial compound or antiviral agent. In some case the combination of one or more quorum sensing inhibitor with one or more antibacterial compound, antimicrobial compound or antiviral agent synergizes the activity of the one or more antibacterial compound, antimicrobial compound or antiviral agent.

One or more quorum sensing inhibitor compounds of this invention can be combined with one or more antibacterial compounds, one or more antimicrobial compounds, one or more antiviral compounds and more specifically one or more antibiotics in pharmaceutically acceptable compositions useful for treatment of infections. Such pharmaceutical compositions typically further comprise a pharmaceutically acceptable carrier. Such combination compositions and medicaments can be employed for treatment of infection.

Contact with or treatment employing one or more quorum sensing inhibitor compounds of this invention can be combined with contact with or treatment with one or more antibacterial compounds, one or more antimicrobial compounds, one or more antiviral compounds and more specifically one or more antibiotics. In this case, contact or treatment is with one or more separate pharmaceutical composition which may be put in contact with the area to be treated (e.g., applied to a surface, including a biological surface) or administered to a subject at the same time or at different times. The quorum sensing inhibitor can be applied or administered before, after or at the same time as the antibacterial compound, antimicrobial compound or antiviral compound is applied or administered.

Aliphatic groups include straight chain, branched, and cyclic groups having a carbon backbone having from 1 to 30 carbon atoms. Aliphatic groups include alkyl groups, alkenyl groups, alkynyl groups, and aryl groups. Aliphatic groups are optionally substituted with one or more non-hydrogen substituents. Substituted aliphatic groups include among others those which are substituted with aryl groups, which in turn can be optionally substituted. Substituted aliphatic groups include fully halogenated or semihalogenated aliphatic groups, such as aliphatic groups having one or more hydrogens replaced with one or more fluorine atoms, chlorine atoms, bromine atoms and/or iodine atoms. Substituted aliphatic groups include fully fluorinated or semifluorinated aliphatic groups, such as aliphatic groups having one or more hydrogens replaced with one or more fluorine atoms. Aliphatic groups are optionally substituted with one or more protecting groups.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, 7-, or 8-member ring. The carbon rings in cyclic alkyl groups can also carry aliphatic groups. Cyclic alkyl groups can include bicyclic and tricyclic alkyl groups. Alkyl groups are optionally substituted with one or more non-hydrogen substituents. Substituted alkyl groups include among others those which are substituted with aliphatic groups, which in turn can be optionally substituted. Specific alkyl groups include methyl, ethyl, n-propyl, isopropyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms.

An alkoxy group is an alkyl group, as broadly discussed above, linked to oxygen and can be represented by the formula R—O—.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings.

Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry aliphatic groups. Cyclic alkenyl groups can include bicyclic and tricyclic aliphatic groups. Alkenyl groups are optionally substituted with one or more non-hydrogen substituents. Substituted alkenyl groups include among others those which are substituted with aliphatic groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

Alkynyl groups include straight-chain, branched and cyclic alkynyl groups. Alkynyl groups include those having 1, 2 or more triple bonds and those in which two or more of the triple bonds are conjugated triple bonds. Alkynyl groups include those having from 2 to 20 carbon atoms. Alkynyl groups include small alkynyl groups having 2 to 3 carbon atoms. Alkynyl groups include medium length alkynyl groups having from 4-10 carbon atoms. Alkynyl groups include long alkynyl groups having more than 10 carbon atoms, particularly those having 10-20 carbon atoms. Cyclic alkynyl groups include those having one or more rings. Cyclic alkynyl groups include those in which a triple bond is in the ring or in an alkynyl group attached to a ring. Cyclic alkynyl groups include those having a 3-, 4-, 5-, 6-, 7-, 8-, 9- or 10-member carbon ring and particularly those having a 3-, 4-, 5-, 6- or 7-member ring. The carbon rings in cyclic alkynyl groups can also carry aliphatic groups. Cyclic alkynyl groups can include bicyclic and tricyclic aliphatic groups. Alkynyl groups are optionally substituted with one or more non-hydrogen substituents. Substituted alkynyl groups include among others those which are substituted with alkyl or aryl groups, which groups in turn can be optionally substituted. Alkynyl groups include acetyl, methylacetyl, 1-pentynyl, and 2-pentynyl, all of which are optionally substituted. Substituted alkynyl groups include fully halogenated or semihalogenated alkynyl groups, such as alkynyl groups having one or more hydrogens replaced with one or more fluorine atoms, chlorine atoms, bromine atoms and/or iodine atoms. Substituted alkynyl groups include fully fluorinated or semifluorinated alkynyl groups, such as alkynyl groups having one or more hydrogens replaced with one or more fluorine atoms.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S, or combinations of one or two or three N, O or S. Aryl groups are optionally substituted with one or more non-hydrogen substituents. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. The term heteroaryl is used for aryl groups having one or more heteroaromatic rings. Aryl groups include those that are not heteroaryl groups.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

The term "heterocyclic or heterocyclyl" generically refers to a monoradical that contains at least one ring of atoms, which may be a saturated, unsaturated wherein one or more carbons of the ring are replaced with a heteroatom (a non-carbon atom) To satisfy valence the heteroatom may be bonded to H or a substituent groups. Ring carbons may be replaced with —O—, —S—, —NR—, —N=among others. More specifically heterocyclic groups can contain one or two 4-6 member rings wherein two rings may be fused. In specific embodiments, one or two rings of the heterocyclic group can contain one, two or three heteroatoms, particularly —O—, —S—, —NR— or —N= and combinations of such heteroatoms.

Protecting groups are groups substituted onto an aliphatic hydrocarbon for protection of one or more substituents, for example protection of alcohols, amines, carbonyls, and/or carboxylic acids. Protecting groups include, but are not limited to, acetyl groups, MEM groups, MOM groups, PMB groups, Piv groups, THP groups, TMS groups, TBDMS groups, TIPS groups, methyl ethers, Cbz groups, BOC groups, FMOC groups, benzyl groups, PMP groups, acetal groups, ketal groups, acylal groups, dithiane groups, methyl esters, benzyl esters, t-butyl esters, and silyl esters. These and other protecting groups known in the art of organic synthesis may be optionally used as a substituent of an aliphatic group.

Optional substitution of aliphatic groups includes substitution with one or more aliphatic groups, wherein the aliphatic groups are optionally substituted.

Optional substituents for aliphatic groups include among others: —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; wherein R is selected from the group consisting of, a hydrogen, a halogen, an amine group, a substituted or unsubstituted unbranched C1-C12 acyclic aliphatic group, a substituted or unsubstituted branched C1-C12 acyclic aliphatic group, a substituted or unsubstituted C3-C8 cycloalkyl group, a substituted or unsubstituted C3-C8 cycloalkenyl group, a fluorinated C1-C12 alkyl group, a substituted or unsubstituted aryl group, a substituted or unsubstituted heterocycle, a substituted or unsubstituted C1-C12 alkoxy group, a fluorinated C1-C12 alkoxy group, a hydroxyl group, a nitrile group, an azide group, a nitro group, an acyl group, a thiol group, a protecting group, —COOR, —COR, —CON(R)$_2$, —OCON(R)$_2$, —N(R)$_2$, —SR, —SO$_2$R, —SOR, —OCOOR, —SO$_2$N(R)$_2$, and —OR; additionally, R and R can form a ring.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The term "effective amount" is used generically herein to refer to the amount of a given compound or in case of a mixture the combined amount of mixture components that provides a measureable effect for a listed function. For example, in certain aspects of the invention, a compound of the invention is contacted with an element in order to disrupt a biofilm and in this case, the effective amount or combined effective amount of the compound or compounds is that amount that shows a measurable disruption of a biofilm. The effective amount will vary dependent upon the stated function, the environment or element being contacted, the organism forming the biofilm or which is to be contacted, the state of development of the biofilm, among other conditions of the use of the compound. It will be understood by one of ordinary skill in the art, that for a given application, the effective amount can be determined by application of routine experimentation and without undue experimentation by methods that are described herein or that are known in the art.

The term "therapeutically effective amount" is used generically herein to refer to the amount of a given compound or in case of a mixture the combined amount of a mixture of components when administered to the individual (including a human, or non-human animal) that provides a measureable therapeutic effect for a listed disease, disorder or condition to at least partially ameliorate a symptom of such disease, disorder or condition. The present invention provides methods of treating disorders, diseases conditions and symptoms in a human or non-human animal and particularly in a human, by administering to an individual in need of treatment or prophylaxis, a therapeutically effective amount of one or more compounds of this invention to the individual in need thereof. The result of treatment can be partially or completely alleviating, inhibiting, preventing, ameliorating and/or relieving the disorder, condition or one or more symptoms thereof. As is understood in the art, the therapeutically effective amount of a given compound will depend at least in part upon, the mode of administration, any carrier or vehicle (e.g., solution, emulsion, etc.) employed, the extent of damage and the specific individual (human or non-human) to whom the compound is to be administered (age, weight, condition, sex, etc.). The dosage requirements needed to achieve the "therapeutically effective amount" vary with the particular compositions employed, the route of administration, the severity of the symptoms presented and the particular subject being treated. Based on the results obtained in standard pharmacological test procedures, projected daily dosages of active compound can be determined as is understood in the art.

Administration is intended to encompass administration of a compound, pharmaceutically acceptable salt, solvate or ester thereof alone or in a pharmaceutically acceptable carrier thereof or administration of a prodrug derivative or analog of a compound of this invention which will form an equivalent amount of the active compound or substance within the body. An individual in need of treatment or prophylaxis includes those who have been diagnosed to have a given disorder or condition and to those who are suspected, for example, as a consequence of the display of certain symptoms, of having such disorders or conditions.

Compounds of this invention can be employed in unit dosage form, e.g. as tablets or capsules. In such form, the active compound or more typically a pharmaceutical composition containing the active compound is sub-divided in unit dose containing appropriate quantities of the active compound; the unit dosage forms can be packaged compositions, for example, packaged powders, vials, ampules, pre-filled syringes or sachets containing liquids. The unit dosage form can be, for example, a capsule or tablet itself, or it can be the appropriate number of any such compositions in package form.

The dosage can vary within wide limits and as is understood in the art will have to be adjusted to the individual requirements in each particular case. By way of general guidance, the daily oral dosage can vary from about 0.01 mg to 1000 mg, 0.1 mg to 100 mg, or 10 mg to 500 mg per day of a compound of formulas herein or of the corresponding amount of a pharmaceutically acceptable salt thereof. The daily dose may be administered as single dose or in divided doses and, in addition, the upper limit can also be exceeded when this is found to be indicated.

Any suitable form of administration can be employed in the method herein. The compounds of this invention can, for example, be administered in oral dosage forms including tablets, capsules, pills, powders, granules, elixirs, tinctures, suspensions, syrups and emulsions. Oral dosage forms may include sustained release or timed release formulations. The compounds of this invention may also be administered topically, intravenously, intraperitoneally, subcutaneously, or intramuscularly, all using dosage forms well known to those of ordinary skill in the pharmaceutical arts.

Compounds of this invention can also be administered in intranasal form by topical use of suitable intranasal vehicles. For intranasal or intrabronchial inhalation or insulation, the compounds of this invention may be formulated into an aqueous or partially aqueous solution, which can then be utilized in the form of an aerosol. Administration includes any form of administration that is known in the art and is intended to encompass administration in any appropriate dosage form and further is intended to encompass administration of a compound, alone or in a pharmaceutically acceptable carrier. Pharmaceutical carriers are selected as is known in the art based on the chosen route of administration and standard pharmaceutical practice.

The compounds of this invention can also be administered to the eye, preferably as a topical ophthalmic formulation. The compounds of this invention can also be combined with a preservative and an appropriate vehicle such as mineral oil or liquid lanolin to provide an ophthalmic ointment. The compounds of this invention may be administered rectally or vaginally in the form of a conventional suppository. The compounds of this invention may also be administered transdermally through the use of a transdermal patch containing the active compound and a carrier that is inert to the active compound, is non toxic to the skin, and allows delivery of the agent for systemic absorption into the blood stream via the skin.

The compounds of the invention may be administered employing an occlusive device. A variety of occlusive devices can be used to release an ingredient into the blood stream such as a semipermeable membrane covering a reservoir containing the active ingredient with or without a carrier, or a matrix containing the active ingredient. Other occlusive devices are known in the literature.

Pharmaceutical compositions and medicaments of this invention comprise one or more compounds in combination with a pharmaceutically acceptable carrier, excipient, or diluent. Such compositions and medicaments are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. The invention also encompasses method for making a medicament employing one or more compounds of this invention which exhibit a therapeutic effect.

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form.

Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Suitable examples of liquid carriers for oral and parenteral administration include water of appropriate purity, aqueous solutions (particularly containing additives, e.g. cellulose derivatives, sodium carboxymethyl cellulose solution), alcohols (including monohydric alcohols and polyhydric alcohols e.g. glycols) and their derivatives, and oils. For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant. Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form. The carrier can also be in the form of creams and ointments, pastes, and gels. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Compounds of formula I can also be present in the form of zwitterions.

Pharmaceutically acceptable salts comprise pharmaceutically-acceptable anions and/or cations. Pharmaceutically-acceptable cations include among others, alkali metal cations (e.g., Li+, Na+, K+), alkaline earth metal cations (e.g., Ca2+, Mg2+), non-toxic heavy metal cations and ammonium (NH4+) and substituted ammonium (N(R')4+, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl—, Br—), sulfate, acetates (e.g., acetate, trifluoroacetate), ascorbates, aspartates, benzoates, citrates, and lactate.

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988);

and Nogrady (1985) Medicinal Chemistry A Biochemical Approach, Oxford University Press, New York, pages 388-392).

The invention expressly includes pharmaceutically usable solvates of compounds according to formulas herein. The compounds of formula I can be solvated, e.g. hydrated. The solvation can occur in the course of the manufacturing process or can take place, e.g. as a consequence of hygroscopic properties of an initially anhydrous compound of formulas herein (hydration).

In specific embodiments herein, compounds 2, 13, 18E, 20E, 23E, 25E 30E, 32, 33, 34, 35, 36, 37, 38, 39 are particularly useful for disruption of bacterial quorum sensing and biofilm disruption, particularly in *E. coli, V. fischeri* and/or *A. tumefaciens*.

In specific embodiments herein, compounds 3, and 19E are particularly useful for activation of bacterial quorum sensing and biofilm formation, particularly in *E. coli, V. fischeri* and/or *P. aeruginosa*.

In specific embodiments herein, compounds 2, 13, 18E, 30E, 32, 33, 34, 35, 36, 37 are particularly useful for disruption of bacterial quorum sensing and biofilm disruption in *E. coli*. In specific embodiments, compounds 1E, 18E, 20E, 22E, 23E, 25E, 26E, 27E, 28E, 30E, 33, 34, 36, 38 and 39 are particularly useful for disruption of bacterial quorum sensing and biofilm disruption in *V. fischeri*. In specific embodiments herein, compounds 1E, 26E, 27E, and 30E are particularly useful for disruption of bacterial quorum sensing and biofilm formation, particularly in *A. tumefaciens*.

In specific embodiments herein, compounds 3, 14, 16, 17, 1E, 19E, 22E, 26E, 27E, 28E, and 31 are particularly useful for activation of bacterial quorum sensing and biofilm formation in *E. coli*. In specific embodiments herein compound 24E is particularly useful for activation of bacterial quorum sensing and biofilm formation in *A. tumefaciens*. In specific embodiments herein compound 19E is particularly useful for activation of bacterial quorum sensing and biofilm formation in *V. fischeri*. In specific embodiments herein compounds 3 and 1E are particularly useful for activation of bacterial quorum sensing and biofilm formation in *P. aeruginosa*.

In specific embodiments herein compounds of the formulas herein which exhibit 20% or more inhibition in quorum sensing antagonism assays as described in the examples herein are particularly useful for disruption of bacterial quorum sensing and bacterial biofilm formation. In specific embodiments herein compounds of the formulas herein which exhibit 50% or more inhibition in quorum sensing antagonism assays as described in the examples herein are particularly useful for disruption of bacterial quorum sensing and bacterial biofilm formation. In specific embodiments herein compounds of the formulas herein which exhibit 75% or more inhibition in quorum sensing antagonism assays as described in the examples herein are particularly useful for disruption of bacterial quorum sensing and bacterial biofilm formation.

In specific embodiments herein compounds of the formulas herein which exhibit 20% or more activation in quorum sensing agonism assays as described in the examples herein are particularly useful for activation of bacterial quorum sensing and bacterial biofilm formation. In specific embodiments herein compounds of the formulas herein which exhibit 50% or more activation in quorum sensing agonism assays as described in the examples herein are particularly useful for activation of bacterial quorum sensing and bacterial biofilm formation. In specific embodiments herein compounds of the formulas herein which exhibit 75% or more activation in quorum sensing agonism assays as described in the examples herein are particularly useful for activation of bacterial quorum sensing and bacterial biofilm formation.

Compounds of this invention are additionally useful as tools for use in research in the study of quorum sensing in bacteria.

Well-known methods for assessment of drugability can be used to further assess active compounds of the invention for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, Experimental and computational approaches to estimate solubility and permeability in drug discovery and development settings, Adv. Drug Del. Rev., 2001, 46, 3-26 and Arup K. Ghose, Vellarkad N. Viswanadhan, and John J. Wendoloski, A Knowledge-Based Approach in Designing Combinatorial or Medicinal Chemistry Libraries for Drug Discovery, J. Combin. Chem., 1999, 1, 55-68.) In general a preferred drug for oral administration exhibits no more than one violation of the following rules:

(1) Not more than 5 hydrogen bond donors (e.g., nitrogen or oxygen atoms with one or more hydrogens);

(2) Not more than 10 hydrogen bond acceptors (e.g., nitrogen or oxygen atoms);

(3) Molecular weight under 500 g/mol and more preferably between 160 and 480; and (4) log P less than 5 and more preferably between −0.4 to +5.6 and yet more preferably −1<log P<2.

Compounds of this invention preferred for therapeutic application include those that do not violate one or more of 1-4 above.

Compounds of this invention preferred for therapeutic application include those having log P less than 5 and more preferably between −0.4 to +5.6 and yet more preferably −1<log P<2.

The compounds of this invention may contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

It is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

As used herein, the term "treating" includes preventative as well as disorder remittent treatment. As used herein, the terms "reducing", "suppressing" and "inhibiting" have their commonly understood meaning of lessening or decreasing.

In certain embodiments, the present invention encompasses administering the compounds useful in the present invention to a patient or subject. A "patient" or "subject", used equivalently herein, refers to an animal. In particular, an animal refers to a mammal, preferably a human. The subject either: (1) has a condition remediable or treatable by administration of a compound of the invention; or (2) is susceptible to a condition that is preventable by administering a compound of this invention.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The invention includes compounds of formula I which exhibit activity as antagonist of quorum sensing in bacteria, particularly specific bacteria disclosed herein. The invention also includes compounds of formula I which exhibit activity as agonist of quorum sensing in bacteria, particularly specific bacteria disclosed herein.

In an embodiment, compounds of formula I have activity as an agonist or antagonist of native quorum sensing compounds. In an embodiment, compounds of formula I can be used to selectively adjust the virulence, biofilm production, or symbiotic behavior of a quorum sensing bacteria. In an embodiment, compounds of formula I can be administered to a subject to initiate an immune response towards a quorum sensing bacteria.

In an embodiment, certain compounds are preferred for selectively adjusting the virulence, biofilm production, or symbiotic behavior of a particular species or strain of a particular species of quorum sensing bacteria. In an embodiment, preselected mixtures of L- and D-isomers of compounds of the present invention can be used to selectively adjust the virulence, biofilm production, or symbiotic behavior of a particular species or strain of a particular species of quorum sensing bacteria.

In an embodiment, the compounds of the present invention are useful as a combinatorial library comprising a preselected mixture of two or more compounds of the present invention. In an embodiment, the two or more compounds can each be used to separately selectively adjust the virulence, biofilm production, or symbiotic behavior of a particular species or strain of a particular species of quorum sensing bacteria.

When a group of substituents is disclosed herein, it is understood that all individual members of those groups and all subgroups, including any isomers and enantiomers of the group members, and classes of compounds that can be formed using the substituents are disclosed separately. When a Markush group or other grouping is used herein, all individual members of the group and all combinations and subcombinations possible of the group are intended to be individually included in the disclosure. When a compound is described herein such that a particular isomer or enantiomer of the compound is not specified, for example, in a formula or in a chemical name, that description is intended to include each isomer and enantiomer of the compound described individually or in any combination. When an atom is described herein, including in a composition, any isotope of such atom is intended to be included. Specific names of compounds are intended to be exemplary, as it is known that one of ordinary skill in the art can name the same compounds differently. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention is further illustrated by the following non-limiting examples.

THE EXAMPLES

Example 1

Heterocycles and carbocycles were chosen as head groups for a library (FIG. 4) in order to probe the orientation and electronics necessary for a positive binding interaction with Trp60, shown to be an important residue in the N-terminal domain of the LasR crystal structure. Fluorine was chosen as a lactone carbonyl mimic due to its ability to accept hydrogen bonds. Multiple fluorine aromatic substitutions were examined to determine if Trp60 could hydrogen bond to multiple atoms given the correct spatial orientation. Non-hydrogen bonding oxygen-containing moieties were chosen to examine the effects of non-hydrogen bonding electrostatic interactions. The library also contained carbocycles to explore the necessity of the Trp60 binding interaction. A thiolactone analog shown to be active in previous experiments was chosen to serve as a control compound for our bacterial strains. [Passador, L.; Tucker, K. D.; Guertin, K. R.; Journet, M. P.; Kende, A. S.; Iglewski, B. H., Functional analysis of the *Pseudomonas aeruginosa* Autoinducer PAI. J. Bacteriol. 1996, 178, 5995-6000.] The glycine ethyl ester and the alanine methyl ester were chosen to explore the effects of variations on synthetic ring-opened forms of the lactone unavailable to nature.

Based upon this design strategy, a 17 member non-lactone based library (FIG. 4) was synthesized using solution-phase chemistry. To facilitate the ease of synthesis, a Meldrum's Acid derivative was used as a common intermediate. Reacting Meldrum's Acid with decanoyl chloride afforded the Meldrum's Acid derivative, which was refluxed with the desired amines to form the initial library (Scheme 1).

Scheme 1 is a general synthetic method for producing 3-oxo-dodecanoyal derivatives of the natural autoinducer for *P. aeruginosa*. DMAP=dimethyl amino pyridine. TEA=triethyl amine. R can, for example, be a unsubstituted or substituted heterocycle or carbocycle:

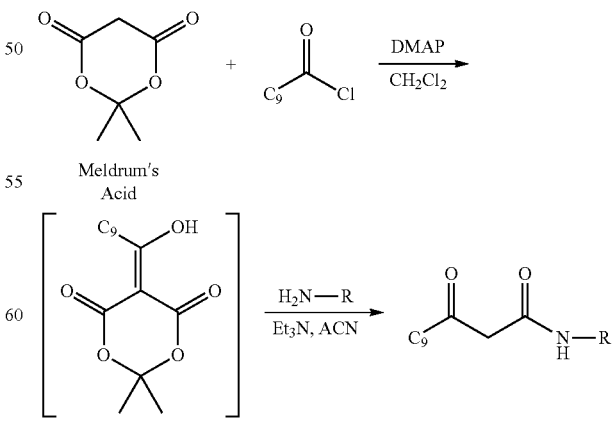

This method can be employed for synthesis of various compounds herein by choice of starting materials and routine adaptation of methods disclosed herein or of methods that are well-known in the art. This method can be used for synthesis of compounds, where R is various substituted and unsubstituted heterocyclic rings, in particular, where R is a ring substituted thiolactone group. Appropriate starting materials for making ring-substituted compounds of this inventions are readily available either form commercial sources or by known synthetic methods. Additional references which provide details useful in the synthesis of thiolactones of this invention include among others U.S. Pat. Nos. 3,840,534 and 3,926,965 and Krasncv et al. (1999) Russian J. Org. Chem. 35(4):572-577.

Figure 5A:
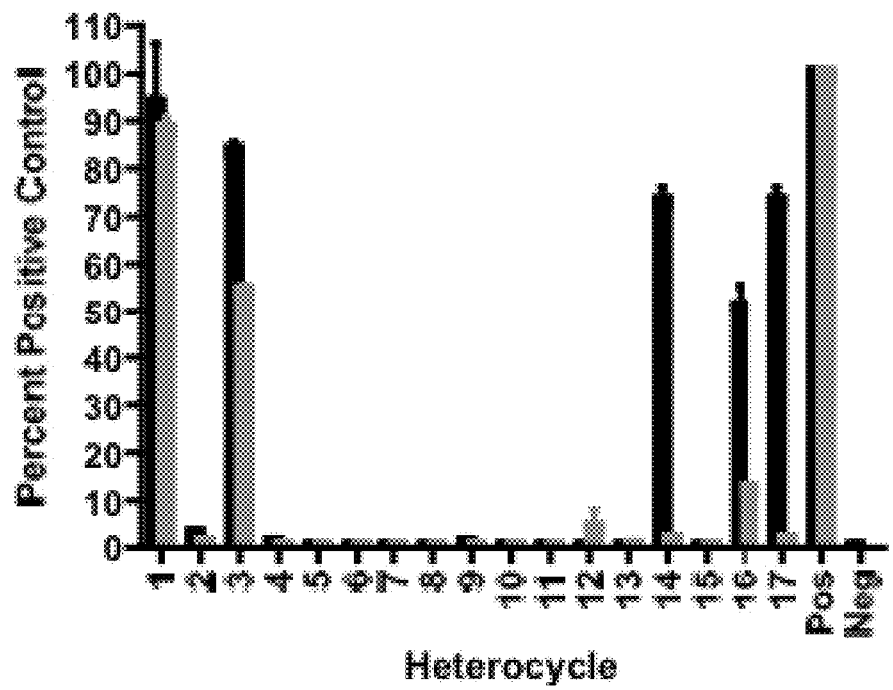
FIG. 5A is a bar graph showing the results of agonism assay for initial heterocyclic and carbocyclic library (Scheme 1) shown as a percent of the positive control. The black bars are DH5α (pJN105L+pSC11) and the grey bars are PA01 MW1 (pUM15). Agonism positive control=activity of the reporter strain at full turn on for the strain. Full turn on for each strain: DH5α (pJN105L+ pSC11)—100 nM OdDHL; PA01 MW1 (pUM15)—100 µM OdDHL. Negative control (Neg)=bacteria in the absence of natural and synthetic ligand. Error bars=standard deviation of the mean of triplicate samples.
Figure 5B:
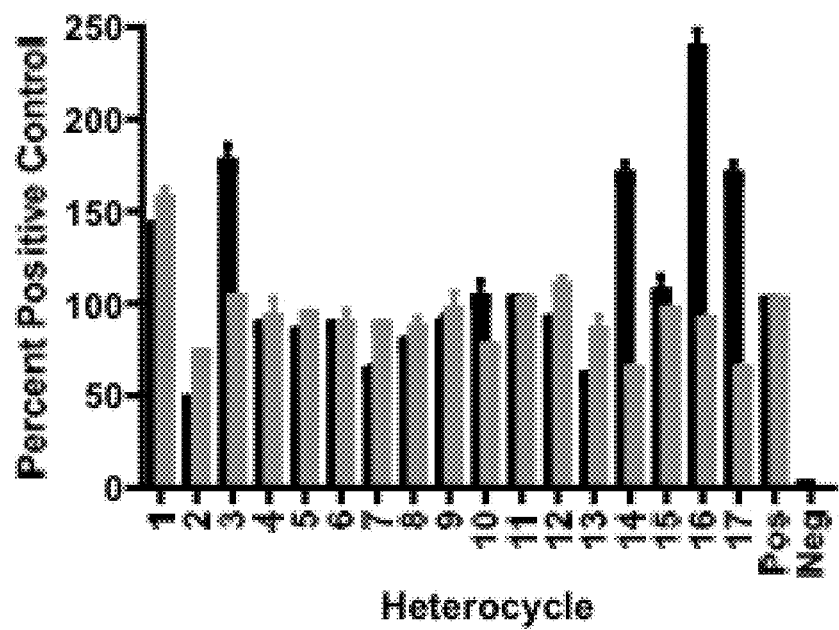
FIG. 5B is a bar graph showing the results of agonism assay for initial heterocyclic and carbocyclic library (Scheme 1) shown as a percent of the positive control. Antagonism positive control (Pos)=activity of the reporter strain in the absence of synthetic ligand at the EC50 value for the strain. Strain EC50 values: DH5α (pJN105L+ pSC11)-10 nM OdDHL; PA01 MW1 (pUM15)-1 µM OdDHL. Negative control (Neg)=bacteria in the absence of natural and synthetic ligand. Error bars=standard deviation of the mean of triplicate samples.

The initial library was tested for LasR agonistic and antagonistic activity in two strains: Escherichia coli DH5α (pJN105L+pSC11) [Lee, J. H.; Lequette, Y.; Greenberg, E. P., Activity of purified QscR, a Pseudomonas aeruginosa orphan quorum-sensing transcription factor. Mol. Microbiol. 2006, 59 (2), 602-609] and P. aeruginosa PA01 MW1 (pUM15) [Muh, U.; Schuster, M.; Heim, R.; Singh, A.; Olson, E.; Greenberg, E. P., Novel Pseudomonas aeruginosa Quorum-Sensing Inhibitors Identified in an Ultra-High-Throughput Screen. Antimicrob. Agents Chemother. 2006, 50, 3674-3679] (FIGS. 5A and 5B). Both strains allow for synthetic autoinducer mimic evaluation and contain a reporter gene that allows for a quantitative readout of QS activity. DH5α (pJN105L+pSC11) is a heterologous β-galactosidase E. coli reporter strain containing a plasmid for the P. aeruginosa LasR gene. The PA01 MW1 (pUM15) strain uses the natural P. aeruginosa background containing a LasI deletion and the gene for yellow fluorescent protein (YFP) under the control of the LasI promoter to evaluate the LasI/R activity. Since the PA01 MW1 (pUM15) strain evaluates LasR in the natural P. aeruginosa background, in contrast to the heterologous E. coli strain, an improved idea of the interplay between the isolated LasI/R system and the combination of LasI/R with other QS subsystems such as QscR can be determined. Furthermore, additional nuances of the natural system such as compound permeability are incorporated in assays using the PA01 MW1 (pUM15) strain.

The initial library was also tested in Vibrio fischeri ESI 114 (Δ-LuxI) [Lupp, C.; Urbanowski, M.; Greenberg, E. P.; Ruby, E. G., The Vibrio fischeri quorum-sensing systems ain and lux sequentially induce luminescence gene expression and are important for persistence in the squid host. Mol. Microbiol. 2003, 50 (1), 319-331] and Agrobacterium tumefaciens WCF (pCF372). [Zhu, J.; Beaber, J. W.; More, M. I.; Fuqua, C.; Eberhard, A.; Winans, S. C., Analogs of the autoinducer 3-oxooctanoyl-homoserine lactone strongly inhibit activity of the TraR protein of Agrobacterium tumefaciens. J. Bacteriol. 1998, 180 (20), 5398-5405.] However, activities were low to modest in these species, except for compound 1, which is a good antagonist in both strains. The general lack of activity in the V. fischeri and A. tumefaciens strains is to be expected considering that the library was designed for the P. aeruginosa LasR protein and reinforces previous work demonstrating that the length of the acyl tail is highly species dependent. [Geske, G. D.; O'Neill, J. C.; Miller, D. M.; Mattmann, M. E.; Blackwell, H. E., Modulation of Bacterial Quorum Sensing: Systematic Evaluation of N-Acylated Homoserine Lactones in Multiple Species and New Insights into Their Mechanism of Action. J. Am. Chem. Soc. 2007, 129, 13613-13625.]

This set of screening data provides several noteworthy discoveries. First, the thiolactone derivative of the P. aeruginosa natural ligand (1) is highly active in all strains tested—either as an agonist in the strains examining LasR activity [94% agonist in DH5α (pJN105L+pSC11) and 88% agonist in PA01 MW1 (pUM15)] or as an antagonist in the V. fischeri (LuxR; 92% inhibition) and A. tumefaciens (TraR; 65% inhibition) strains. The high degree of activity across these four strains suggests that the sulfur substitution in the lactone ring does not sufficiently alter the binding of 1 from the natural ligand and suggests that the electronics at that position are not critical for binding. Second, the cyclopentyl amine derivative (3) is an agonist in both strains testing for LasR activity and a modest antagonist in the V. fischeri strain. This is remarkable because the cyclopentyl amine head group lacks functionality for hydrogen bond acceptance, which has been proposed as critical for neutral ligand binding based on the LasR crystal structure. This suggests that either the lactone carbonyl's hydrogen bonds are not as crucial as originally thought, or that 3 binds in an alternative manner. Third, compound 2 is of interest for its antagonism capabilities in both strains evaluating the LasI/R system, even though there are no hydrogen bond acceptor substitutions, further questioning the proposed critical nature of the lactone carbonyl. Fourth, compound 14 provides some insight into the differences between the isolated LasI/R system in E. coli and the LasI/R system in the natural P. aeruginosa background. LasR appears to be strongly agonized by 14 in the E. coli strain, while assays using the natural P. aeruginosa background show slight antagonism rather than an agonistic effect. Compound 14 represented an excellent candidate for further testing in additional heterologous strains containing isolated QS subsystems like QscR and RhlI/R.

Figure 4:
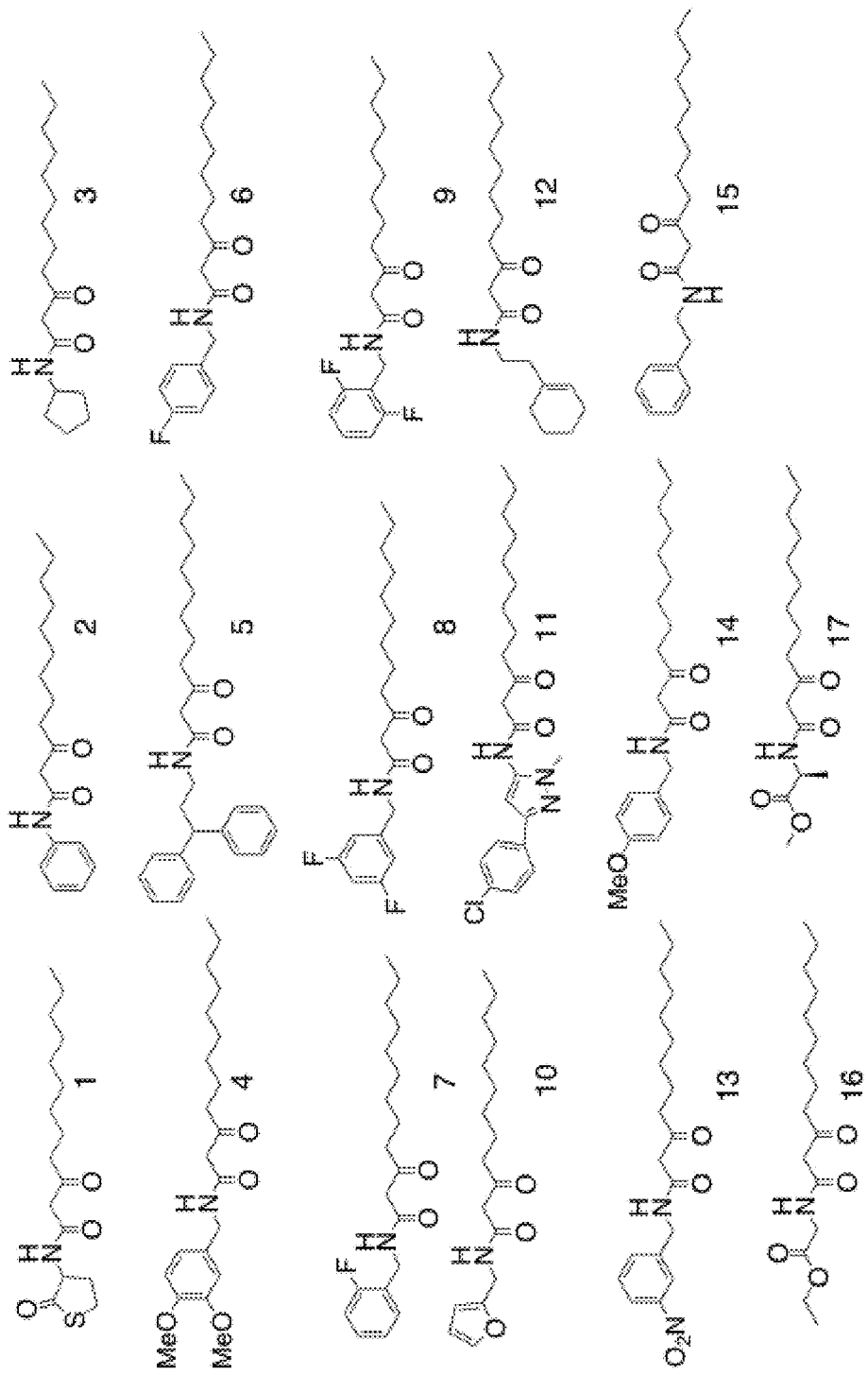
FIG. 4 provides structures (and reference numbers) of exemplary non-homoserine lactone based autoinducer analogs synthesized by the method highlighted in Scheme 1.

Additional comparative data for several compounds of FIG. 4 is provided in Table 1

TABLE 1

| Compd | E. coli DH5α (pJN105L + pSC11) | | P. aeruginosa PA01 MW1 | | V. fischeri ESI 114 (Δ-LuxI) | | A. Tumefaciens WCF (pCF372) | |
|---|---|---|---|---|---|---|---|---|
| | Antagonist | Agonist | Antagonist | Agonist | Antagonist | Agonist | Antagonist | Agonist |
| 2 | 53.7 | — | 28.7 | — | — | — | — | — |
| 3 | — | 83.5 | — | 54.2 | 89.4 | — | — | — |
| 7 | 38.8 | — | — | — | — | 3.1 | — | — |
| 10 | — | — | 25.5 | — | — | 3.3 | — | — |
| 12 | — | — | −6.6 | 4.0 | 34.9 | 3.0 | −22.0 | — |
| 13 | 41.0 | — | 16.8 | — | 43.8 | 1.7 | — | — |
| 14 | −67.7 | 73.0 | 37.8 | — | 14.6 | — | — | — |

Agonist results are reported as a percent of activation compared to the positive control. Antagonist results are reported as a percent inhibition compared to a positive control. Negative values indicate agonist properties detected in an antagonist assay.

Example 2: Focused Libraries-Racemic Thiolactone Library

Based upon the results of the initial library screen, focused libraries around the most active leads (1, 2, 3, 16 from FIG. 4) were developed. In these libraries, the identified head group remained identical while the 3-oxo-C12 acyl tail was replaced with mimics previously shown to be active in AHL libraries. [Geske, G. D.; O'Neill, J. C.; Miller, D. M.; Mattmann, M. E.; Blackwell, H. E., Modulation of Bacterial Quorum Sensing: Systematic Evaluation of N-Acylated Homoserine Lactones in Multiple Species and New Insights into Their Mechanism of Action. J. Am. Chem. Soc. 2007, 129, 13613-13625.]

The first focused library (FIG. 6) was a racemic homoserine thiolactone library, synthesized from 1-ethyl-3-(3-dimethyl aminopropyl) carbodiimide (EDC) couplings between homoserine thiolactone and the appropriate carboxylic acid (Scheme 2).

Figure 6:
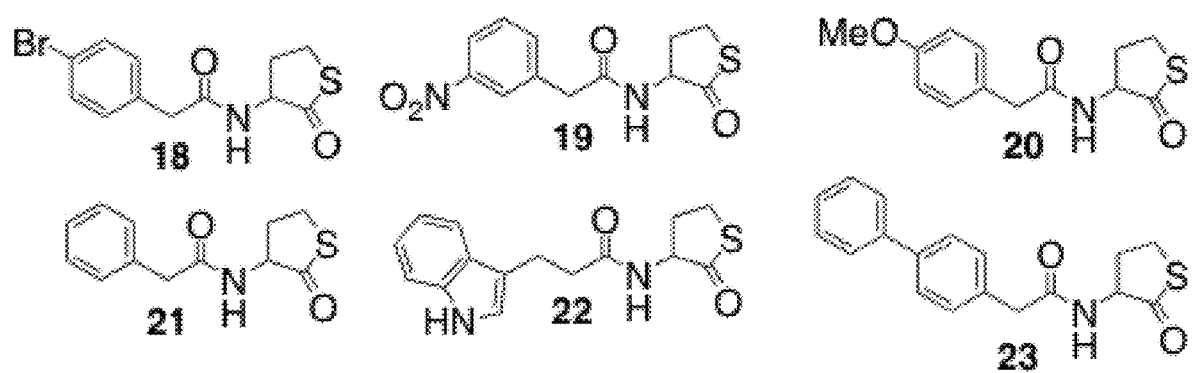
FIG. 6 provides structures (with reference numbers) of the racemic thiolactone library prepared as illustrated in Scheme 2.

Scheme 2 provides EDC coupling synthesis to make the racemic thiolactone library illustrated in FIG. 6.

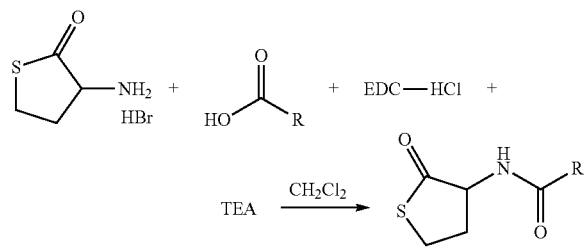

This method can be employed for synthesis of various compounds herein by choice of starting materials and routine adaptation of methods disclosed herein or of methods that are well-known in the art. This method can be used for synthesis of compounds, where R is various substituted and unsubstituted heterocyclic rings, in particular, where R is a ring substituted thiolactone group. Appropriate starting materials for making ring-substituted compounds of this inventions are readily available either form commercial sources or by known synthetic methods. Additional references which provide details useful in the synthesis of thiolactones of this invention include among others U.S. Pat. Nos. 3,840,534 and 3,926,965 and Krasncv et al. (1999) Russian J. Org. Chem. 35(4):572-577.

Figure 7A:
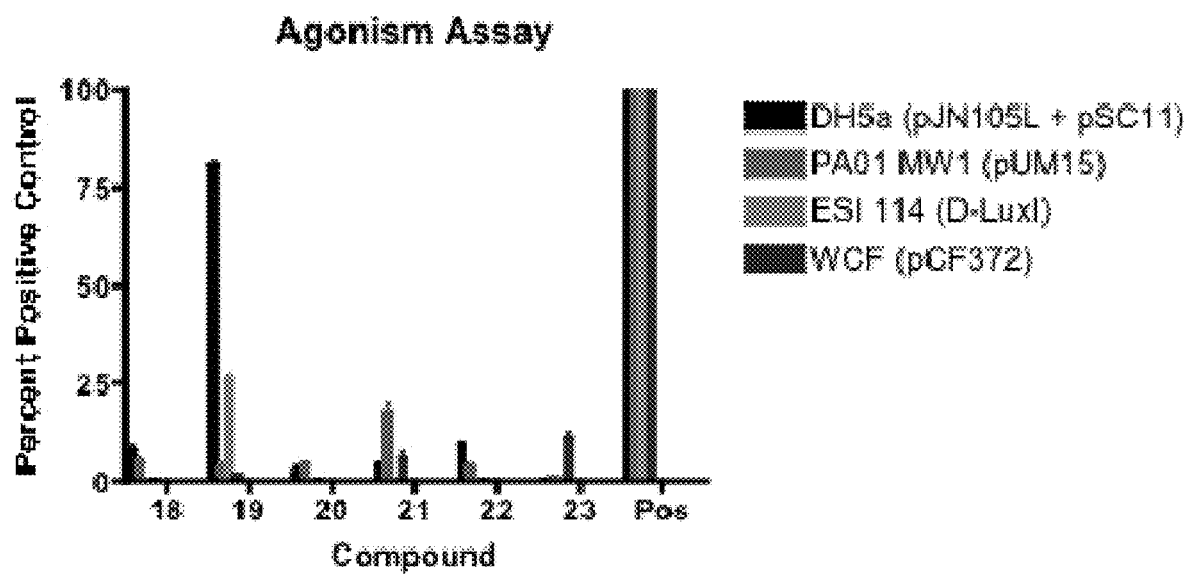
FIGS. 7A and 7B are bar grafts presenting results of agonism (7A) and antagonism (7B) assays for the racemic thiolactone library (FIG. 6). The biological testing conditions were the same as described in FIGS. 5A and 5B, respectively.
Figure 7B:
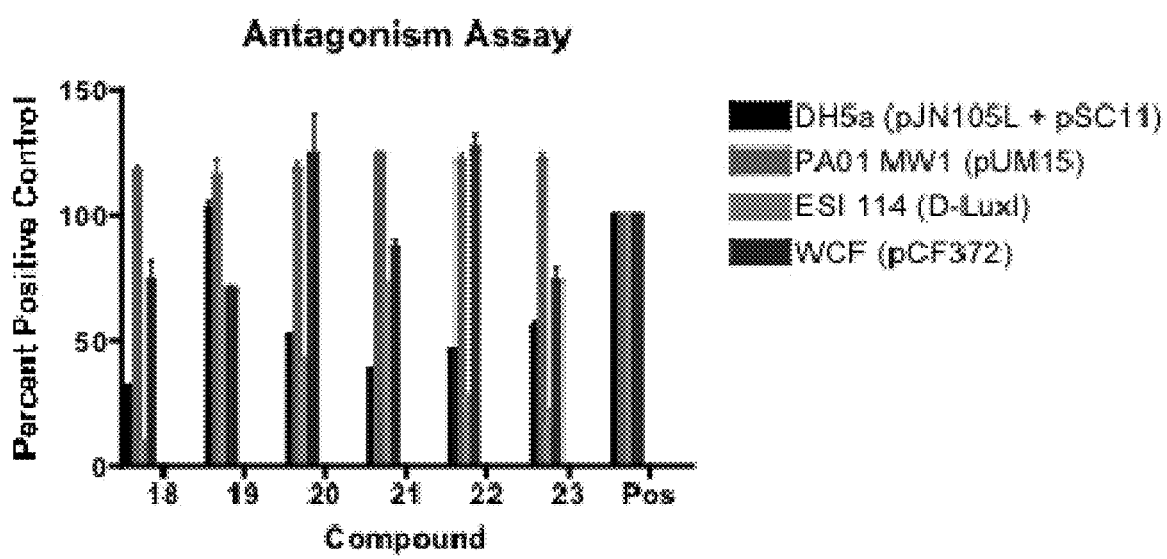

The racemic thiolactone library was tested in the same LasR reporter strains as the initial library (FIGS. 7A and 7B). Differences between the isolated LasR reporter system and LasR reporter system in the natural P. aeruginosa background have been uncovered in this second generation library. All of the library members were active in the heterologous LasI/R system while inactive in the intact P. aeruginosa QS system. One possibility is that library members are regulating multiple competing QS pathways, resulting in net inactivity in the natural background. For this reason it is crucial to examine the LasI/R system in the natural P. aeruginosa background where additional QS subsystems are also present and not simply as an isolated system in the E. coli background. Differences in cell permeability, especially since P. aeruginosa is known to be less permeable than E. coli, could also account for the discrepancy in activity between the two strains.

Example 3: Focused Libraries-Enantiopure Thiolactone Library

Figure 8:
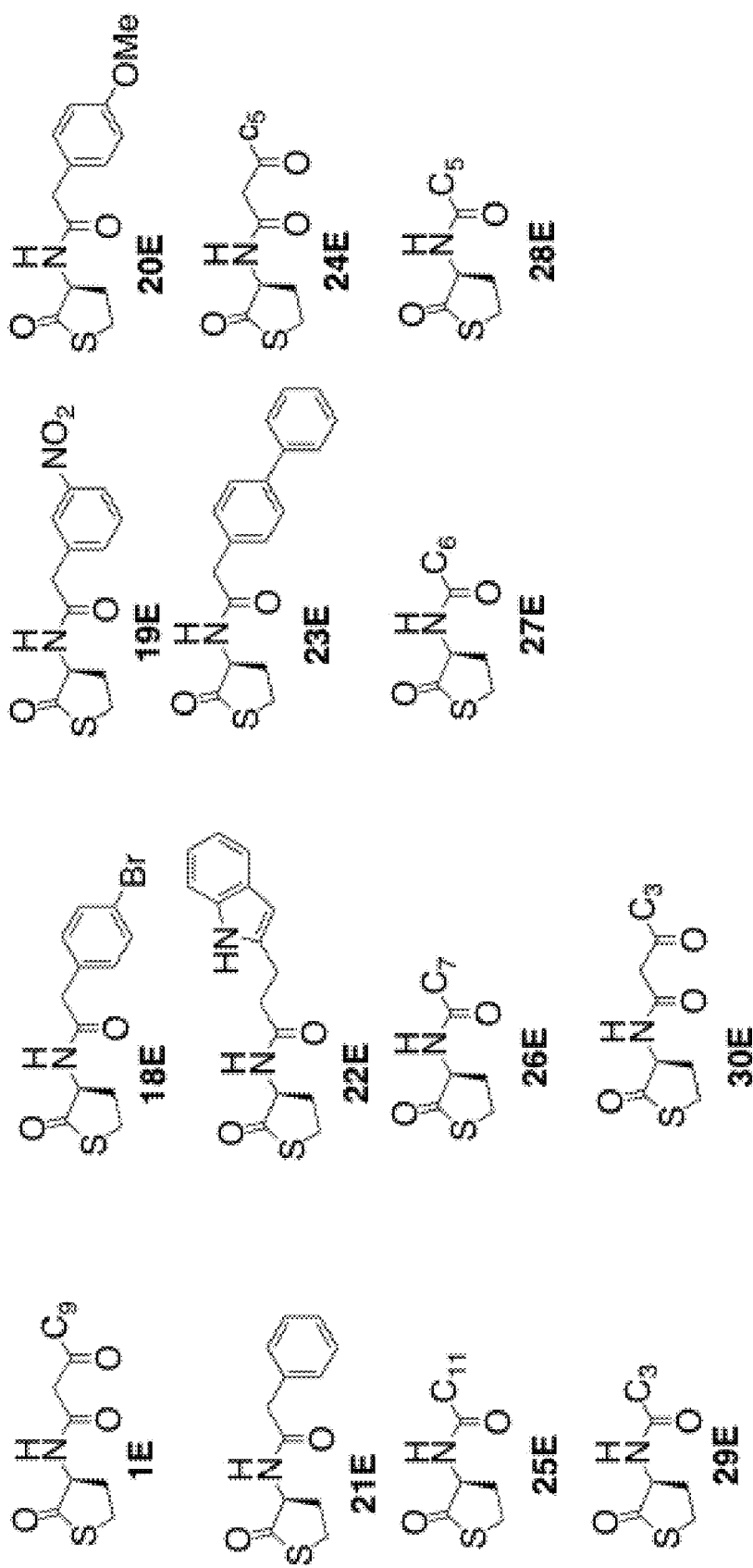
FIG. 8 provides structures (with reference numbers) of the enaltiopure thiolactone library and EDC couplings.
Figure 9A:
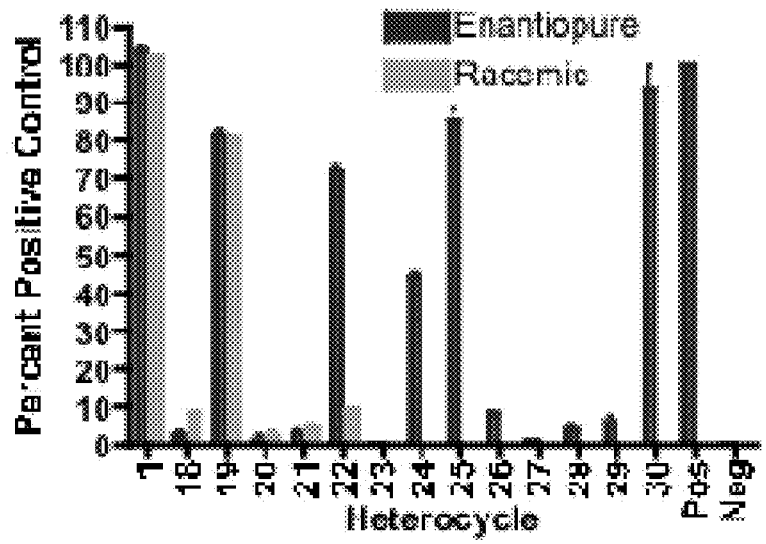
FIGS. 9A-9H are bar grafts comparing agonism and antagonism of the racemic and enantiopure compounds of Libraries of FIG. 6 and FIG. 8. All synthetic ligands were tested at 10 µM using standard methods described in FIGS. 5A and 5B.
Figure 9B:
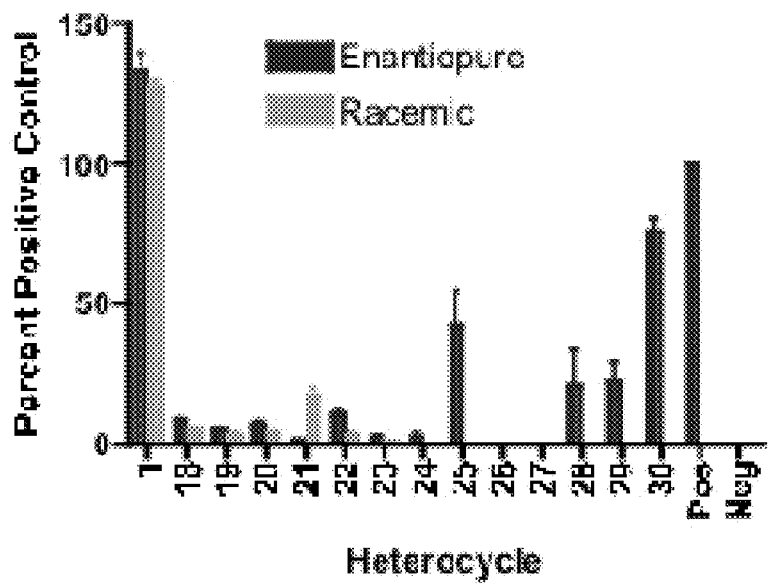
Figure 9C:
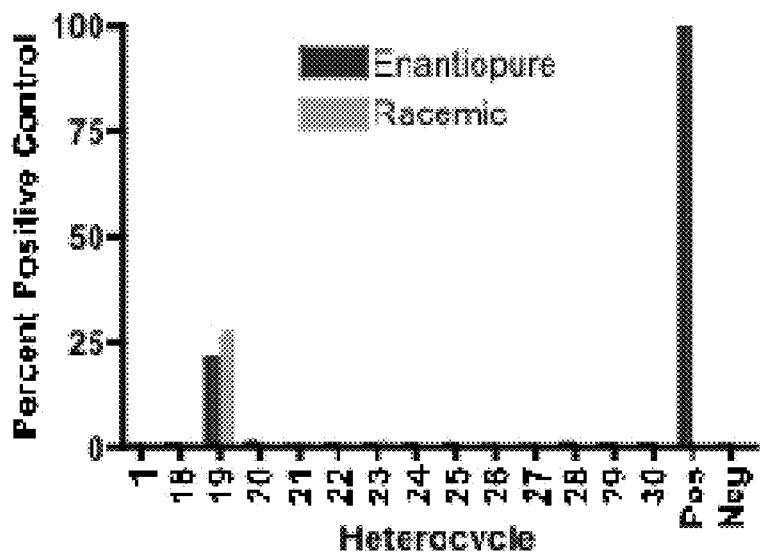
Figure 9D:
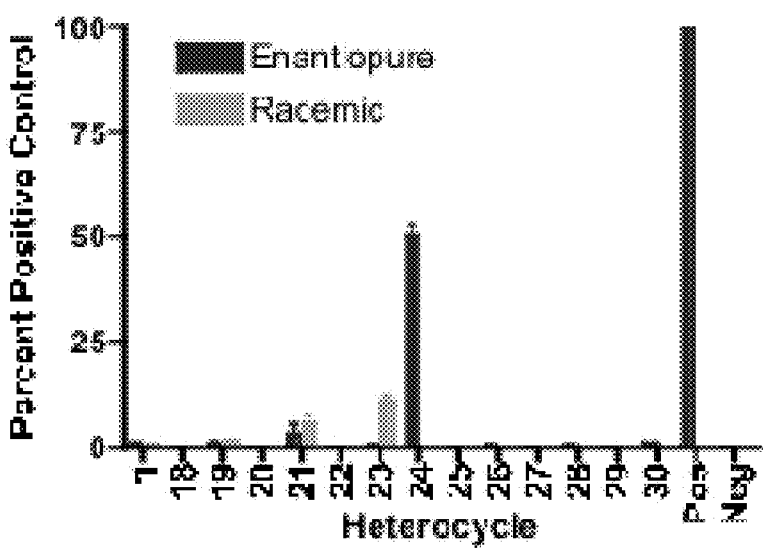
Figure 9E:
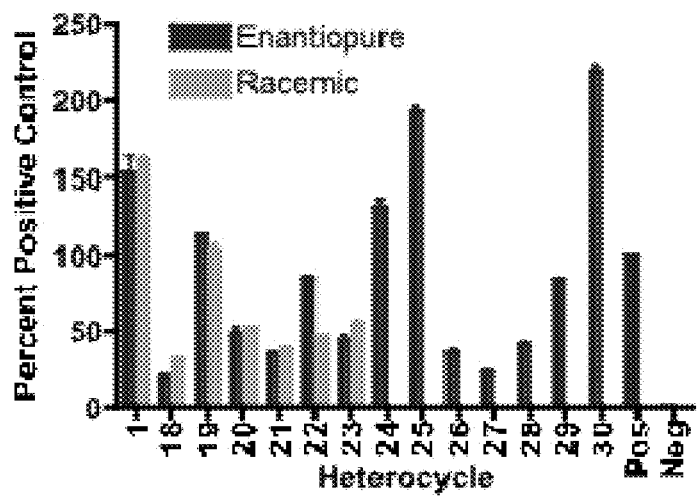
Figure 9F:
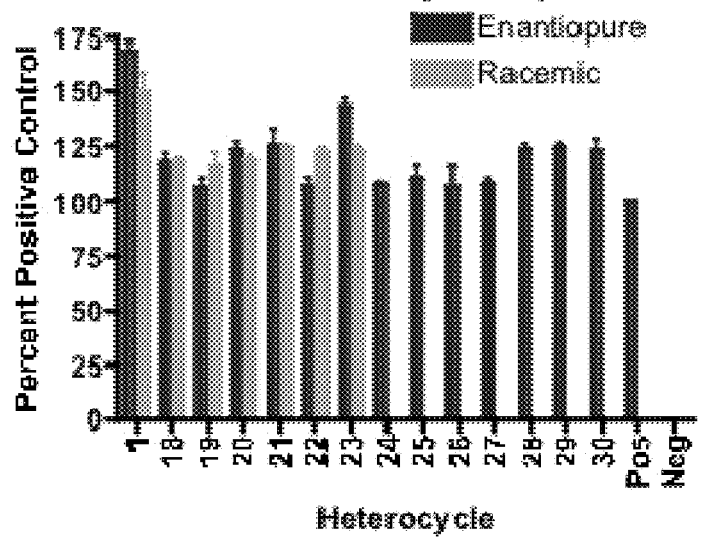
Figure 9G:
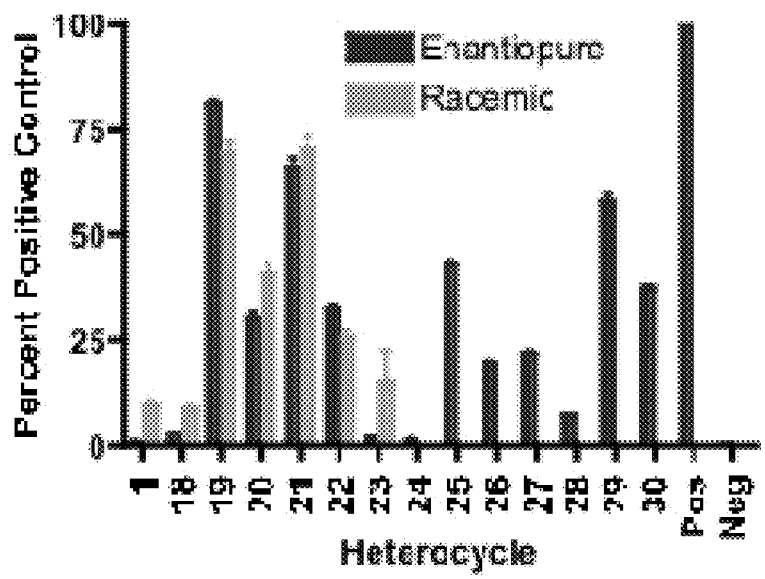
Figure 9H:
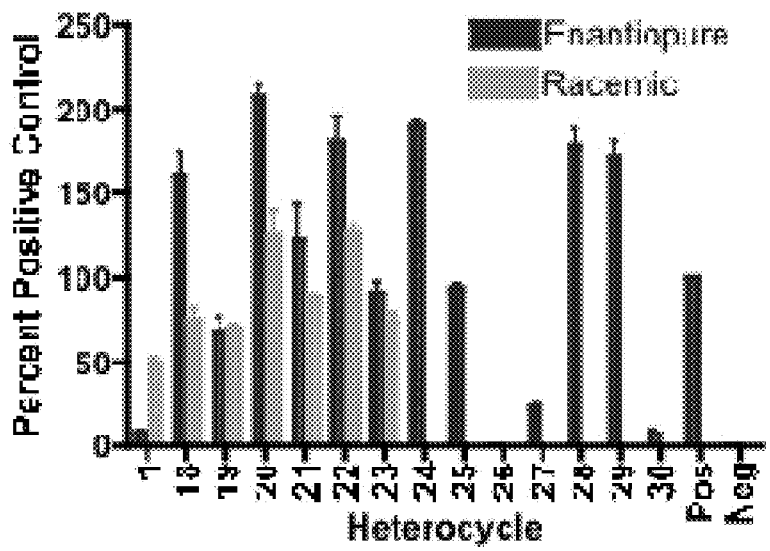

After finding several active compounds in the racemic thiolactone library in the heterologous E. coli LasI/R strain and the V. Fischeri strain, a third generation library was designed containing the enantiopure thiolactone along with additional acyl chain mimics to further explore the structure-activity relationship of the thiolactone head group (FIG. 8). The L enantiomer of the thiolactone was chosen based on previous studies that found the L enantiomer of P. aeruginosa's natural autoinducer to be active and the D enantiomer to be inactive. [Geske, G. D.; O'Neill, J. C.; Miller, D. M.; Mattmann, M. E.; Blackwell, H. E., Modulation of Bacterial Quorum Sensing: Systematic Evaluation of N-Acylated Homoserine Lactones in Multiple Species and New Insights into Their Mechanism of Action. J. Am. Chem. Soc. 2007, 129, 13613-13625; Glansdorp, F. G.; Thomas, G. L.; Lee, J. K.; Dutton, J. M.; Salmond, G. P. C.; Welch, M.; Spring, D. R., Synthesis and stability of small molecule probes for Pseudomonas aeruginosa quorum sensing modulation. Org. Biomol. Chem. 2004, 2, 3329-3336.]

FIG. 8 provides structures (with reference numbers) of compounds of the enantiopure thiolactone library synthesized from a combination of Meldrum's acid precursors and EDC couplings.

The third generation thiolactone compounds were similarly tested in bacterial assays beside the racemic version, if synthesized, to determine the effect of stereochemistry on activity (FIGS. 9A-9H). FIGS. 9A-9H provide a comparison between racemic and enantiopure thiolactone analogs. All synthetic ligands were tested at 10 µM using standard methods described in FIGS. 5A and 5B. Compounds 24-30 of the enantiopure library were not compared to a racemic counterpart. If stereochemistry played a large role in binding, the enantiopure compounds were expected to have approximately twice the activity of the racemic compounds when screened at 10 µM total synthetic ligand in each case. In both strains testing for LasR activity, it appeared, however, that stereochemistry was not important for activity of the non-native thiolactones in contrast to the lactones. Without wishing to be bound by any particular theory, we presently believe that binding is likely less specific for the thiolactones compared to the natural lactone ligand, where it is known that the L enantiomer is far more active than the D enantiomer.

Dose response analysis for the active enantiopure thiolactone compounds was conducted to quantify the activity of the synthetic ligands (Table 2). The activity of the thiolactone head group alone became evident through compound 21E in the heterologous LasR strain, whose AHL analogue was found to have little activity. [Geske, G. D.; O'Neill, J. C.; Miller, D. M.; Mattmann, M. E.; Blackwell, H. E., Modulation of Bacterial Quorum Sensing: Systematic Evaluation of N-Acylated Homoserine Lactones in Multiple Species and New Insights into Their Mechanism of Action. J. Am. Chem. Soc. 2007, 129, 13613-13625.]

Based on the results of the enantiopure thiolactone dose response data, it appears that relatively long or electron withdrawing side chains are excellent antagonists of LasR isolated in the E. coli background. However, natural ligand mimics 1E and 25E are strong agonists for the heterologous LasR system. All of the active compounds in PA01 MW1 (PUM15) (P. aeruginosa natural background) were also active in E. coli DH5α (pJN105L+pSC11). However, a significant number of the compounds active in the E. coli DH5α (pJN105L+pSC11) strain were not active in the P.

aeruginosa PA01 MW1 (PUM15) strain. These findings corroborate our hypothesis that when LasR is evaluated in the natural *P. aeruginosa* background a muted effect is may be seen due to the effects of the other QS systems present in intact *P. aeruginosa*, such as QscR and the PQS system. A variety of other effects could be contributing to the differences seen between the two strains, including differences in cell permeability.

TABLE 2

Table 2. The $IC_{50}$ and $EC_{50}$ values for the most active enantiopure thiolactone library members.

| Comp. # | DH5α (pJN105L + pSC11) E. Coli | | PA01 MW1 (pUM15) P. aeruginosa | | ESI 114 (Δ-LuxI) V. fischeri | | WCF (pCF372) A. tumefaciens | |
|---|---|---|---|---|---|---|---|---|
| | $IC_{50}$ (μM) | $EC_{50}$ (μM) | $IC_{50}$ (μM) | $EC_{50}$ (μM) | $IC_{50}$ (μM) | $EC_{50}$ (μM) | $IC_{50}$ (μM) | $EC_{50}$ (μM) |
| 1E | | 0.092 | | 3.2 | 0.45 | | 1.8 | |
| 18E | 0.40 | | | | 0.77 | | | |
| 19E | | 4.1 | | | | | 11 | |
| 20E | 7.2 | | | | | | | |
| 21E | 2.5 | | | | | | | |
| 22E | | 1.8 | | | | | | |
| 23E | 2.9 | | | | 0.35 | | | |
| 24E | | | | | 0.35 | | | 20 |
| 25E | | 1.9 | | 21 | | | | |
| 26E | 0.14 | | | | 0.13 | | 2.8 | |
| 27E | 0.79 | | | | 0.31 | | 10 | |
| 28E | 1.1 | | | | 0.84 | | | |
| 30E | | 0.13 | | 13 | | | 3.2 | |

Activity differences between the two strains evaluating LasR raise questions about the integrity and degradation of the ligands since the incubation time in the assay for the heterologous strain is shorter than for the native *P. aeruginosa* strain. It is well known that the homoserine lactone ring, used by all of the bacterial species of interest as their autoinducer head group, is prone to hydrolysis at pH 7 and above. [Eberhard, A.; Widrig, C. A.; MaBath, P.; Schineller, J. B., Analogs of the autoinducer of bioluminescence in *Vibrio fischeri*. Arch. Microbiol. 1986, 146, 35-40; Schaefer, A. L.; Hanzelka, B. L.; Eberhard, A.; Greenberg, E. P., Quorum sensing in *Vibrio fischeri*: Probing autoinducer-LuxR interactions with autoinducer analogs. *J. Bacteriol.* 1996, 178, 2897-2901; Byers, J. T.; C., L.; Salmond, G. P. C.; Welch, M., Nonenzymatic turnover of an *Erwinia carotovora* quorum sensing signaling molecule. *J. Bacteriol.* 2002, 184, 1163-1171.] Previous literature has indicated that the *P. aeruginosa* natural autoinducer has a half-life of approximately two days in growth media at 37° C., while shorter chain AHLs degrade in even shorter periods of time. [Glansdorp, F. G.; Thomas, G. L.; Lee, J. K.; Dutton, J. M.; Salmond, G. P. C.; Welch, M.; Spring, D. R., Synthesis and stability of small molecule probes for *Pseudomonas aeruginosa* quorum sensing modulation. *Org. Biomol. Chem.* 2004, 2, 3329-3336; Yates, E. A.; Philipp, B.; Buckley, C.; Atkinson, S.; Chhabra, S. R.; Sockett, R. E.; Goldner, M.; Dessaux, Y.; Camara, M.; Smith, H.; Williams, P., N-Acylhomoserine lactones undergo lactonolysis in a pH-, temperature-, and acyl chain length dependent manner during growth of *Yersinia pseudotuberculosis* and *Pseudomonas aeruginosa*. *Infect. Immun.* 2002, 70, 5635-5646]

Finding QS antagonists and agonists that are more hydrolytically stable are of considerable interest, since molecules that hydrolyze rapidly are not ideal therapeutic agents or biological probes. While many of the compounds synthesized in the initial library are non-hydrolyzable, the thiolactone derivative of the natural ligand (1E) is hydrolyzable. However, the differences in activities between the thiolactone derivatives and the natural lactone derivatives make the thiolactone derivatives both worthwhile to pursue as a target and for further half-life experiments.

Table 3 provides a summary of data for the antagonism assay for compounds tested having thiolactone head groups against selected bacteria. Compounds exhibiting 50% or higher inhibition in assays with *Escherichia coli* and *Agrobacterium tumefaciens* and those exhibiting 20% or higher inhibition with *Vibrio fischeri* are preferred for applications for disrupting bacterial quorum sensing, particularly in *Escherichia coli*, *Agrobacterium tumefaciens* and *Vibrio fischeri* strains, and for inhibiting and/or disrupting biofilm formation, particularly in *Escherichia coli*, *Agrobacterium tumefaciens* and *Vibrio fischeri* strains.

TABLE 3

Antagonism Assay Data Thiolactone Libraries

| E. coli | | V. fischeri | | A. tumefaciens | |
|---|---|---|---|---|---|
| Comp # | Inhib % | Comp # | Inhib % | Comp # | Inhib % |
| 18 | 80 | 1 | 99 | 26E | 99 |
| 27E | 78 | 24E | 99 | 30E | 93 |
| 18E | 68 | 23 | 98 | 1 | 92 |
| 21 | 65 | 18 | 97 | 27E | 78 |
| 26E | 64 | 28E | 93 | 1E | 51 |
| 21E | 61 | 1E | 91 | 19 | 33 |
| 28E | 59 | 18E | 91 | 19E | 30 |
| 23 | 56 | 23E | 85 | 23E | 26 |
| 22E | 54 | 26E | 80 | 18E | 25 |
| 20 | 51 | 27E | 78 | 21E | 13 |
| 20E | 48 | 22E | 75 | 23 | 9 |
| 23E | 45 | 20 | 70 | 25E | 6 |
| 29E | 17 | 22 | 68 | 21 | −22 |
| 22 | 16 | 30E | 62 | 20E | −24 |
| 19E | −3 | 20E | 59 | 22E | −26 |
| 19 | −13 | 25E | 57 | 18 | −60 |
| 24E | −30 | 29E | 42 | 29E | −70 |
| 1 | −40 | 21 | 34 | 28E | −78 |
| 1E | −61 | 19E | 30 | 22 | −80 |
| 25E | −93 | 21E | 30 | 24E | −89 |
| 30E | −119 | 19 | 19 | 20 | −107 |

Table 4 provides a summary of data for the agonism assay for compounds tested having thiolactone head groups with certain bacteria. Compounds exhibiting 50% or higher inhibition in assays with *Escherichia coli* and *P. aeruginosa* are preferred for applications for activating bacterial quorum sensing, particularly in *Escherichia coli*, and *P. aeruginosa* strains and for activating biofilm formation therein.

TABLE 4

Agonism Assay Data for Thiolactones

| E. coli | | P. aeruginosa | |
|---|---|---|---|
| Comp # | Act % | Comp# | Act % |
| 1E | 102 | 1E | 127 |
| 1 | 94 | 1 | 88 |
| 26E | 85 | 30E | 76 |
| 19 | 82 | 25E | 42 |
| 19E | 81 | 29E | 22 |
| 22E | 72 | 28E | 20 |
| 23 | 9 | 21E | 17 |
| 18E | 8 | 22 | 10 |
| 27E | 8 | 18 | 8 |
| 30E | 6 | 20 | 7 |

TABLE 4-continued

Agonism Assay Data for Thiolactones

| E. coli | | P. aeruginosa | |
|---|---|---|---|
| Comp # | Act % | Comp# | Act % |
| 22 | 4 | 18E | 5 |
| 25E | 4 | 19 | 5 |
| 29E | 4 | 20E | 4 |
| 21E | 3 | 19E | 3 |
| 18 | 2 | 22E | 3 |
| 21 | 2 | 23 | 3 |
| 20 | 1 | 24E | 3 |
| 28E | 1 | 21 | 2 |
| 20E | 0 | 23E | 1 |
| 23E | 0 | 26E | 0 |
| 24E | 0 | 27E | 0 |

Example 4: Comparison of Functional Half-Lives of Autoinducers

A biologically based assay was developed to determine the functional half-life of the *P. aeruginosa* natural ligand, OdDHL, and the corresponding thiolactone analog (1E). This assay does not directly measure hydrolysis, but rather the ability of the degraded ligand to cause a QS response. However, previous experiments have shown that the hydrolysis half-life for the *P. aeruginosa* natural ligand, OdDHL, is approximately two days, while racemization of the chiral center was found to be less than 5% over the course of a week. [Glansdorp, F. G.; Thomas, G. L.; Lee, J. K.; Dutton, J. M.; Salmond, G. P. C.; Welch, M.; Spring, D. R., Synthesis and stability of small molecule probes for *Pseudomonas aeruginosa* quorum sensing modulation. Org. Biomol. Chem. 2004, 2, 3329-3336.] This data suggests that most ligand degradation is due to hydrolysis and not epimerization. In these cases the results were determined by NMR experiments conducted in deuterated buffers. Due to problems with the water solubility of OdDHL, a 50% solution of DMSO was used. Unfortunately, the use of high levels of DMSO reduces the biological relevance of the assay because large concentrations of DMSO cannot be tolerated by biological systems. Furthermore, the required concentrations of ligand are lower in a biologically based functional assay than in an NMR experiment because YFP production is much more sensitive than NMR, which requires relatively high concentrations.

Figure 10A:
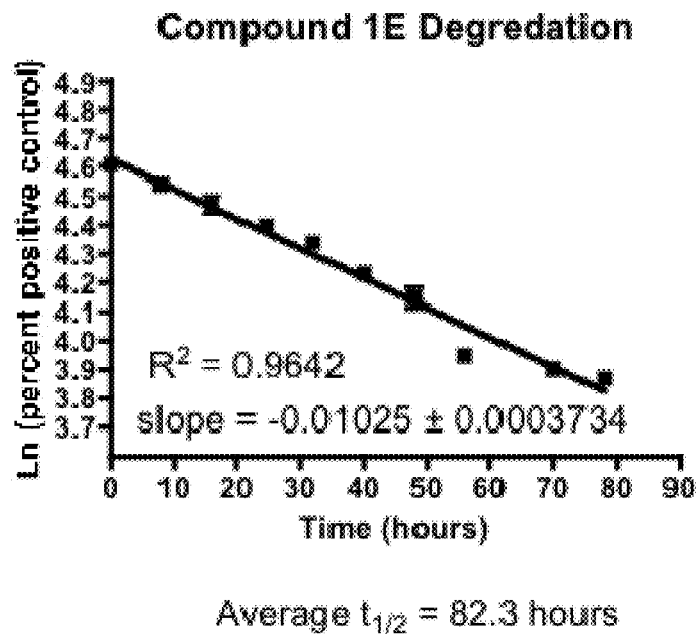
FIGS. 10A and B are graphs comparing the functional half-lives of autoinducers as described in Example 4.
Figure 10B:
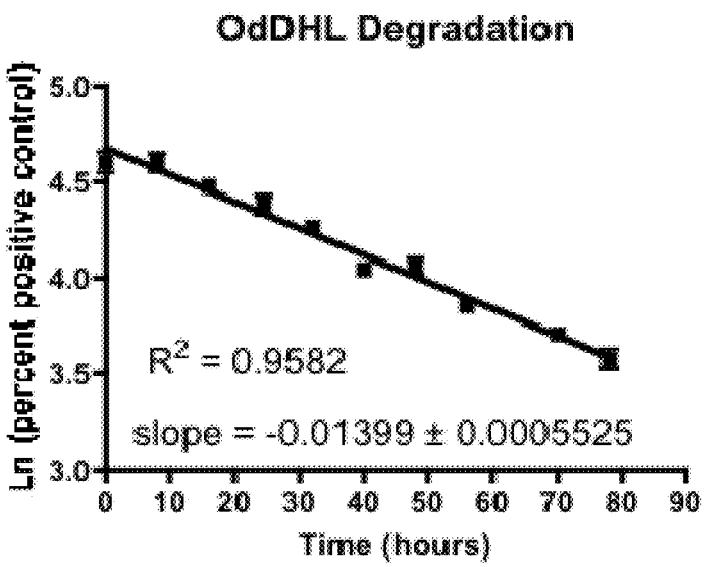

In this assay, media, ligand, and antibiotics are prepared in Teflon-capped vials and allowed to incubate at 37° C. for predetermined times. *P. aeruginosa* cells from the strain PA01 MW1 (pUM15) were cultured overnight. These cells were then pelleted and washed with LB containing 50 mM MOPS. After washing, the cells were resuspended in a minimal amount of media containing antibiotics and were added to a 96 well plate containing the media, natural ligand, and antibiotic previously prepared and incubated for specific, predetermined times. At this point, the optical density at 600 nm of the cells was comparable to the optical density after subculturing the cells during a traditional assay. The 96 well plate was incubated for 8 hours and then analyzed for optical density and YFP fluorescence. Bacteria were cultured, pelleted, and washed before addition to the assay plate. A traditional PA01 MW1 assay is completed to analyze for ligand degradation. Fluorescence was normalized to cell density and time points were analyzed as a percentage of the ability of the freshly prepared natural ligand to agonize the *P. aeruginosa* system. Since we predict that the ligand degradation is a product of hydrolysis, we assumed a pseudo first order rate and plotted the natural log of the agonism as a percent of the fresh natural ligand versus time. The slope of the graph can be used to determine the half-life of the ligand according to the formula $t1/2=\ln(2)/\text{slope}$ (FIGS. 10A and 10B).

We found the half-life for the OdDHL natural ligand to be 48.2 hours. This value corresponds closely with the previously found hydrolysis half-life of approximately two days. [Glansdorp, F. G.; Thomas, G. L.; Lee, J. K.; Dutton, J. M.; Salmond, G. P. C.; Welch, M.; Spring, D. R., Synthesis and stability of small molecule probes for *Pseudomonas aeruginosa* quorum sensing modulation. Org. Biomol. Chem. 2004, 2, 3329-3336.]

A similar analysis found the half-life of the thiolactone analog of the OdDHL *P. aeruginosa* natural ligand (1E) to be 82.3 hours. In the case of both the natural ligand and the thiolactone analog, the half-life of the compounds are sufficiently long so that standard in vitro assays on the time scale of 8 hours or less are testing the ligand in its native form. This is important because previous work has shown that the ring open form of the natural ligand is inactive. [Yates, E. A.; Philipp, B.; Buckley, C.; Atkinson, S.; Chhabra, S. R.; Sockett, R. E.; Goldner, M.; Dessaux, Y.; Camara, M.; Smith, H.; Williams, P., N-Acylhomoserine lactones undergo lactonolysis in a pH-, temperature-, and acyl chain length dependent manner during growth of *Yersinia pseudotuberculosis* and *Pseudomonas aeruginosa*. Infect. Immun. 2002, 70, 5635-5646; Kapadnis, P. B.; Hall, E.; Ramstedt, M.; Galloway, W. R. J. D.; Welch, M.; Spring, D. R., Towards quorum-quenching catalytic antibodies. Chem. Commun. 2009, (5), 538-540.]

It is interesting to note that the half-life of 1E is slightly less than double the half-life of OdDHL, the natural ligand. This is particularly intriguing because one would expect the sulfur analog to have a faster hydrolysis rate from an electronics argument. Our current hypothesis is that although compound 1E is able to ring open faster than OdDHL, 1E is also able to recyclize at a faster rate than the natural ligand. Previous analysis of lactone hydrolysis has shown that once ring opened, the lactone does not reclose in appreciable quantities until under pH 2 due to differences in the mechanisms for ring opening and closing. [Yates, E. A.; Philipp, B.; Buckley, C.; Atkinson, S.; Chhabra, S. R.; Sockett, R. E.; Goldner, M.; Dessaux, Y.; Camara, M.; Smith, H.; Williams, P., N-Acylhomoserine lactones undergo lactonolysis in a pH-, temperature-, and acyl chain length dependent manner during growth of *Yersinia pseudotuberculosis* and *Pseudomonas aeruginosa*. Infect. Immun. 2002, 70, 5635-5646.} In order for the lactone ring to close, the pH must first approach the pKa of the carboxyl group so that significant amounts of the acid as opposed to the acid salt are present. The differences in ring opening and closing mechanisms may cause the natural ligand to take longer to ring open, but remain ring opened, while the sulfur analog would ring open faster and close back up again so that it would have a longer hydrolysis half-life than the natural ligand. Conversely, the sulfur's increased nucleophilicity may be able to hold the lactone ring together in aqueous solution better than the corresponding oxygen.

Example 5: Focused Libraries-Non-Hydrolyzable Head Groups

While many of the natural ligands for QS systems contain a lactone ring, it would be advantageous to find QS modulators that are not prone to hydrolysis or degradation. To this end focused libraries based on non-hydrolyzable head groups screened in the initial library were designed, synthesized, and screened. Head groups based upon glycine ethyl ester (16), cyclopentyl amine (3), and aniline (2) were chosen as particularly interesting non-hydrolyzable head groups based on activity in the initial library screens.

The glycine ethyl ester head group is particularly interesting because the stereochemistry has been removed from the head group. The glycine ethyl ester head group is derived from the lactone ring when a disconnection is made between the carbons 2 and 3 in the lactone ring. (Scheme 3).

Scheme 3

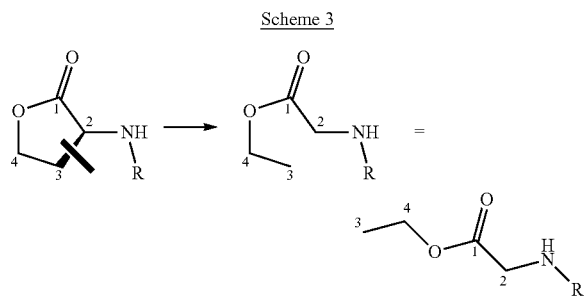

Figure 11:
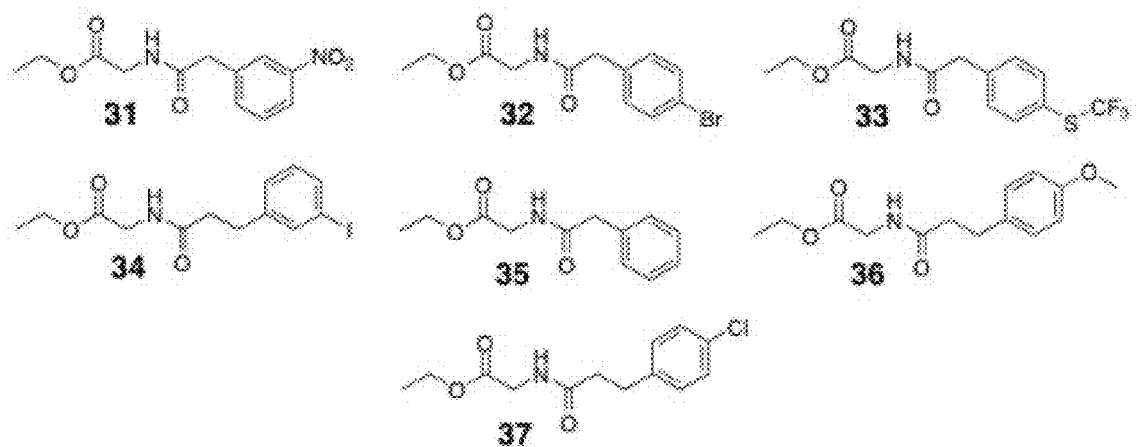
FIG. 11 provides structures (with reference numbers) of compounds having glycine ethyl ester structures.
Figure 12A:
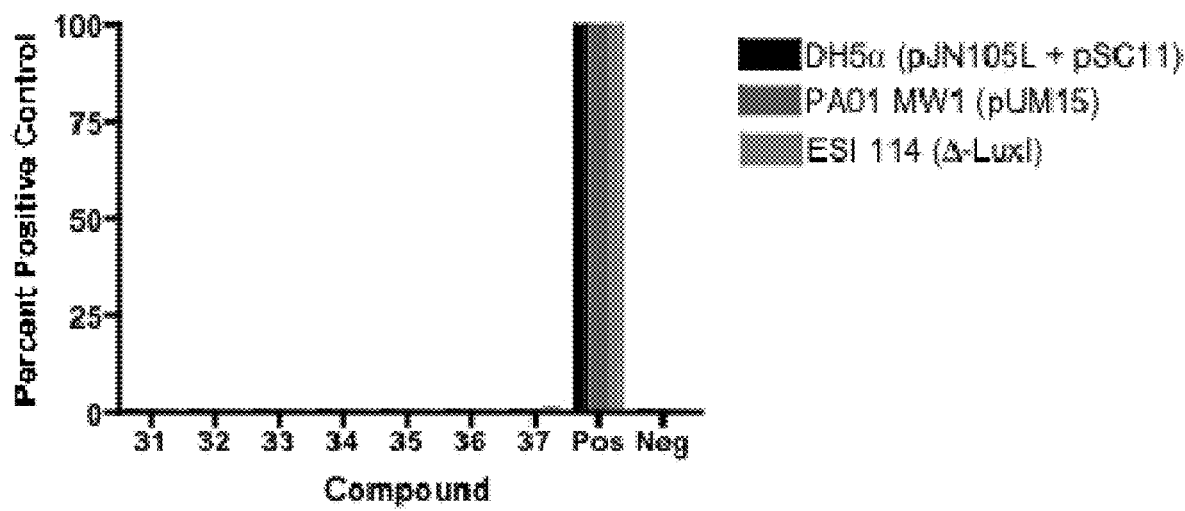
FIGS. 12A and 12B are bar graphs with results of activity assays of the glycine ethyl ester library (for agonism 12A and antagonism 12 B) according to the assay conditions described in FIGS. 5A and 5B.
Figure 12B:
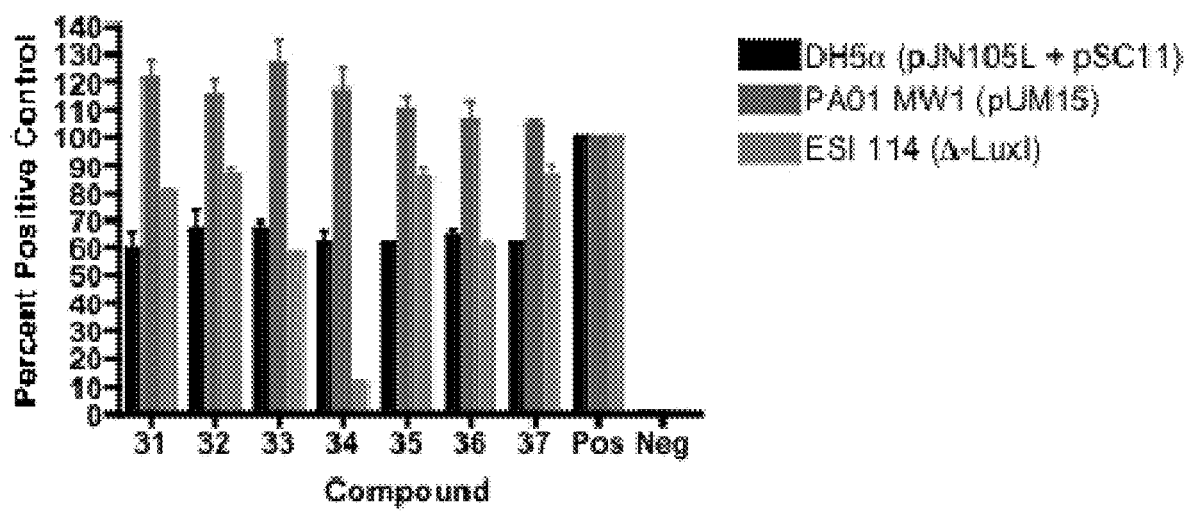

While the compounds of this library (FIG. 11) are non-natural analogs of the lactone ring, it is interesting that some activity can be observed. One characteristic of this library is that the compounds appear to be cooperative agonists because many of the library members show heightened activity in antagonistic assays and minimal activity in agonistic assays (FIGS. 12A and 12B). Compound 34 showed excellent antagonistic activity in *V. fischeri*. While most library members do not seem to fit as traditional agonists or antagonists, further analysis could yield important information about alternative binding sites or methods, or information about dimerization requirements.

Figure 13:
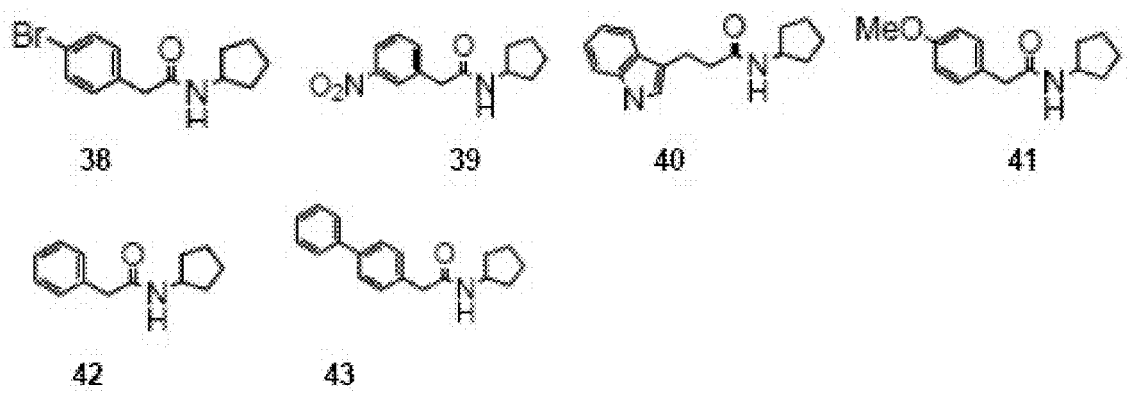
FIG. 13 provides structures (with reference numbers) of an exemplary library having cyclopentyl amine head groups.
Figure 14:
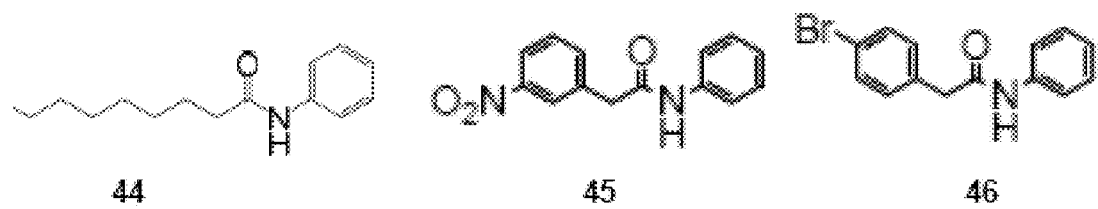
FIG. 14 provides structures (with reference numbers) of an exemplary library having aniline head groups.
Figure 15A:
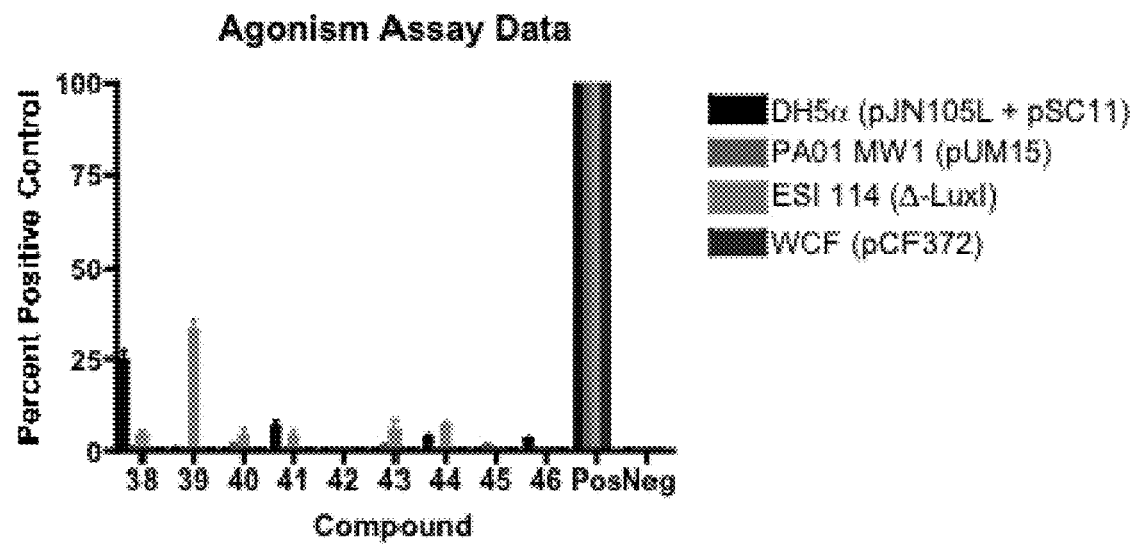
FIGS. 15A and 15B are bar graphs with results of activity assays of the compounds of FIGS. 13 and 14 (for agonism 15A and antagonism 15 B) according to the assay conditions described in FIGS. 5A and 5B.
Figure 15B:
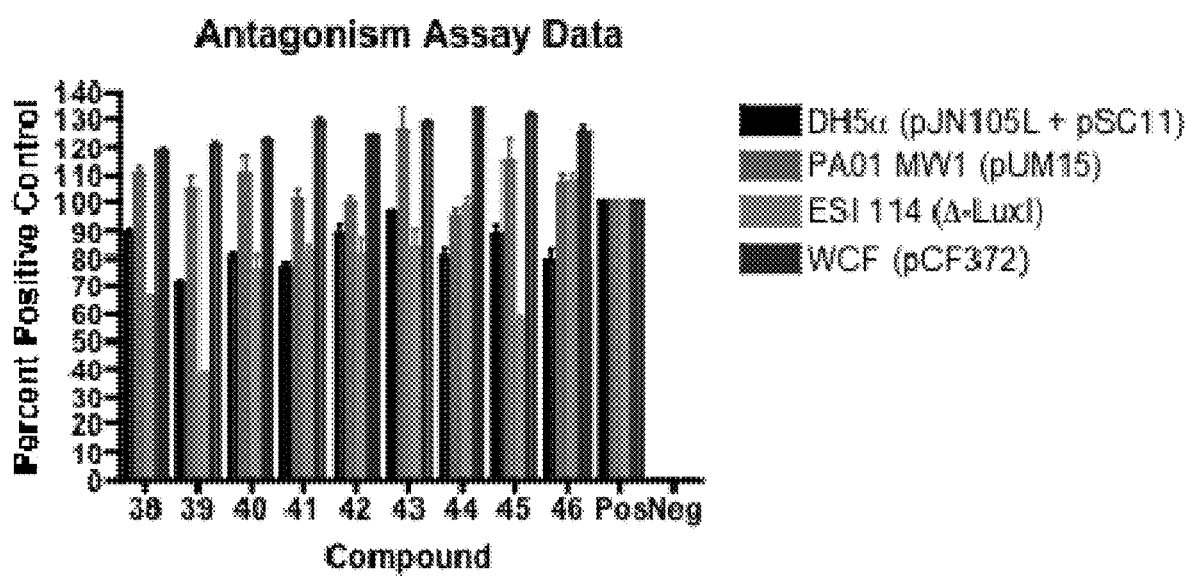

Cyclopentyl amine and aniline were used to synthesize libraries to explore the activity of ligands with a lack of hydrogen bonding capabilities on the head group (FIG. 13 (cyclopentyl amine library HG=cyclopentyl), FIG. 14 (analine library, HG=phenyl)). Agonism and antagonism assays, performed as described above, are illustrated in FIGS. 15A and 15B, respectively. While these carbocycles were active when appended with the 3-oxo dodecanoyal containing acyl chain, only moderate activities were observed when paired with acyl tail mimics. These studies show that viable agonists and antagonists can be found either by altering the head group of the natural ligand or by creating acyl tail mimics. However, when both the head group and the acyl tail are modified in the same molecule, the molecule doesn't always combine the activities of the two initial modifications. In fact, the dual modifications are frequently deleterious to the activity of the molecule.

Pursuing QS modulators that are either non-hydrolyzable or hydrolyze slowly allows for new biological probes or therapeutics. It is important for therapeutics to remain biologically active for extended periods of time yet be cleared from the body in a time dependent manner. Compounds like the thiolactone derivatives of this invention may serve as excellent therapeutics because they are active for longer periods of time than the natural lactone analogs, yet do lose activity in a time dependent fashion.

We claim:

1. A compound of formula I:

A-[Z]$_n$-L1-[Y]—NH-L2-HG or a pharmaceutically acceptable salt thereof
    wherein:
    n is 0 and Z is absent;
    Y is —CO—CH$_2$—CO—;
    L1 and L2 independently are —[CH$_2$]$_{p1}$— and —[CH$_2$]$_{p2}$—, where p1 and p2, independently, are 0 or integers ranging from 1-3;
    A is an alkyl or alkenyl group having 4-10 carbon atoms; and
    HG is an unsubstituted cyclopentyl group.

2. The compound or salt of claim 1, wherein A is an alkyl group having 4-10 carbon atoms.

3. The compound or salt of claim 1, wherein A is an alkenyl group having 4-10 carbon atoms.

4. The compound or salt of claim 1, wherein p1 and p2 are 0.

5. The compound or salt of claim 1 of formula:

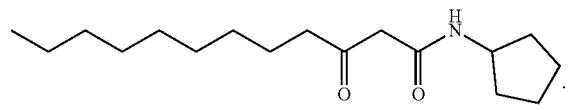 [SMILES: CCCCCCCCCC(=O)CC(=O)NC1CCCC1]

6. The compound of claim 1, wherein p1 and p2 are integers ranging from 1-3.

7. A pharmaceutical composition comprising an amount of a compound of claim 1 effective for modulation of quorum sensing in a quorum sensing bacterium.

8. A pharmaceutical composition comprising an amount of a compound of claim 5 effective for modulation of quorum sensing in a quorum sensing bacterium.

9. A method for modulating quorum sensing bacteria comprising the step of contacting a quorum sensing bacteria with an amount of a compound of claim 1 effective for modulation of quorum sensing.

10. The method of claim 9, wherein the quorum sensing bacteria are *Pseudomonas aeruginosa*.

11. A method for modulating quorum sensing bacteria comprising the step of contacting a quorum sensing bacteria with an amount of a compound of claim 5 effective for modulation of quorum sensing.

12. The method of claim 11, wherein the quorum sensing bacteria are *Pseudomonas aeruginosa*.

* * * * *